United States Patent
Soni

(10) Patent No.: US 10,278,938 B2
(45) Date of Patent: May 7, 2019

(54) METHODS OF REDUCING THE RISK OF A CARDIOVASCULAR EVENT IN A SUBJECT ON STATIN THERAPY

(71) Applicant: Amarin Pharmaceuticals Ireland Limited, Dublin (IE)

(72) Inventor: Paresh Soni, Mystic, CT (US)

(73) Assignee: Amarin Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 16/156,879

(22) Filed: Oct. 10, 2018

(65) Prior Publication Data

US 2019/0076388 A1   Mar. 14, 2019

Related U.S. Application Data

(63) Continuation of application No. 16/005,852, filed on Jun. 12, 2018, which is a continuation of application No. 15/886,422, filed on Feb. 1, 2018, now Pat. No. 10,016,386, which is a continuation of application No. 15/607,084, filed on May 26, 2017, now Pat. No. 9,918,955, which is a continuation of application No. 15/427,238, filed on Feb. 8, 2017, now Pat. No. 9,693,986, which is a continuation of application No. 15/333,991, filed on Oct. 25, 2016, now Pat. No. 9,610,272, which is a continuation of application No. 14/411,815, filed as application No. PCT/US2013/048559 on Jun. 28, 2013, now Pat. No. 9,603,826.

(60) Provisional application No. 61/666,447, filed on Jun. 29, 2012.

(51) Int. Cl.
*A61K 31/232* (2006.01)
*A61K 31/397* (2006.01)
*A61K 45/06* (2006.01)

(52) U.S. Cl.
CPC .......... *A61K 31/232* (2013.01); *A61K 31/397* (2013.01); *A61K 45/06* (2013.01)

(58) Field of Classification Search
CPC ..... A61K 31/232; A61K 31/397; A61K 45/06
USPC ........................................................ 514/552
See application file for complete search history.

(56) References Cited

U.S. PATENT DOCUMENTS

| | | |
|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,343,389 A | 8/1994 | Otvos |
| 5,385,929 A | 1/1995 | Bjorge et al. |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |
| 6,025,008 A | 2/2000 | Akahoshi |
| 6,069,168 A | 5/2000 | Horrobin et al. |
| 6,193,999 B1 | 2/2001 | Gennadios |
| 6,284,268 B1 | 9/2001 | Mishra et al. |
| 6,313,330 B1 | 11/2001 | Kiyohara et al. |
| 6,326,031 B1 | 12/2001 | Hsia et al. |
| 6,326,355 B1 | 12/2001 | Abbruzzese et al. |
| 6,331,568 B1 | 12/2001 | Horrobin |
| 6,368,621 B1 | 4/2002 | Engel et al. |
| 6,384,077 B1 | 5/2002 | Peet |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

National Kidney Foundation, "The Heart and Kidney Connection," Apr. 17, 2017 (Apr. 17, 2017), retrieved on Jul. 30, 2018 from https://web.archive.org/web/20170417004l6/https://www.kidney.org/atoz/content/heart-and-kidney-connection; entire document, especially p. 2, paragraph 1.

Zheng et al., "Function of ω-3 long chain unsaturated fatty acid in metabolic syndrome," Chinese Journal of Endocrinology and Metabolism, vol. 27, No. 9, pp. 787-790 (Sep. 30, 2011)(with English translation).

Inzucchi et al., "Diagnosis of Diabetes," New Engl. Journ of Med., 367(6):541-550 (2012).

(Continued)

*Primary Examiner* — Kristin A Vajda
(74) *Attorney, Agent, or Firm* — Perkins Coie LLP

(57) ABSTRACT

In various embodiments, the present invention provides methods of reducing the risk of a cardiovascular event in a subject on statin therapy and, in particular, a method of reducing the risk of a cardiovascular event in a subject on statin therapy having a fasting baseline triglyceride level of about 135 mg/dL to about 500 mg/dL, and administering to the subject a pharmaceutical composition comprising about 1 g to about 4 g of eicosapentaenoic acid ethyl ester or a derivative thereof.

30 Claims, No Drawings

(56) References Cited

U.S. PATENT DOCUMENTS

| | | |
|---|---|---|
| 6,479,544 B1 | 11/2002 | Horrobin |
| 6,482,421 B2 | 11/2002 | Weidner |
| 6,531,150 B1 | 3/2003 | Sunohara et al. |
| 6,555,700 B1 | 4/2003 | Horrobin et al. |
| 6,596,766 B1 | 7/2003 | Igarashi et al. |
| 6,620,821 B2 | 9/2003 | Robl |
| 6,689,812 B2 | 2/2004 | Peet |
| 6,846,942 B2 | 1/2005 | Rubin |
| 7,022,713 B2 | 4/2006 | Aoki et al. |
| 7,112,609 B2 | 9/2006 | Hermelin et al. |
| 7,119,118 B2 | 10/2006 | Peet |
| 7,205,329 B2 | 4/2007 | Chien et al. |
| 7,405,302 B2 | 7/2008 | Hutchinson et al. |
| 7,498,359 B2 | 3/2009 | Yokoyama et al. |
| 7,511,131 B2 | 3/2009 | Crooke et al. |
| 7,598,227 B2 | 10/2009 | Crooke et al. |
| 7,776,881 B2 | 8/2010 | Aoki et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 8,410,086 B2 | 4/2013 | Osterloh et al. |
| 8,431,560 B1 | 4/2013 | Manku et al. |
| 8,440,650 B1 | 5/2013 | Manku et al. |
| 8,455,472 B2 | 6/2013 | Osterloh et al. |
| 8,518,929 B2 | 8/2013 | Manku et al. |
| 8,524,698 B2 | 9/2013 | Manku et al. |
| 8,546,372 B2 | 10/2013 | Manku et al. |
| 8,551,521 B2 | 10/2013 | Manku et al. |
| 8,563,608 B2 | 10/2013 | Manku et al. |
| 8,617,593 B2 | 12/2013 | Manku et al. |
| 8,617,594 B2 | 12/2013 | Manku et al. |
| 8,618,168 B2 | 12/2013 | Fujii et al. |
| 8,623,406 B2 | 1/2014 | Manku et al. |
| 8,642,077 B2 | 2/2014 | Manku et al. |
| 8,669,245 B2 | 3/2014 | Osterloh et al. |
| 8,680,144 B2 | 3/2014 | Osterloh et al. |
| 8,691,871 B2 | 4/2014 | Osterloh et al. |
| 8,703,185 B2 | 4/2014 | Manku et al. |
| 8,709,475 B2 | 4/2014 | Manku et al. |
| 8,906,964 B2 | 12/2014 | Bobotas et al. |
| 9,006,285 B2 | 4/2015 | Ohnishi |
| 9,060,981 B2 | 6/2015 | Sato et al. |
| 9,452,150 B2 | 9/2016 | Ueshima et al. |
| 9,603,826 B2 | 3/2017 | Soni |
| 9,610,272 B2 | 4/2017 | Soni |
| 9,623,001 B2 | 4/2017 | Soni |
| 9,693,984 B2 | 7/2017 | Soni |
| 9,693,985 B2 | 7/2017 | Soni |
| 9,693,986 B2 | 7/2017 | Soni |
| 9,855,237 B2 | 1/2018 | Osterloh et al. |
| 2001/0035125 A1 | 11/2001 | Talieh et al. |
| 2002/0016312 A1 | 2/2002 | Seed et al. |
| 2002/0025983 A1 | 2/2002 | Horrobin |
| 2002/0035125 A1 | 3/2002 | Shear |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0204356 A1 | 10/2004 | Guenzler-Pukall |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0134206 A1 | 6/2006 | Iyer et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0252833 A1 | 11/2006 | Peet et al. |
| 2007/0021504 A1 | 1/2007 | Yokoyama et al. |
| 2007/0060532 A1 | 3/2007 | Junien et al. |
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0265340 A1 | 11/2007 | Shalwitz et al. |
| 2007/0269507 A1 | 11/2007 | Sachetto et al. |
| 2008/0020018 A1 | 1/2008 | Moodley et al. |
| 2008/0057115 A1 | 3/2008 | Okamoto |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0185198 A1 | 8/2008 | Jones |
| 2008/0200453 A1 | 8/2008 | Cincotta |
| 2008/0200547 A1 | 8/2008 | Peet et al. |
| 2008/0200707 A1 | 8/2008 | Shimano et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0054329 A1 | 2/2009 | Willemsen et al. |
| 2009/0105340 A1 | 4/2009 | Yokoyama |
| 2009/0156675 A1 | 6/2009 | Yokoyama et al. |
| 2009/0182049 A1 | 7/2009 | Opheim |
| 2009/0227602 A1 | 9/2009 | Griffin et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0298379 A1 | 11/2010 | Jacobsen |

(56) References Cited

U.S. PATENT DOCUMENTS

| | | |
|---|---|---|
| 2010/0305205 A1 | 12/2010 | Yokoyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0178105 A1 | 7/2011 | Gillies et al. |
| 2011/0195061 A1 | 8/2011 | Minatelli |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | MacDonald et al. |
| 2012/0195963 A1 | 8/2012 | Peet et al. |
| 2012/0207800 A1 | 8/2012 | Abu-Baker |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0264824 A1 | 10/2012 | Mizuguchi et al. |
| 2012/0295976 A1 | 11/2012 | Yokoyama |
| 2012/0302589 A1 | 11/2012 | Manku et al. |
| 2012/0329852 A1 | 12/2012 | Yokoyama |
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0065956 A1 | 3/2013 | Yokoyama |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0115284 A1 | 5/2013 | Fujii |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1 | 10/2013 | Button et al. |
| 2013/0281534 A1 | 10/2013 | Osterloh et al. |
| 2013/0295173 A1 | 11/2013 | Machielse et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0057981 A1 | 2/2014 | Fujii |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku |
| 2014/0094520 A1 | 4/2014 | Bobotas et al. |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |
| 2014/0234410 A1 | 8/2014 | Moodley et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0157592 A1 | 6/2015 | Soni |
| 2015/0157593 A1 | 6/2015 | Braeckman et al. |
| 2015/0164850 A1 | 6/2015 | Osterloh et al. |
| 2015/0190361 A1 | 7/2015 | Osterloh et al. |
| 2015/0216831 A1 | 8/2015 | Manku et al. |
| 2015/0250754 A1 | 9/2015 | Ohta |
| 2015/0250756 A1 | 9/2015 | Mason |
| 2015/0250757 A1 | 9/2015 | Soni |
| 2015/0258051 A1 | 9/2015 | Manku et al. |
| 2015/0265566 A1 | 9/2015 | Osterloh et al. |
| 2015/0265574 A1 | 9/2015 | Rowe |
| 2015/0272917 A1 | 10/2015 | Manku et al. |
| 2015/0283074 A1 | 10/2015 | Fujii |
| 2015/0290154 A1 | 10/2015 | Roberts et al. |
| 2015/0335607 A1 | 11/2015 | Rowe |
| 2015/0359775 A1 | 12/2015 | Osterloh et al. |
| 2016/0058729 A1 | 3/2016 | Manku et al. |
| 2016/0120837 A1 | 5/2016 | Manku et al. |
| 2016/0143875 A1 | 5/2016 | Zakrzewski |
| 2016/0151319 A1 | 6/2016 | Kimura |
| 2016/0158184 A1 | 6/2016 | Ito |
| 2016/0213636 A1 | 7/2016 | Manku et al. |
| 2016/0213639 A1 | 7/2016 | Suzuki et al. |
| 2016/0220522 A1 | 8/2016 | Osterloh et al. |
| 2016/0287546 A1 | 10/2016 | Osterloh et al. |
| 2017/0014366 A1 | 1/2017 | Osterloh et al. |
| 2017/0035722 A1 | 2/2017 | Soni |
| 2017/0056361 A1 | 3/2017 | Soni |
| 2017/0079946 A1 | 3/2017 | Ohta |
| 2017/0087111 A1 | 3/2017 | Mason |
| 2017/0100363 A9 | 4/2017 | Zakrzewski |
| 2017/0119721 A1 | 5/2017 | Zakrzewski |

(56) References Cited

U.S. PATENT DOCUMENTS

| | | |
|---|---|---|
| 2017/0119722 A1 | 5/2017 | Manku et al. |
| 2017/0119723 A1 | 5/2017 | Soni |
| 2017/0119724 A1 | 5/2017 | Fujii |
| 2017/0128402 A1 | 5/2017 | Manku et al. |
| 2017/0128405 A1 | 5/2017 | Osterloh et al. |
| 2017/0128406 A1 | 5/2017 | Rowe |
| 2017/0136055 A1 | 5/2017 | Zakrzewski |
| 2017/0143656 A1 | 5/2017 | Soni |
| 2017/0143657 A1 | 5/2017 | Braeckman et al. |
| 2017/0143658 A1 | 5/2017 | Soni |
| 2017/0151202 A1 | 6/2017 | Mason |
| 2017/0151206 A1 | 6/2017 | Yokoyama |
| 2017/0258753 A1 | 9/2017 | Soni |
| 2017/0258754 A1 | 9/2017 | Soni |
| 2017/0258755 A1 | 9/2017 | Soni |
| 2017/0273928 A1 | 9/2017 | Yokoyama |
| 2017/0304249 A1 | 10/2017 | Abu-Baker |
| 2017/0333377 A1 | 11/2017 | Mason |
| 2017/0348268 A1 | 12/2017 | Kimura |
| 2017/0348273 A1 | 12/2017 | Ito |
| 2017/0368184 A1 | 12/2017 | Ito |
| 2018/0015038 A1 | 1/2018 | Ito |
| 2018/0015071 A1 | 1/2018 | Braeckman et al. |
| 2018/0028480 A1 | 2/2018 | Mason |
| 2018/0042880 A1 | 2/2018 | Osterloh et al. |
| 2018/0042883 A1 | 2/2018 | Manku et al. |
| 2018/0064676 A1 | 3/2018 | Zakrzewski |
| 2018/0085334 A1 | 3/2018 | Soni |
| 2018/0153846 A1 | 6/2018 | Soni |
| 2018/0185320 A1 | 7/2018 | Manku et al. |

FOREIGN PATENT DOCUMENTS

| | | |
|---|---|---|
| CA | 2675836 | 7/2008 |
| CA | 2724983 | 11/2009 |
| CN | 101252837 | 8/2008 |
| EP | 273708 | 7/1988 |
| EP | 277747 | 8/1988 |
| EP | 0302482 | 2/1989 |
| EP | 347509 | 12/1989 |
| EP | 0460917 | 12/1991 |
| EP | 606012 | 7/1994 |
| EP | 0610506 | 8/1994 |
| EP | 0641562 A1 | 3/1995 |
| EP | 1125914 | 8/2001 |
| EP | 1157692 | 11/2001 |
| EP | 1296670 | 4/2003 |
| EP | 1549299 | 12/2003 |
| EP | 1743644 | 1/2007 |
| EP | 1 790 339 A1 | 5/2007 |
| EP | 1 834 639 A1 | 9/2007 |
| EP | 1 982 710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2719382 A1 | 4/2014 |
| EP | 2792746 | 10/2014 |
| FR | 2635263 | 9/1990 |
| GB | 2148713 | 6/1985 |
| GB | 2221843 | 2/1990 |
| GB | 2229363 | 9/1990 |
| GB | 9901809.5 | 1/1999 |
| GB | 2480146 | 11/2011 |
| IL | 55227 | 12/1982 |
| JP | 61035356 | 2/1986 |
| JP | 04182426 | 6/1992 |
| JP | 2003306690 | 10/2003 |
| JP | 07 238598 | 9/2007 |
| JP | 08 050367 | 3/2008 |
| KR | 10-2006-0109988 | 10/2006 |
| KR | 10-2007-0058460 | 6/2007 |
| RU | 2402326 C1 | 10/2010 |
| WO | WO 1990/004391 | 5/1990 |
| WO | WO 1992/021335 | 12/1992 |
| WO | WO 1994/028891 | 12/1994 |
| WO | WO 1995/024459 | 9/1995 |
| WO | WO 1996/036329 | 11/1996 |
| WO | WO 1997/039759 | 10/1997 |
| WO | WO 1998/016216 | 4/1998 |
| WO | WO 1999/26583 | 6/1999 |
| WO | WO 1999/029316 | 6/1999 |
| WO | WO 2000/044361 | 8/2000 |
| WO | WO 2000/051573 | 9/2000 |
| WO | WO 2001/015552 | 3/2001 |
| WO | WO 2002/002105 | 1/2002 |
| WO | WO 2002/058793 | 8/2002 |
| WO | WO 2002/089787 | 11/2002 |
| WO | WO 2002/096408 | 12/2002 |
| WO | WO 2003/068216 | 8/2003 |
| WO | WO 2004/050913 | 6/2004 |
| WO | WO 2004/064716 | 8/2004 |
| WO | WO 2004/078166 | 9/2004 |
| WO | WO 2004/082402 | 9/2004 |
| WO | WO 2005/060954 | 7/2005 |
| WO | WO 2005/079797 | 9/2005 |
| WO | WO 2005/079853 | 9/2005 |
| WO | WO2005/102301 | 11/2005 |
| WO | WO 2005/123060 | 12/2005 |
| WO | WO 2005/123061 | 12/2005 |
| WO | WO 2006/017627 | 2/2006 |
| WO | WO 2006/029577 | 3/2006 |
| WO | WO 2006/062748 | 6/2006 |
| WO | WO 2006/096806 | 9/2006 |
| WO | WO 2007/011886 | 1/2007 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/091338 | 8/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/088415 | 7/2008 |
| WO | WO 2008/106787 | 9/2008 |
| WO | WO 2008/115529 | 9/2008 |
| WO | WO 2008/145170 | 12/2008 |
| WO | WO 2009/004999 | 1/2009 |
| WO | WO2009/085386 | 7/2009 |
| WO | WO2009/085388 | 7/2009 |
| WO | WO 2010/028067 | 3/2010 |
| WO | WO 2010/093634 | 8/2010 |
| WO | WO 2010/127099 | 11/2010 |
| WO | WO 2010/127103 | 11/2010 |
| WO | WO 2010/147994 | 12/2010 |
| WO | WO2011/028689 | 3/2011 |
| WO | WO 2011/038122 | 3/2011 |
| WO | WO2011/085211 | 7/2011 |
| WO | WO 2011/109724 | 9/2011 |
| WO | WO 2012/074930 | 6/2012 |
| WO | WO2012/128587 | 9/2012 |
| WO | WO 2013/070735 | 5/2013 |
| WO | WO2013/103958 | 7/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO 2014/057522 | 4/2014 |
| WO | WO2014/074552 | 5/2014 |
| WO | WO2014/130200 | 8/2014 |
| WO | WO2014/134466 | 9/2014 |
| WO | WO2014/143469 | 9/2014 |
| WO | WO2014/143523 | 9/2014 |
| WO | WO2015/021141 | 2/2015 |
| WO | WO2015/066512 | 5/2015 |
| WO | WO2015/195662 | 12/2015 |
| WO | WO2016/140949 | 9/2016 |

OTHER PUBLICATIONS

National Kidney Foundation, "Glomerular Filtration Rate (GFR)," Jan. 30, 2017 (Jan. 30, 2017), retrieved on Jul. 30, 2018 from

(56) References Cited

OTHER PUBLICATIONS https://web/archive.org/web/20170130183218/https://www.kidney.org/atoz/content/gfr; entire document, especially p. 1 paragraph 1 and p. 3, paragraph 2.

Wikipedia, "Ethyl eicosapentaenoic acid," Apr. 1, 2016 (Apr. 1, 2016); retrieved on Jul. 27, 2018 from https://en.wikipedia.org/w/index.php?title=Ehtyl_eicosapentaenoic_acid&oldid=713086755; entire document, especially p. 1, col. 2 and p. 3, paragraph 2.

Wikipedia, "Diabetes mellitus," Dec. 12, 2016 (Dec. 12, 2016), retrieved on Jul. 30, 2018 from https://en.wikipedia.org/w/index.php?title=Diabetes_mellitus&oldid=754431573; entire document, especially p. 1, paragraph 1.

Amarin Corporation, Globe Newsire press release, "Reduce-It™ Cardiovascular Outcomes Study of Vascepa® (icosapent ethyl) Capsules Met Primary Endpoint," Sep. 24, 2018 (4 pages).

A study of AMR101 to evaluate its ability to reduce cardiovascular events in high risk patients with hypertriglyceridemia and on statin (REDUCE-IT). Available at: http://clinicaltrials.gov/show/NCT01492361. (3 pages).

Aarsland, et al., "On the Effect of Peroximsomal beta-Oxidation and Carnitine Palmitoyltransferase Activity by Eicosapentaenoic Aid in Live and Heart of Rats." Lipids, 25:546-548, (Sep. 1990).

Aas, V., et al., "Eicosapentaenoic acid (20:5 n-3) increases fatty acid and glucose uptake in cultured human skeletal muscle cells." Journal of Lipid Research, 47:366-374 (Feb. 2006).

Abbey, M., et al., "Effect of fish oil on lipoproteins, lecithin:cholesterol acyltransferase, and lipidtransfer protein activity in humans." Arterioscler. Thromb. Vasc. Biol. 10:85-94 (Jan./Feb. 1990).

Abele GS, Aziz K. "Cholesterol crystals cause mechanical damage to biological membranes: a proposed mechanism of plaque rupture and erosion leading to arterial thrombosis." Clin. Cardiol. (Sep. 2005);28(9):413-420.

Abelo A, Andersson TB, Antonsson M, et al. "Stereoselective metabolism of omeprazole by human cytochrome P450 enzymes." Drug Metab. Dispos. Aug. 28, 2000 (8): 966-72.

Ackman et al., "The 'Basic' Fatty Acid Composition of Atlantic Fish Oils: Potential Similarties Useful for Enrichment of Polyunsaturated Fatty Acids by Urea Complexation," JAOCS, vol. 65, 1:136-138 (Jan. 1988).

Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (Jan. 1999).

Adan, Y., et al., "Concentration of serum lipids and aortic lesion size in female and male apo E-deficient mice fed docosahexaenoic acid." Biosci. Biotechnol. Biochem. 63(2):309-313 (Feb. 1999).

Adorini et al., "Farnesoid X receptor targeting to treat nonalcoholic steatohepatitis," Drug Discover Today, 14(17-18):988-997 (Sep. 2012).

Agren JJ, Vaisanen S, Hanninen O, et al. "Hemostatic factors and platelet aggregation after a fish-enriched diet or fish oil or docosahexaenoic acid supplementation." Prostaglandins Leukot Essent Fatty Acids (Oct. 1997) 57 (4-5): 419-21.

Agren, J.J., et al., "Fatty acid composition of erythrocyte, platelet, and serum lipids in strict vegans." Lipids 30:365-369 (Apr. 1995).

Agren, J.J., et al., "Fish diet, fish oil and docosahexaenoic acid rich oil lower fasting and postprandial plasma lipid levels." Eur J Clin Nutr., 50:765-771. (Nov. 1996).

Aguilar-Salinas et al., "High Prevalence of Low HDL Cholesterol Concentrations and Mixed Hyperlipidemia in a Mexican Nationwide Survey," J Lipid Res., (Aug. 2001), 42:1298-1307.

Ai M, Otokozawa S, Asztalos BF, Ito Y, Nakajima K, White CC, Cupples LA, Wilson PW, Schaefer EJ. "Small dense LDL cholesterol and coronary heart disease: results from the Framingham Offspring Study." Clin. Chem. (Jun. 2010);56(6):967-976.

Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (Feb. 2003).

Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (Oct. 1989).

Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (Jan. 2008).

Allard et al. "Nutritional assessment and hepatic fatty acid composition in non-alcoholic fatty liver disease (NAFLD): a cross-sectional study." J Hepatol. Feb. 2008;48(2):300-7.

Allred, C., et al., "PPARγ1 as a molecular target of eicosapentaenoic acid in human colon cancer (HT-29) cells." J. Nutr. 138:250-256 (Feb. 2008).

Almeida et al., "Effect of nebicapone on the pharmacokinetics and pharmacodynamics of warfarin in healthy subjects." Eur J Clin Pharmacol. (Oct. 2008);64(10):961-6.

Amarin Appoints Medpace as CRO for Two Phase 3 Cardiovascular Trials, published Oct. 19, 2009 (2 pages).

Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from the Internet: <http://inestor.amarincorp.com/releasedetail.cfm?ReleaseID=504380> (2 pages).

Amarin Corporation, Annual Report, Jun. 24, 2010 (245 pages total)(submitted in three parts; Part I: Cover and pp. 1-39 (81 pages); Part II: pp. 40 through F-10 (81 pages); Part III: pp. F11-F51 (83 pages)).

Amarin Corporation, Executive Informational Overview, "Neurological Disease-Focused Biopharmaceutical Opportunity," SEC filing dated Oct. 11, 2005 (99 pages).

Amarin Corporation, press release (Jan. 18, 2008)(1 page).

Amarin Presentation "Next Generation Lipid Modification in Cardiovascular Disease," (Aug. 2011)(27 pages).

Amarin Presentation "Next Generation Lipid Modification in Cardiovascular Disease," (Mar. 2010)(25 pages).

Amarin Proceeding to Phase 3 with AMR101 for Hypertriglyceridemia, published Jul. 23, 2008 (1 page).

Amarin's Vascepa® Briefing Document for the Endocrinologic and Metabolic Drugs Advisory Committee Meeting dated Oct. 16, 2013, (117 pages).

Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis*. Aug. 1996;124(2):261-271.

Anderson TJ, Gregoire J, Hegele RA, et al. 2012 update of the Canadian Cardiovascular Society guidelines for the diagnosis and treatment of dyslipidemia for the prevention of cardiovascular disease in the adult. Can. J. Cardiol. Feb. 2013;29:151-167.

Anderson TJ, Meredith IT, Yeung AC, Frei B, Selwyn AP, Ganz P. The effect of cholesterol-lowering and antioxidant therapy on endothelium-dependent coronary vasomotion. N. Engl. J. Med. Feb. 1995;332:488-493.

Anderson, "Lipoprotein-Associated Phospholipase A2: An Independent Predictor of Coronary Artery Disease Events in Primary and Secondary Prevention," 101 Am. J. Cardiology 23F-33F (Jun. 2008).

Ando, M., et al., "Eicosapentanoic acid reduces plasma levels of remnant lipoproteins and prevents in vivo peroxidation of LDL in dialysis patients." J. Am. Soc. Nephroi., 10:2177-2184 (Oct. 1999).

Ando, Y., et al., "Positional distribution of highly unsaturated fatty acids in triacyl-sn-glycerols of Artemia Nauplii enriched with docosahexaenoic acid ethyl ester." Lipids 36:733-740 (Jul. 2001).

Andrade, SE. et al., "Discontinuation of antihyperlipidaemic drugs_ do rates reported in clinical trials reflect rates in primary care settings?" New Eng. J. Med. 332: 1125-1131. (Apr. 1995).

Andrews HE, Bruckdorfer KR, Dunn RC, Jacobs M. Low-density lipoproteins inhibit endotheliumdependent relaxation in rabbit aorta. Nature. May 1987;327:237-239.

(56) References Cited

OTHER PUBLICATIONS

Angerer et al., "n-3 Polyunsaturated Fatty Acids and the Cardiovascular System", Current Opinion in Lipidology, 11(1):57-63, (Feb. 2000).
Anil, Eliz, "The Impact of EPA and DHA on Blood Lipids and Lipoprotein Metabolism: Influence of ApoE Genotype", Proceedings of the Nutrition Society, 66:60-68, (Feb. 2007).
Annex to Rule 161 Response dated Apr. 16, 2012 (4 pages).
Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).
Appendix A to Defendants' Invalidity Contentions, 3:14-CV-02550-MLC-DEA (D.N.J.), 478 pages (Dec. 5, 2014).
Appleton, Katherine M., et al., "Effects of n-3 long-chain polyunsaturated fatty acids on depressed mood: systematic review of published trials", Am. J. Clin. Nutr., 84(6):1308-1316, (Dec. 2006).
Arca et al., "Treating statin-intolerant patients," Diabetes, Metabolic Syndrome and Obesity: Targets and Therapy, 4:155-156 (Apr. 28, 2011).
Arrol, S. et al., "The effects of fatty acids on apolipoprotein B secretion by human hepatoma cells (HEP G2)," Atherosclerosis 150:255-264. (Jun. 2000).
Arshad, A. et al., "Sudden cardiac death and the role of medical therapy." Progress in Cardiovascular Diseases, vol. 50, No. 6, 420-438, (May/Jun. 2008).
Arterburn, L., et al., "Distribution, interconversion, and dose response of n-3 fatty acids in humans." Am J Clin Nutr., 83:1467S-76S (Jun. 2006).
Asahara, EPA Products What is the Clinical Significance of Epadel? Obesity and Diabetes 10(6):903-905 (2011) (with English translation).
Asano, M., et al., "Eicosapentaenoic acid inhibits vasopressin-activated Ca2q influx and cell proliferation in rat aortic smooth muscle cell lines." European Journal of Pharmacology 379:199-209 (Aug. 1999).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (Apr. 1997).
Ascenta Health "Fish Oil as Triglycerides vs. Ethyl Esters: Why this Matters." (2015)(14 pages).
Atorvastatin Package Leaflet, Reg. No. LSR-005205/08, Sep. 30, 2016 [retrieved Sep. 30, 2016] retrieved from the internet: academ-clinic.ru/drugs/atorvastatin (6 pages).
ATP III guidelines, NIH publication No. 01-3305 (2001).(6 pages).
Attie AD, et al., "Relationship between stearoyl-CoA desaturase activity and plasma triglycerides in human and mouse hypertriglyceridemia," J. Lipid Res. 2002;43:1899-907.
Ault, "Prescription omega-3 fatty acid formulation approved," Ob.Gyn.News, (Jan. 15, 2005).
Avandia [package insert]. Research Triangle Park, NC: GlaxoSmithKline; 2011.(45 pages).
Avery et al., "Upper Gastrointestinal System," Integrating Therapeutic and Complementary Nutrition, Edited by Mary Marian, CRC Press (2006)(14 pages).
Aviram M, Rosenblat M, Bisgaier CL, Newton RS. Atorvastatin and gemfibrozil metabolites, but not the parent drugs, are potent antioxidants against lipoprotein oxidation. Atherosclerosis. Jun. 1998; 138(2):271-280.
Ayton, et al., "A pilot open case series of Ethyl-EPA supplementation in the treatment of anorexia nervosa," Prostaglandins, Leukotrienes and Essential Fatty Acids 71, pp. 205-209. (Oct. 2004).
Ayton, et al., "Rapid improvement of severe anorexia nervosa during treatment with ethyl-eicosapentaenoate and micronutrients," European Psychiatry 19, pp. 317-319. (Aug. 2004).

Baigent, C., et al., "Efficacy and safety of cholesterol-lowering treatment: prospective meta-analysis of data from 90,056 participants in 14 randomised trials of statins." Lancet; 366:1267-1278. (Oct. 2005).
Baldwin RM, Ohlsson S, Pedersen RS, et al. Increased omeprazole metabolism in carriers of the CYP2C19*17 allele; a pharmacokinetic study in healthy volunteers. Br. J. Clin. Pharmacol. May 2008 65 (5): 767-74.
Baldwin SJ, Clarke SE, Chenery RJ. Characterization of the cytochrome P450 enzymes involved in the in vitro metabolism of rosiglitazone. Br. J. Clin. Pharmacol. Sep. 1999;48:424-432.
Balk, E.M., et al., "Effects of omega-3 fatty acids on serum markers of cardiovascular disease risk: a systematic review. Atherosclerosis." 189:19-30. (Nov. 2006).
Ballantyne CM, Bays HE, Kastelein JJ, et al. Efficacy and safety of eicosapentaenoic acid ethyl ester (AMR 101) therapy in statin-treated patients with persistent high triglycerides (from the ANCHOR study). Am J Cardiol Oct. 2012 110 (7): 984-92.
Ballantyne et al., "Abstract 15071: AMR101 Lowers Triglycerides, Atherogenic Lipoprotein, Phospholipase $A_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.
Ballantyne et al., "Effects of icosapent ethyl on lipoprotein particle concentration and the fatty acid desaturation index in statiotreated patients with persistent high triglycerides (the ANCHOR study)." Journ. Clin. Lipidology, 2013, 7(3):270-271.
Ballantyne et al., Influence of low-high density lipoprotein cholesterol and elevated triglyceride on coronary heart disease events and response to simvastatin therapy in 4S, Circulation, 104:3046-3051. (Dec. 2001).
Bang HO, Dyerberg J. "Plasma lipids and Lipoproteins in Greenlandic west coast Eskimos" Acta Med Scand, 192:85-94. (Jul./Aug. 1972).
Bangs, A., et al., "Adiponectin translation is increased by the PPARγ agonists pioglitazone and ω-3 fatty acids." Am J Physiol Endocrinol Metab 296:480-489 (Mar. 2009).
Bangham et al., "Diffusion of univalent ions across the lamellae of swolloen phospholipids." J. Mol. Biol. (Aug. 1965) 13(1):238-252.
Bansal S, Buring JE, Rifai N, Mora S, Sacks FM, Ridker PM, "Fasting Compared With Nonfasting Triglycerides and Risk of Cardiovascular Events in Women," JAMA, 298:309-316 (Jul. 2007).
Barter et al., "Effectiveness of Combined Statin Plus Omega-3 Fatty Acid Therapy for Mixed Dyslipidemia." Am. J. Cardiol. 102(8)1040-1045 (Oct. 15, 2008).
Basu, A. et al., "Dietary Factors That Promote or Retard Inflammation." Arterioscler. Thromb. Vasc. Biol. 26:995-1001 (May 2006).
Baynes JW. Role of oxidative stress in development of complications in diabetes. Diabetes. Apr. 1991;40(4):405-412.
Bays HE et al. "Prescription omega 3 fatty acids and their lipid effects: physiologic mechanisms of action and clinical implications," Expert Rev Cardiovasc Ther., 6:391-409. (Mar. 2008).
Bays HE, Ballantyne CM, Braeckman RA, Stirlen WG, Soni PN. Icosapent ethyl, a pure ethyl ester of eicosapentaenoic acid: effects on circulating markers of inflammation from the Marine and Anchor studies. Am. J. Cardiovasc. Drugs. Feb. 2013;13(1):37-46.
Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. Nov./Dec. 2012;6:565-572.
Bays HE, Safety considerations with omega-3 fatty acid therapy. Am. J. Cardiol. Mar. 2007 99 (6A): 35C-43C.
Bays, H., Clinical Overview of Omacor: A Concentrated Formulation of Omega-3 Polyunsaturated Fatty Acids, Am J Cardiol.; 98[suppl]:71i-76i (Aug. 2006).
Bays, H., "Rationale for Prescription Omega-3-Acid Ethyl Ester Therapy for Hypertriglyceridemia: A Primer for Clinicians," Drugs of Today, 44(3); 205-246. (Mar. 2008).
Bays, H.E., Eicosapentaenoic Acid Ethyl Ester (AMR101) Therapy in Patients With Very High Triglyceride Levels (from the Multicenter, plAcebo-controlled, Randomized, double-blINd, 12-week study with an open-label Extension [MARINE] Trial) Am J Cardiol;108:682-690. (Sep. 2011).

(56) References Cited

OTHER PUBLICATIONS

Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (Apr. 2010).

Beal, M.F., Annals of Neurology, vol. 38, No. 3, "Aging, Energy, and Oxidative Stress in Neurodegenerative Diseases", pp. 357-366, (Sep. 1995).

Beaumont et al., Design of Ester Prodrugs to Enhance Oral Absorption of Poorly Permeable Compounds: Challenges to the Discovery Scientist, Current Drug and Metabolism. (Dec. 2003) 4:461-485.

Belarbi et al., "A process for high yield and scaleable recovery of high purity eicosapentaenoic acid esters from microalgae and fish oil," Enzyme and Microbail Technology 26:516-529 (Apr. 2000).

Belger et al., "Assessment of prefrontal activation by infrequent visual targets and non-target noval stimuli in schisophrenia: a function MRI study, " Presented at the 9th Biennial winter workshop on schizophrenia, Davos, Switzerland, Feb. 7-13, 1998, Abstract in Schizophrenia Research. vol. 29. No. 1/02, Jan. 1998.

Belikov, Pharmaceutical Chemistry in Two Parts, 1/General Pharmaceutical Chemistry 43-47 (1993) (with English translation)(9 pages).

Belmaker et al., "Addition of Omega-3 Fatty Acid to Maintenance Medication Treatment for Recurrent Unipolar Depressive Disorder," Am. J. Psychiatry, 159:477-479 (Mar. 2002).

Belmaker, et al., "Omega-3 Eicosapentaenoic Acid in Bipolar Depression: Report of a Small Open-Label Study," J Clin Psychiatry; 66:726-729. (Jun. 2005).

Bender NK, Kraynak MA, Chiquette E, et al. Effects of marine fish oils on the anticoagulation status of patients receiving chronic warfarin therapy. J. Thromb. Thrombolysis Jul. 5, 1998 (3): 257-61.

Beénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (Oct. 1996).

Benn et al., Improving Prediction of Ischemic Cardiovascular Disease in the General Population Using Apolipoprotein B: The Copenhagen City Heart Study, 27 Arteriosclerosis, Thrombosis, & Ascular Biology 661 (Mar. 2007).

Bennett et al., "Treatment of IgA nephropathy with eicosapentanoic acid (EPA): a two-year prospective trial [Abstract Only]." Clin. Nephrol. 31(3):128-131 (Mar. 1989).

Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (Oct. 1999).

Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89.

Berliner JA, Watson AD. A role for oxidized phospholipids in atherosclerosis. N. Engl. J. Med. Jul. 2005;353(1):9-11.

Bertelsen M, Anggard EE, Carrier MJ. Oxidative stress impairs insulin internalization in endothelial cells in vitro. Diabetologia. May 2001;44(5):605-613.

Betteridge, D.J., "Diabetic dyslipidaemia: past, present and future." Practical Diabetes Int, 21(2): 78-85. (Mar. 2004).

Bild et at., "Multi-Ethnic Study of Atherosclerosis: objectives and design," Am J . Epidemiol 156(9):871-81 (Nov. 1, 2002).

Black et al., "Effect of intravenous eicosapentaenoic acid on cerebral blood flow, edema, and brain prostaglandins in ischemic gerbils", Prostaglandins, 28(4), pp. 545-546. (Oct. 1984).

Blankenhorn D.H. et al., "Beneficial effects of combined colestipol-niacin therapy on coronary atherosclerosis and coronary venous bypass grafts." JAMA 257: 3233-3240. (Jun. 1987).

Block, R. C., et al., "EPA and DHA in blood cell membranes from acute coronary syndrome patients and controls." Atherosclerosis, 197(2):821-828 (Apr. 2008).

Blumenthal, Advanced Studies in Medicine, 2:148-157 (2002).

Boden WE, Probstfield JL, Anderson T, Chaitman BR, Desvignes-Nickens P, Koprowicz K, IJ McBride R, Teo K, Weintraub W. and the Aim-High Investigators, "Niacin in patients with low hdl cholesterol levels receiving intensive statin therapy," N. Engl. J. Med. Dec. 2011;365:2255-2267.

Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (Jun. 1992).

Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008).

Borchman D, Lamba OP, Salmassi S, Lou M, Yappert MC. The dual effect of oxidation on lipid bilayer structure. Lipids. Apr. 1992;27(4):261-265.

Bordin et al., "Effects of fish oil supplementation on apolipoprotein B100 production and lipoprotein metabolism in normolipidaemic males," Eur. J. Clin. Nutr. 52: 104-9 (Feb. 1998).

Borow et al., "Biologic plausibility, cellular effects, and molecular mechanisms of eicosapentaenoic acid (EPA) in atherosclerosis," Atherosclerosis, 242(1):357-66 (Sep. 2015).

Borthwick et al., "The effects of an omega-3 ethyl ester concentrate on blood lipid concentrations in pateitns with hyperlipidemia," Clin. Drug Investig. (1998) 15(5): 397-404.

Bossaller C, Habib GB, Yamamoto H, Williams C, Wells S, Henry PD. Impaired muscarinic endothelium-dependent relaxation and cyclic guanosine 5'-monophosphate formation in atherosclerotic human coronary artery and rabbit aorta. J. Clin. Invest. Jan. 1987;79:170-174.

Bousserouel, S., et al., "Different effects of n-6 and n-3 polyunsaturated fatty acids on the activation of rat smooth muscle cells by interleukin-1 beta." J. Lipid Res. 44:601-611 (Mar. 2003).

Bousserouel, S., et al., "Modulation of cyclin D1 and early growth response factor-1 gene expression in interleukin-1 beta-treated rat smooth muscle cells by n-6 and n-3 polyunsaturated fatty acids." Eur. J. Biochem. 271:4462-4473 (Nov. 2004).

Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(Jun. 2004).

Braeckman et al., "Abstract 18549: Effects of AMR101, a Pure Eicosapentaenoic Omega-3 Fatty Acid, on the Fatty Acid Profile in Plasma and Red Blood Cells in Statin-Treated Patients with Persistent High Triglycerides—Results from the ANCHOR study," Circulation 126(21S):A15071 (Nov. 20, 2012)(2 pages).

Braeckman et al., "Effect of Concomitant Icosapent Ethyl (Eicosapentaenoic Acid Ethyl Ester) on Pharmacokinetics of Atorvastatin," Clinical Drug Investigation. (Jan. 2015) (3)45-51.

Braeckman RA, Manku MS, Bays HE, Stirtan WG, Soni PN. Icosapent ethyl, a pure EPA omega-3 fatty acid: effects on plasma and red blood cell fatty acids in patients with very high triglyceride levels (results from the MARINE study). Prostaglandins Leukot Essent Fatty Acids. Sep. 2013;89(4):195-201.

Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.

Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. 2013;3:101-108.

Braunersreuther V, Steffens S, Arnaud C, Pelli G, Burger F, Proudfoot A, Mach F. A novel rantes antagonist prevents progression of established atherosclerotic lesions in mice. Arterioscler. Thromb. Vasc. Biol. Jun. 2008;28:1090-1096.

Breslow, J., "n-3 Fatty acids and cardiovascular disease." Am J Clin Nutr., 83:1477S-82S (Jun. 2006).

(56) References Cited

OTHER PUBLICATIONS

Brinton EA, Ballantyne CM, Bays HE, Kastelein JJ, Braeckman RA, Soni PN. Effects of AMR101 on lipid and inflammatory parameters in patients with diabetes mellitus-2 and residual elevated triglycerides (200-500 mg/dl) on statin therapy at LDL-C goal: the ANCHOR study.[abstract 629-P] Diabetes. 2012;61(suppl 1):A159-A160.
Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (Oct. 1996).
Brouwer, I.A., et al., "Effect of fish oil on ventricular tachyarrhythmia and death in patients with implantable cardioverter defibrillators." JAMA. 295(22):2613-2619 (Jun. 2006).
Brovkovych V, Dobrucki LW, Brovkovych S, Dobrucki I, Do Nascimento CA, Burewicz A, Malinski T. Nitric oxide release from normal and dysfunctional endothelium. J. Physiol. Pharmacol. Dec. 1999;50:575-586.
Brown et al., Simvastatin and Niacin, Antioxidant Vitamins, or the Combination for the Prevention of Coronary Disease, N Engl J Med, vol. 345, No. 22, 1583-1592 (Nov. 29, 2001).
Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (Jan. 1999).
Brown, A. J., et al., "Persistent changes in the fatty acid composition of erythrocyte membranes after moderate intake of n-3 polyunsaturated fatty acids: study design and implications." Am.J. Clin. Nutri. 54:668-73(Oct. 1991).
Brown, G., et al., "Regression of coronary artery-disease as a result of intensive lipid-lowering therapy in men with high levels of apolipoprotein," B., N. Engl. J. Med. 323: 1289-1298. (Nov. 1990).
Brownlee M. Biochemistry and molecular cell biology of diabetic complications. Nature. Dec. 2001; 414(6865):813-820.
Bryhn, M., et al., "The bioavailability and pharmacodynamics of different concentrations of omega-3 acid ethyl esters." Prostaglandins, Leukotrienes and Essential Fatty Acids 75:19-24 (Jul. 2006).
Budavari, S., Editor, "The Merck Index", Merck & Co., Inc., p. 725 item 4511 and p. 279 and item 2417 (1989).
Budoff, "Triglycerides and Triglyceride-Rich Lipoproteins in the Causal Pathway of Cardiovascular Disease," Am. J. Cardiol., 118(1):138-45 (Jul. 1, 2016).
Bunting et al. "Depression in Parkinson's Disease". J Neurosci Nurs.; 23(3):158-164. (Abstract Only) (Jun. 1991).
Burdge, G.C., et al., "Eicosapentaenoic and docosapentaenoic acids are the principal products of a-linolenic acid metabolism in young men." British Journal of Nutrition 88:355-363 (Oct. 2002).
Burdge, G.C., et al., "Lack of effect of meal fatty acid composition on postprandial lipid, glucose and insulin responses in men and women aged 50-65 years consuming their habitual diets." British Journal of Nutrition, 96:489-500 (Sep. 2006).
Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (Jul. 2007).
Burr, M. L., et al., "Effects of changes in fat, fish and fibre intakes on death and myocardial reinfarction: Diet and reinfarction trial." The Lancet, 2(8666):757-61 (Sep. 1989).
Buse JB, Ginsberg HN, Bakris GL, et al. Primary prevention of cardiovascular diseases in people with diabetes mellitus: a scientific statement from the American Heart Association and the American Diabetes Association. Diabetes Care. 2007;30: 162-172.
Calabresi, L., et al., "Omacor in familial combined hyperlipidemia: effects on lipids and low density lipoprotein subclasses." Atherosclerosis 148:387-396 (Feb. 2000).
Calder PC. The role of marine omega-3 (n-3) fatty acids in inflammatory processes, atherosclerosis and plaque stability. Mol. Nutr. Food Res. Jul. 2012;56(7)1073-1080.
Campos, H., et al., "Lowdensity lipoprotein size, pravastatin treatment, and coronary events." JAMA, 286:1468-1474 (Sep. 2001).
Canner P.L. et al., "Fifteen year mortality in Coronary Drug Project patients: long-term benefit with niacin," J. Am. Coll. Cardiol. 8. 1245-1255. (Dec. 1986).
Cao, et al., "Cloning, Expression, and Chromosomal Locatlization . . . ", Genomics, 49:327-331, (Apr. 15, 1998).
Cao, J., et al., "Incorporation and Clearance of Omega-3 Fatty Acids in Erythrocyte Membranes and Plasma Phospholipids." Clinical Chemistry 52(12):2265-2272 (Dec. 2006).
Capuzzi, DM et al., "Efficacy and safety of an extended-release niacin (Niaspan): a long-term study." Am. J. Cardiol. 82: 74U-81U. (Dec. 17, 1998).
Carlson, L.A. & Rosenhamer G., "Reduction of mortaility in the Stockholm Ischaemic Heart Disease Secondary Prevention Study by combined treatment with clofibrate and nicotinic acid." Acta Med. Scand. 223, 405-418 (1988).
Carlson, L.A., "Nicotinic acid: the broad spectrum lipid drug. A 50th Anniversary review", J. Int. Med., 258:94-114, (Aug. 2005).
Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (Feb. 2007).
Carrero, J.J. et al. "Efectos cardiovasculares de los acidos grasos omega-3 y alternatives para incrementar su ingesta," Nutricion Hospitalaria. (2005) (1) 63-69 [with English abstract].
Carroll, D. N., et al., "Evidence for the Cardioprotective Effects of Omega-3 Fatty Acids." Ann Pharmacother., 36:1950-6 (Dec. 2002).
Carulli et al., "Chenodeoxycholic acid and ursodeoxycholic acid effects in endogenous hypertriglyceridemias. A controlled double-blind trial." J. Clin. Pharmacol., 21(10):436-42 (Oct. 1981).
Cazzola, R., et al., "Age- and dose-dependent effects of an eicosapentaenoic acid-rich oil on cardiovascular risk factors in healthy male subjects." Atherosclerosis 193:159-167 (Jul. 2007).
Ceci et al., "The effects of oral 5-hydroxytryptophan administration on feeding behavior in obese adult female subjects," J Neural. Transm (1989) 76(2)109-117.
Cefali, E.A., et al., "Aspirin reduces cutaneous flushing after administration of an optimised extended-release niacin formulation", Int. J. Clin. Pharmacol. & Ther., 45(2):78-88, (Feb. 2007).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/0218535000;%20021654s016_StatR.pdf. (Accessed Jan. 26, 2012) (156 pages).
Center for Drug Evaluation and Research. Approval Package for Application No. 202057Orig1s000. Review—Vascepa (formerly AMR101), 373 pages (Jul. 26, 2012)(in two parts).
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_0macor_AdminCorres_P1.pdf. Accessed Jan. 26, 2012. (54 pages).
Ceriello A, Motz E. Is oxidative stress the pathogenic mechanism underlying insulin resistance, diabetes, and cardiovascular disease? The common soil hypothesis revisited. Arterioscler. Thromb. Vasc. Biol. (May 2004);24(5):816-823.
Chait A, Brazg RL, Tribble DL, Krauss RM. Susceptibility of small, dense, low-density lipoproteins to oxidative modification in subjects with the atherogenic lipoprotein phenotype, pattern B. Am. J. Med. (Apr. 1993);94(4):350-356.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan et al., Factorial Study of the Effects of Atorvastatin and Fish Oil on Dyslipidaemia in Visceral Obesity, 32 Euro. J. Clinical Investigation. 32(6):429-36 (Jun. 2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J., 31(2):149-164 (Jan. 2010).

(56) References Cited

OTHER PUBLICATIONS

Chatterjee SN, Agarwal S. Liposomes as membrane model for study of lipid peroxidation. Free Radic. Biol. Med. 1988;4(1):51-72.
Chemical Book, Eicosapentaenoic acid ethyl ester, copyright 2010, printed Jun. 16, 2011 from www.chemicalbook.com. (2010).
Chen, H., et al., "Eicosapentanoic acid inhibits hypoxia-reoxygenation-induced injury by attenuating upregulation of MMP-1 in adult rat myocytes." Cardiovascular Research 59:7-13 (Jul. 2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (Jul. 2003).
Chen, I.S., et al., "In vitro clearance of chylomicron triglycerides containing (ω-3) eicosapentaenoate." Atherosclerosis, 65:193-198 (1987).
Cheng et al., "Antagonism of the prostaglandin D2 receptor 1 suppresses nicotinic acid-induces vasodilation in mice and humans," PNAS 103(17):6682-7 (Apr. 25, 2006).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, (Oct. 1990).
Christensen, J. H., et al., "Effect of fish oil on heart rate variability in survivors of myocardial infarction: a double blind randomised controlled trial." BMJ, 312:677-678 (Mar. 16, 1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (Jan. 1995).
Classification of Hyperlipidaemias and Hyperlipoproteinaemias, Bulletin of the World Health Organization, 43(6): 891-915 (1970).
Cleland, L.G., et al., "A Biomarker of n-3 compliance in patients taking fish oil for rheumatoid arthritis." Lipids 38:419-424 (Apr. 2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501> (3 pages).
Cohen AW, Combs TP, Scherer PE, Lisanti MP. Role of caveolin and caveolae in insulin signaling and diabetes. American journal of physiology. Endocrinology and metabolism. (Dec. 2003);285(6):E1151-1160.
Cohen, J.D., et al., "30-year trends in serum lipids among United States adults: results from the National Health and Nutrition Examination Surveys II, III, and 1999-2006." Am J Cardiol., 106:969-975. (Dec. 15, 2010).
Cole et al., "Challenges and opportunities in the encapsulation of liquid and semi-solid formulations into capsules for oral administration," Advanced Drug Delivery Reviews, vol. 60, No. 6, pp. 747-756. (Mar. 17, 2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (Aug. 21-24, 2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (Dec. 2008).
Committee Roster for the Oct. 16, 2013 Meeting of the Endocrinologic and Metabolic Drugs Advisory Committee, 2 pages. (2013).
Conklin, S. M., et al., "Serum ω-3 fatty acids are associated with variation in mood, personality and behavior in hypercholesterolemic community volunteers." Psychiatry Research 152: 1-10 (Jul. 30, 2007).
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (Jan. 2000).
Conquer, J.A., et al., "Effect of supplementation with different doses of DHA on the levels of circulating DHA as non-esterified fatty acid in subjects of Asian Indian background. J Lipid Res." 39:286-292. (Feb. 1998).
Conquer, J.A., et al., "Supplementation with an algae source of docosahexaenoic acid increases (n-3) fatty acid status and alters selected risk factors for heart disease in vegetarian subjects." J Nutr., 126: 3032-3039. (Dec. 1996).
Contacos et al. Effect of pravastatin and omega-3 fatty acids on plasma lipids and lipoproteins in patients with combined hyperlipidemia, pp. 1755-1762 (Dec. 1993).
Coronary Artery Bypass Grafting, NIH, published online Feb. 23, 2012 (12 pages).
Coumadin [package insert], Princeton, NJ: Bristol-Myers Squibb; 2011. (10 pages).
Cox PJ, Ryan DA, Hollis FJ, et al. Absorption, disposition, and metabolism of rosiglitazone, a potent thiazolidinedione insulin sensitizer, in humans. Drug Metab. Dispos. Jul. 2000;28:772-780.
Creager MA, Gallagher SJ, Girerd XJ, Coleman SM, Dzau VJ, Cooke JP. L-arginine improves endothelium-dependent vasodilation in hypercholesterolemic humans. J. Clin. Invest. Oct. 1992;90:1248-1253.
Crevel et al., "Allergenicity of Refined Vegetable Oils," Food and Chemical Toxicology, 38, pp. 385-393 (Apr. 2000).
Criqui, M., "Triglycerides and Coronary Heart Disease Revisited (Again)," vol. 147 No. 6, pp. 425-427 (Sep. 18, 2007).
Cromwell et al., "LDL particle number and risk of future cardiovascular disease in the Framingham Offspring Study—Implications for LDL Management," Journal of Lipidololgy. (Dec. 2007) 1, 583-592.
Crowe, F. L., et al., "Serum phospholipid n-3 long-chain polyunsaturated fatty acids and physical and mental health in a population-based survey of New Zealand adolescents and adults." Am J Clin Nutr 86:1278-85 (Nov. 2007).
Cruz et al., "The metabolic syndrome in children and adolescents," Curr. Diab. Rep., vol. 4(1):53-62 (Feb. 2004).
Culhane et al., "Rosuvastatin for the treatment of hypercholesterolemia," Pharmacotherapy, 25(7):990-1000 (Jul. 2005).
Daggy, B. et al. Dietary fish oil decreases VLDL production rates. Biochimica et Biophysics Acta 920: 293-300 (Aug. 15, 1987).
Dall et al., "Clinical utility of low-density lipoprotein particle measurement in management of cardiovascular disease: a case report," Research Reports in Clin. Cardiol., vol. 2, pp. 57-62 (2011).
Das, U.N., Essential fatty acids as possible mediators of the actions of statins. Prostaglandins, Leukotrienes and Essential FattyAcids 65(1):37-40, (Jul. 2001).
Davidson MH, Ballantyne CM, Jacobson TA, et al. Clinical utility of inflammatory markers and advanced lipoprotein testing: advice from an expert panel of lipid specialists. J. Clin. Lipidol. Sep./Oct. 2011;5:338-367.
Davidson MH, et al., Effects of prescription omega-3-acid ethyl esters on lipo protein particle concentrations, apolipoproteins AI and CIII, and lipoprotein-associated phospholipase $A_2$ mass in statin-treated subjects with hypertrigylceridemia, J.Clin. Lipid., vol. 3(5), pp. 332-340 (Oct. 2009).
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. Jun. 2014;34:1298-1306.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (2007).
Davidson MH., "Mechanisms for the hypotriglyceridemic effect of marine omega 3 fatty acids." Am J Cardiol 98(4A):27i-33i. (2006).
Davidson, M.H., et al., "Effects of docosahexaenoic acid on serum lipoproteins in patients with combined hyperlipidemia: a randomized, doubleblind, placebo-controlled trial." J Am Coll Nutr., 16:236-243. (1997).

(56) References Cited

OTHER PUBLICATIONS

Davies et al., "Rapid separation of LDL subclasses by iodixanol gradient ultracentrifugation," Clin. Chem., 49(11):1865-72. (Nov. 2003).

Davies-Tuck et al., "Total cholesterol and triglycerides are associated with development of new bone marrow lesions in asymptomatic middle-aged women—a prospective cohort study," Arthritis Research & Therapy. (2009) pp. 1-7.

De Caterina, R, et al., "Control of Endothelial Leukocyte Adhesion Molecules by Fatty Acids." Lipids, vol. 31:S57-S63 (1996).

De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).

De Graaf J, Hak-Lemmers HL, Hectors MP, Demacker PN, Hendriks JC, Stalenhoef AF. Enhanced V susceptibility to in vitro oxidation of the dense low density lipoprotein subfraction in healthy subjects. Arterioscler. Thromb. 1991;11(2):298-306.

Deckelbaum R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).

Defendants' Invalidity Contentions, 3:14-CV-02550-MLC-DEA (D.N.J.), 520 pages (Dec. 5, 2014).

Defendants' Joint Invalidity Contentions, 3:14-CV-02550-MLC-TJB (D.N.J.), 901 pages (Dec. 5, 2014).

Dewailly, E., et al., "n-3 Fatty acids and cardiovascular disease risk factors among the Inuit of Nunavik." Am J Clin Nutr 74:464-73 (2001).

Di Spirito, M., Morelli, G., Doyle, R.T., Johnson, J. & McKenney, J. Effect of omega-3-acid ethyl esters on steady-state plasma pharmacokinetics of atorvastatin in healthy adults. Expert Opin. Pharmacother. 9, 2939-2945 (2008).

Diagnostic and Statistical Manual of Mental Disorders, 4.Ed. Text revision, published by the American Psychiatric Assoc., pp. 154-163 and 369-381 (2000).

Diagnostic and Statistical Manual of Mental Disorders, 4.sup.th Ed., published by the American Psychiatric Assoc., pp. 285-286, (1994).

Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (1996).

Dijk, J. M., et al., "Carotid intima-media thickness and the risk of new vascular events in patients with manifest atherosclerotic disease: the SMART study." European Heart Journal 27:1971-1978 (2006).

Din et al., "Omega 3 fatty acids and cardiovascular disease—fishing for a natural treatment," BMJ, vol. 327, No. 7430, pp. 30-35 (2004).

Dodin, S., et al., "Flaxseed on cardiovascular disease markers in healthy menopausal women: a randomized, double-blind, placebo-controlled trial." Nutrition 24:23-30 (2008).

Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, (1991).

Draft Agenda for the Oct. 16, 2013 Meeting of the Endocrinologic and Metabolic Drugs Advisory Committee, 2 pages.

Draft Meeting Roster for the Oct. 16, 2013 Meeting of the Endocrinologic and Metabolic Drugs Advisory Committee, 2 pages.

Draft Questions for the Oct. 16, 2013 Meeting of the Endocrinologic and Metabolic Drugs Advisory Committee, 1 page.

Drexler H, Zeiher AM, Meinzer K, Just H. Correction of endothelial dysfunction in coronary microcirculation of hypercholesterolaemic patients by !-arginine. Lancet. 1991;338:1546-1550.

Dullenmeijer, C., et al., "n-3 Fatty acid proportions in plasma and cognitive performance in older adults." Am J Clin Nutr 86:1479-85 (2007).

Duncan, R. E., et al., "Regulation of HMG-CoA reductase in MCF-7 cells by genistein, EPA, and DHA, alone and in combination with mevastatin." Cancer Letters 224:221-228 (2005).

Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001).

Dwyer, J. H., et al., "Arachidonate 5-Lipoxygenase Promoter Genotype, Dietary Arachidonic Acid, and Atherosclerosis." N. Engl. J. Med., 350:1 (2004).

Dyerberg, J., et al., "Marine Oils and Thrombogenesis." Prog. Lipid Res. 21:255-269 (1982).

Egert, S., et al., "Dietary alpha-linolenic acid, EPA, and DHA have differential effects on LDL fatty acid composition but similar effects on serum lipid profiles in normolipidemic humans." J Nutr., 139:861-868 (2009).

Ehara S, Ueda M, Naruko T, Haze K, Itoh A, Otsuka M, Komatsu R, Matsuo T, Itabe H, Takano T, Tsukamoto Y, Yoshiyama M, Takeuchi K, Yoshikawa J, Becker AE. Elevated levels of oxidized low density lipoprotein show a positive relationship with the severity of acute coronary syndromes. Circulation. 2001;103(15):1955-1960.

Eilat-Adar et al. "Association of Intentional Changes in Body Weight with Coronary Heart Disease Event Rates in Overweight Subjects who have an Additional Coronary Risk Factor," Amer. Journ. Epidemiol.161(4)pp. 352-358 (Sep. 9, 2004).

Eisenberg S, Bilheimer DW, Levy RI, Lindgren FT. "On the metabolic conversion of human plasma very low density lipoprotein to low density lipoprotein," Biochim Biophys Acta, 326:361-77 (1973).

Eisenberg S, Rachmilewitz D. "Metabolism of rat plasma very low density lipoprotein. I. Fate in circulation of the whole lipoprotein," Biochim Biophys Acta, 326:378-90 (1973).

El-Serag HB, Graham DY, Satia JA, et al. Obesity is an independent risk factor for GERD symptoms and erosive esophagitis. Am. J. Gastroenterol. Jun. 2005 100 (6): 1243-50.

Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000).

El-Saadani M, Esterbauer H, El-Sayed M, Gober M, Nassar AY, Jurgens G. A spectrophotometric assay for lipid peroxides in serum lipoproteins using commercially available reagent. J. Lipid Res. 1989;30:627-630.

El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).

Emsley et al., "Randomized, Placebo-Controlled Study of Ethyl-Eicosapentaenoic Acid as Supplemental Treatment in Schizophrenia," Am. J. Psychiatry, 159:1596-1598 (2002).

Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation)(22 pages).

ENews, "Cholesterol Crystals Induce Atherosclerosis-Associated Inflammation in Mice," 1-4 (Jun. 14, 2010)(4 pages).

Engler, et al., "Docosahexaenoic acid restores endothelial function in children with hyperlipidemia: results from the EARLY Study." International Journal of Clinical Pharmacology and Therapeutics, vol. 42—No. Dec. 2004 (672-679). (2004).

Engler, M.B., et al., "Mechanisms of vasorelaxation induced by eicosapentaenoic acid (20:5n-3) in WKY rat aorta." British Journal of Pharmacology 131:1793-1799 (2000).

Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).

Ennis JL, Cromwell WC. Clinical utility of low-density lipoprotein particles and apolipoprotein B in patients with cardiovascular risk. J. Fam. Pract. 2013;62:1-8.

Epadel—PubChem CID 9831415, Retrieved on Apr. 9, 2014 [Retrieved from the Internet] <URL:http://pubchem.ncbi.nlm.nih.gov/compound/9831415> (19 pages).

Epadel 1990 and JELIS Study (4 pages).

Epadel Capsules 300, Japan Pharmaceutical Reference 369-371 (2nd ed.) (1991). (5 pages).

(56) References Cited

OTHER PUBLICATIONS

Epadel drug information brochure (2000), certified English translation(36 pages).
Epadel Package Insert 2007 (with Translation)(6 pages).
Epadel® [Complete prescribing information]. Update (Version 5). Tokyo, Japan: Mochida Pharmaceutical; Jan. 2007 (9 pages).
EPANOVA® (omega-3-carboxylic acids) capsules, for oral use, Prescribing information, 5 pgs., AstraZeneca Pharmaceuticals LP, (Revised: Mar. 2017)(5 pages).
Eritsland J, Arnesen H, Gronseth K, et al. Effect of dietary supplementation with n-3 fatty acids on coronary artery bypass graft patency. Am. J. Cardiol. Jan. 1996 77 (1): 31-6.
Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 1995 6 (1): 17-22.
Errata to the FDA Briefing Document Endocrinologic and Metabolic Drug Advisory Committee Meeting Oct. 16, 2013, 1 page.
Esposito, "Effect of a Mediterranean-Style Diet on Endothelial Dysfunction and Markers ofVascular Inflammation in the Metabolic Syndrome: A Randomized Trial", Journal of the American Medical Association, 2004, 292(12), 1440-1446.
Essentialis Inc. press release, "Essentialis Meets Primary Endpoint in Phase 2b Trial of DCCR for Treatement of Hypertriglyceridemia and is Granted Extensive Patent Coverage in the US," PR Newswire (May 17, 2009)( 2 pages).
Exhibit A to Defendants' Joint Invalidity Contentions, 3:14-CV-02550-MLC-TJB (D.N.J.), 48 pages (Dec. 5, 2014).
Exhibit B to Defendants' Joint Invalidity Contentions, 3:14-CV-02550-MLC-TJB (D.N.J.), 6 pages (Dec. 5, 2014).
Exhibit C to Defendants' Joint Invalidity Contentions, 3:14-CV-02550-MLC-TJB (D.N.J.), 14 pages (Dec. 5, 2014).
Exhibit D to Defendants' Joint Invalidity Contentions, 3:14-CV-02550-MLC-TJB (D.N.J.), 19 pages (Dec. 5, 2014).
Exhibit E to Defendants' Joint Invalidity Contentions, 3:14-CV-02550-MLC-TJB (D.N.J.), 6 pages (Dec. 5, 2014).
Exhibit F to Defendants' Joint Invalidity Contentions, 3:14-CV-02550-MLC-TJB (D.N.J.), 10 pages (Dec. 5, 2014).
Exhibit G to Defendants' Joint Invalidity Contentions, 3:14-CV-02550-MLC-TJB (D.N.J.), 21 pages (Dec. 5, 2014).
Exhibit H to Defendants' Joint Invalidity Contentions, 3:14-CV-02550-MLC-TJB (D.N.J.), 10 pages (Dec. 5, 2014).
Exhibit Ito Defendants' Joint Invalidity Contentions, 3:14-CV-02550-MLC-TJB (D.N.J.), 14 pages (Dec. 5, 2014).
Exhibit J to Defendants' Joint Invalidity Contentions, 3:14-CV-02550-MLC-TJB (D.N.J.), 13 pages (Dec. 5, 2014).
Exhibit K to Defendants' Joint Invalidity Contentions, 3:14-CV-02550-MLC-TJB (D.N.J.), 5 pages (Dec. 5, 2014).
Exhibit L to Defendants' Joint Invalidity Contentions, 3:14-CV-02550-MLC-TJB (D.N.J.), 5 pages (Dec. 5, 2014).
Exhibit M to Defendants' Joint Invalidity Contentions, 3:14-CV-02550-MLC-TJB (D.N.J.), 7 pages (Dec. 5, 2014).
Exhibit N to Defendants' Joint Invalidity Contentions, 3:14-CV-02550-MLC-TJB (D.N.J.), 15 pages (Dec. 5, 2014).
Exhibit O to Defendants' Joint Invalidity Contentions, 3:14-CV-02550-MLC-TJB (D.N.J.), 6 pages (Dec. 5, 2014).
Exhibit P To Defendants' Joint Invalidity Contentions, 33:14-CV-02550-MLC-TJB (D.N.J.), 17 pages (Dec. 5, 2014).
Exhibit Q to Defendants' Joint Invalidity Contentions, 3:14-CV-02550-MLC-TJB (D.N.J.), 64 pages (Dec. 5, 2014).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
FDA Briefing Document, Endocrinologic and Metaboloic Drugs Advisory Committee Meeting, dated Oct. 16, 2013, available publicly at least as of Oct. 16, 2013, 115 pages.
FDA News Release, "FDA approves new orphan drug Kynamro to treat inherited cholesterol disorder," U.S. Food and Drug Administration, Protecting and Promoting Your Health (Jan. 29, 2013)(2 pages).
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Feron O, Dessy C, Desager JP, Balligand JL. Hydroxy-methylgluataryl-coenzyme a reductase inhibition promotes endothelial nitric oxide synthase activation through a decrease in caveolin abundance. Circulation. 2001;103:113-118.
Final Agenda for the Oct. 16, 2013 Meeting of the Endocrinologic and Metabolic Drugs Advisory Committee, 2 pages.
Final Meeting Roster for the Oct. 16, 2013 Meeting of the Endocrinologic and Metabolic Drugs Advisory Committee, 2 pages.
Final Questions for the Oct. 16, 2013 Meeting of the Endocrinologic and Metabolic Drugs Advisory Committee, 1 page.
Finnen et al., "Purification and characterisation of phospholipase A2 from human epidermis, ", Biochemical Society Trans,19(2):91S, 1991.
Fischer, R., et al., "Dietary n-3 polyunsaturated fatty acids and direct renin inhibition improve electrical remodeling in a model of high human renin hypertension." Hypertension 51:540-546 (2008).
Fisher et al., Journal of Biological Chemistry (2001) 276(3) 27855-27863.
Flaten, H., et al., "Fish-oil concentrate: effects on variables related to cardiovascular disease." Am. J. Clin. Nutr. 52:300-306 (1990).
Food and Drug Administration (FDA), (2005) *NIASPAN niacin extended release tablets*.
Food and Drug Administration (FDA), (2005) *Tablets ZOCOR® (SIMVASTATIN)*.
Ford, E.S. et al., "Hypertriglyceridemia and Its Pharmacologic Treatment Among US Adults." Arch, Intern. Med., 169(6): 572-78 (2009).
Frangou et al., "Efficacy of ethyl-eicosapentaenoic acid in bipolar depression: randomised double-blind placebo-controlled study," British Journ. Psychiatry, 188, 46-50 (2006).
Frey R, Muck W, Kirschbaum N, et al. Riociguat (BAY 63-2521) and warfarin: a pharmacodynamic and pharmacokinetic interaction study. J. Clin. Pharmacol. Jul. 2011 51 (7): 1051-60.
Frick, MH, et al., "Helsinki Heart Study. Primary prevention trial with gemfibrozil in middle-aged men with dyslipidaemia. Safety of treatment, changes in risk factors and incidence of coronary heart disease", N. Eng. J. Med., 317:1237-1245, (1987).
Friedewald, W.T., et al., "Estimation of the concentration of low-density lipoprotein cholesterol in plasma, without use of the preparative ultracentrifuge." Clin Chem., 18:499-502 (1972).
Friedman, A. N., et al., "Fish Consumption and Omega-3 Fatty Acid Status and Determinants in Long-Term Hemodialysis." Amer. J. Kidney Diseases, 47(6):1064-1071 (2006).
Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996).
Frøyland, L., et al., "Hypotriacylglycerolemic component of fish oil." Prostaglandins, Leukotrienes and Essential Fatty Acids 57 (4 & 5):387-388 (1997).
Furuta T, Shirai N, Sugimoto M, et al. Influence of CYP2C19 pharmacogenetic polymorphism on proton pump inhibitor-based therapies. Drug Metab. Pharmacokinet Jun. 2005 20 (3): 153-67.
Futata et al., "Effect of Eicosapentaenoic Acid (EPA) Formulation on Glucose Metabolism in Non-Insulin Dependent Diabetic Patients," Journal of Clinical and Experimental Medicine 169(8):889-890 (May 21, 1994)(English translation, 4 pages).
Galeano NF, Al-Haideri M, Keyserman F, Rumsey SC, Deckelbaum RJ. Small dense low density lipoprotein has increased affinity for LDL receptor-independent cell surface binding sites: a potential mechanism for increased atherogenicity. J. Lipid Res. 1998;39(6):1263-1273.

(56) References Cited

OTHER PUBLICATIONS

Gallagher et al., "Germline BRCA Mutations Denote a Clinicopathalogic Subset of Prostate Cancer," Amer. Assoc. Cancer Res. Clin Cancer Res., 16(7):2115-21 (2010).
Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48.
Gardner CD, Fortmann SP, Krauss RM. Association of small low-density lipoprotein particles with the incidence of coronary artery disease in men and women. JAMA. 1996;276(11):875-881.
Garg, R., et al., "Niacin treatment increases plasma homocyst(e)ine levels", Am. Heart. J., 138:1082-1087, (1999).
Garnett, "Interactions with Hydroxymethylglutaryl-coenzyme A reductase inhibitors," Am J Health-Sys Pharm vol. 52, 1639-1645, (1995).
Genest, JJ, et al., "Familial lipoprotein disorders in patients with premature coronary artery disease", 85:2025-2033, (1992).
Geppert, et al. "Microalgal docosahexaenoic acid decreases plasma triacylglycerol in normolipidaemic vegetarians: a randomized trial." British Journal of Nutrition, 95, 779-786. (2006).
Gillies, et al. "Effect of a Novel Eicosapentaenoic Acid-Rich Oil on Serum Cholesterol in Man," DuPont 2010.
Ginsberg HN, Elam MB, Lovato LC, Crouse JR, 3rd, Leiter LA, Linz P, Friedewald WT, Buse JB, Gerstein HC, Probstfield J, Grimm RH, Ismail-Beigi F, Bigger JT, Goff DC, Jr., Cushman WC, Simons-Morton DG, Byington RP. Effects of combination lipid therapy in type 2 diabetes mellitus. N. Engl. J. Med. 2010;362:1563-1574.
Ginsberg HN. "Hypertriglyceridemia: new insights and new approaches to pharmacologic therapy," Am J Cardiol, 87:1174-1180 (2001).
Girotti A W. Lipid hydroperoxide generation, turnover, and effector action in biological systems. J. Lipid Res. 1998;39(8):1529-1542.
GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, (Aug. 7, 1999).
Glod, "Recent Advances in the Pharmacotherapy of Major Depression", Arch. Psychiatr. Nurs., 10(6):355-364 (Dec. 1996).
Goldberg, A C: "Combination therapy of dyslipidemia," Current Treatment Options in Cardiovascular Medicine Aug. 2007 GB, vol. 9, No. 4, pp. 249-258 (2007).
Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001)(32 pages).
Gordon, DJ. et al., High density lipoprotein cholesterol and cardiovascular disease: four prospective American studies. Circulation. 79: 8-15. (1989).
Gorriz JL et al., "Rhabdomyolysis and Acute Renal Failure Associated with Gemfibrozil Therapy," Nephron 74(2): 437-438 (1996).
Gorriz, JL, "Rhabdomyolysis and Acute Renal Failure Associated with Bezafibrate Treatment," Nephrol Dial Transplant 10(12):2371-2372 (1995).
Gosai, P. et al. Effect of omega-3-acid ethyl esters on the steady-state plasma pharmacokinetics of rosuvastatin in healthy adults. Expert Opin. Pharmacother. 9, 2947-2953 (2008).
Goto, Y. et al., "Clinical Pharmacological Trial of Ethyl Icosapentate (MND-21)-Dose Finding Study." Journal of Clinical Therapeutic & Medicines 8:1293-309 (1992).
Gould, A.L., et al., "Cholesterol reduction yields clinical benefit: impact of statin trials." Circulation, 97:946-952 (1998).
Greenblatt DJ, von Moltke LL. Interaction of warfarin with drugs, natural substances, and foods. J. Clin. Pharmacol. Feb. 2005 45 (2): 127-32.
Grenyer, Brin F.S., et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007).
Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).
Grimsgaard et al., "Effects of Highly Purified Eicosapentaenoic Acid and Docosahexaenoic Acid on Hemodynamics in Humans" American Society for Clinical Nutrition, 68:52-9, (1998).
Grimsgaard, Kaare H. Bonaa, John-Bjarne Hansen, and Arne Nordoy, "Highly purified eicosapentaenoic acid and docosahexaenoic acid in humans have similar triacylglycerol-lowering effects but divergent effects on serum fatty acids" Am J Clin Nutr, 66:649-659, (1997).
Grundy S.M et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002).
Grundy SM, et al. Implications of Recent Clinical Trials for the National Cholesterol Education Prgram Adult Treatment Panel III Guidelines, Circulation. 2004; 110:227-39.
Grundy, Scott M., "Low-Density Lipoprotein, Non-High-Density Lipoprotein, and Apolipoprotein B as Targets of Lipid-Lowering Therapy" Circulation. 106:2526-2529 (2002).
Guallar, E., et al., "Omega-3 fatty acids in adipose tissue and risk of myocardial infarction—The EURAMIC study." Arterioscler. Thromb. Vasc. Biol., 19:1111-1118 (1999).
Guillot, et al., "Increasing intakes of the long-chain omega-3 docosahexaenoic acid: effects on platelet functions and redox status in healthy men," The FASEV Journal, vol. 23, pp. 2909-2916 (2009).
Guizy, M., et al., "ω-3 and ω-6 Polyunsaturated fatty acids block HERG channels." Am J Physiol Cell Physiol 289:C1251-C1260 (2005).
Gyarmathy, M., "Selection from the industrial manufacturing. 5th part: Gelatine capsules. 5/2 part: Soft gelatine capsules," Gyogyszereszet, vol. 38, No. 2, pp. 105-109 (1994) (with English summary).
Hakonarson, H., et al., "Effects of a 5-lipoxygenase-activating protein inhibitor on biomarkers associated with risk of myocardial infarction—a randomized trial." JAMA, 293(8):2245-56 (2005).
Hall, W. L., et al., "A high-fat meal enriched with eicosapentaenoic acid reduces postprandial arterial stiffness measured by digital volume pulse analysis in healthy men." J. Nutr. 138: 287-291 (2008).
Hamazaki et al., "Docosahexaenoic Acid-Rich Fish Oil Does Not Affect Serum Lipid Concentrations of Normolipidemic Young Adults", American Institute of Nutrition, 126(11):2784-2789, Nov. (1996).
Hamazaki et al., "Effects of Orally Administered Ethyl Ester of Eicosapentaenoic Acid (EPA: C20:5, omega-3) on PG12-Like Substance Production by Rat Aorta" Prostaglandins, vol. 23 No. 4, pp. 557-567 (1982).
Hamazaki T. et al., "Reduction of microalbuminuria in diabetics by Eicosapentaenoic acid ethyl ester" Lipids. 25 (9):542-5 (1990).
Hampel H, Abraham NS, El-Se rag HB. Meta-analysis: obesity and the risk for gastroesophageal reflux disease and its complications. Ann. Intern. Med. Aug. 2005 143 (3): 199-211.
Han, J. J., et al., "Enhancement of both reaction yield and rate of synthesis of structured triacylglycerol containing eicosapentaenoic acid under vacuum with water activity control." Lipids 34:989-995 (1999).
Hanasaki, K., et al., "Potent modification of low density lipoprotein by group X secretory phospholipase A2 is linked to macrophage foam cell formation." J. Biol. Chem. 277(32):29116-24 (2002).
Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011)(573 pages).
Hannah, J., et al., "Effect of dietary fatty acids on LDL binding." Ann N Y Acad Sci., 683:178-182 (1993).
Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993).

(56) References Cited

OTHER PUBLICATIONS

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harris, "n-3 Fatty acids and lipoproteins: a comparison of results from human and animal studies," Lipids 31, 243-252 (1996).

Harris, W. S. et al. "Safety and efficacy of Omacor in severe hypertriglyceridemia," Journal of Cardiovascular Risk, 4:385-391 (1997).

Harris, W. S. "Fish oils and plasma lipid and lipoprotein metabolism in humans: a critical review." J Lipid Res. 30:785-807 (1989).

Harris, W. S., "The omega-3 index as a risk factor for coronary heart disease." Am J Olin Nutr 87:1997S-2002S (2008).

Harris, W. S., et al., "n-3 Fatty acids and urinary excretion of nitric oxide metabolites in humans." Am. J. Clin. Nutr., 65:459-64 (1997).

Harris, W. W S., et al., "Influence of n-3 fatty acid supplementation on the endogenous activities of plasma lipases." Am. J. Clin. Nutr. 66:254-60 (1997).

Harris, W.S., "Expert opinion: omega-3 fatty acids and bleeding—cause for concern?" The American Journal of Cardiology 99(6A): 45C-46C (2007).

Harris, W.S., "n-3 Fatty acids and human lipoprotein metabolism: an update." Lipids 34:S257-S258 (1999).

Harris, W.S., "n-3 Fatty acids and serum lipoproteins: human studies." Am J Clin Nutr 65:1645S-54S (1997).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

Harris, W.S., et al., "Omega-3 fatty acids and coronary heart disease risk: Clinical and mechanistic perspectives." Atherosclerosis 197:12-24 (2008).

Harris, W.S., et al., "Stearidonic acid increases the red blood cell and heart eicosapentaenoic acid content in dogs." Lipids 42:325-333 (2007).

Harris, W.S., et al., "Tissue n-3 and n-6 fatty acids and risk for coronary heart disease events." Atherosclerosis 193:1-10 (2007).

Hartweg, J., et al., "Potential impact of omega-3 treatment on cardiovascular disease in type 2 diabetes." Curr Opin Lipidol., 20:30-38 (2009).

Hata et al, Geriatric Medicine, 30 (5), 799-852, 1992 (with English introduction).

Hawthorne, et al., "High dose eicosapentaenoic acid ethyl ester: effects on lipids and neutrophil leukotriene production in normal volunteers." Br. J. Clin. Pharmac., vol. 30, 187-194 (1990).

Hayashi et al., Decreases in Plasma Lipid Content and Thrombotic Activity by Ethyl Icosapentate Purified from Fish Oiles, Current Therapeutic Research, vol. 56, No. 1, pp. 24-31 (1995).

Herbette L, Marquardt J, Scarpa A, Blasie JK. A direct analysis of lamellar x-ray diffraction from hydrated oriented multilayers of fully functional sarcoplasmic reticulum. Biophys. J. 1977;20(2):245-272.

Hibbeln, J. R., et al., "Healthy intakes of n-3 and n-6 fatty acids: estimations considering worldwide diversity." Am J Clin Nutr. 83:1483S-93S (2006).

Higashihara et al. "Effects of Eicosapentaenoic Acid on Biochemical Failure after Radical Prostatectomy for Prostate Cancer," in vivo 24:561-566 (2010).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1 beta induction of nitric oxide synthase through mechanism involving p44/42 MAPK activation in rat vascular smooth muscle cells." British Journal of Pharmacology 136:613-619 (2002).

Hirai, A., et al., "The effects of the oral administration of fish oil concentrate on the release and the metabolism of [14C] arachidonic acid and [14C] eicosapentaenoic acid by human platelets", Thromb. Res., 28:285-298, (1982).

Hirano T, Ito Y, Koba S, Toyoda M, Ikejiri A, Saegusa H, Yamazaki J, Yoshino G. Clinical significance of small dense low-density lipoprotein cholesterol levels determined by the simple precipitation method. Arterioscler. Thromb. Vase. Biol. 2004;24(3):558-563.

Hirano, R., et al., "Regulation by long-chain fatty acids of the expression of cholesteryl ester transfer protein in HepG2 cells." Lipids, 36:401-406 (2001).

Hofacer R, et al., Omega-3 fatty acid deficiency increases stearoyl-CoA desaturase expression and activity indices in rat liver: Positive association with non-fasting plasma triglyceride levels, Prostaglandins Leukot. Essent. Fatty Acids. 2012;86:71-7.

Hoffman, "Atherosclerosis: Prevention through the Ages," WebMD, https://www.webmed.com/heart/features/atherosclerosis-prevention-through-ages#1, (Dec. 4, 2007).

Hohenester, "Primary Biliary Cirrhosis," Semin Immunopathol. 31L:283-307, 285 (2009).

Holmeide, A. K., et al., "Oxidative degradation of eicosapentaenoic acid into polyunsaturated aldehydes." Tetrahedron 59:7157-7162 (2003).

Holub, B.J., PhD, "Fish Oils and Cardiovascular Disease", Canadian Medical Association Journal, 141(10):1063 (1989).

Holvoet P, Kritchevsky SB, Tracy RP, Mertens A, Rubin SM, Butler J, Goodpaster B, Harris TB. The metabolic syndrome, circulating oxidized LDL, and risk of myocardial infarction in wellfunctioning elderly people in the health, aging, and body composition cohort. Diabetes. 2004;53(4):1068-1073.

Hom et al., "Soft Gelatin Capsules II: Oxygen Permeability Study of Capsule Shells," J Pharm Sci. (1975) 64(5):851-857.

Hombeck, M., et al., "Biosynthesis of the algal pheromone fucoserratene by the freshwater diatom Asterionella formosa (Bacillariophyceae)." Tetrahedron 54:11033-11042 (1998).

Horrobin, D.F. The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).

Hoskins et al., "Combination use of statins and omega-3 fatty acids: an emerging therapy for combined hyperlipidemia," Abstract, 1(5): 579-591(13) (2006).

Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).

HPs2-thrive Collaborative Group, "randomized placebo-controlled trial in 25 673 high-risk patients of er niacin/laroprant: Trial design, pre-specified muscle and liver outcomes, and reasons for stopping study treatment." Eur. Heart J. 2013;34:1279-1291.

Hruska MW, Amico JA, Langaee TY, Ferrell RE, Fitzgerald SM, Frye RF. The effect of trimethoprim on CYP2C8 mediated rosiglitazone metabolism in human liver microsomes and healthy subjects. Br. J. Clin. Pharmacol. 2005;59:70-79.

Hughes et al., "Fish oil produces an atherogenic lipid profile in hypertensive men," Atherosclerosis, 84, pp. 229-237 (1990).

Hulthe J, Hulten LM, Fagerberg B. Low adipocyte-derived plasma protein adiponectin CJ concentrations are associated with the metabolic syndrome and small dense low-density lipoprotein particles: atherosclerosis and insulin resistance study. Metab. Clin. Exp. 2003;52(12):1612-1614.

Huntington's Diesase Drug Works—The DHA Dilemma http://hddrugworks.org/index2.php?option=com_content&task=view&id=185&pop=1&pa . . . Printed on Aug. 22, 2008.(2 pages).

Ignarro LJ, Buga GM, Wood KS, Byrnes RE, Chaudhuri G. Endothelium-derived relaxing factor produced and released from artery and vein is nitric oxide. Proc. Natl. Acad. Sci. USA. 1987;84:9265-9269.

Illingworth, DR, et al., "Comparative effects of lovastatin and niacin in primary hypercholesterolemia: A prospective trial", Arch. Int. Med., 154:1586-1595, (1994).

(56) References Cited

OTHER PUBLICATIONS

Inoue, I., et al., "Expression of peroxisome proliferator-activated receptor α (PPARα) in primary cultures of human vascular endothelial cells." Biochem. Biophys. Res. Comm., 246, 370-374 (1998).

Ishida, Y., et al., "α-Lipoic Acid and Insulin Autoimmune Syndrome." Diabetes Care, 30(9): 2240-41 (2007).

Isley, et al., "Pilot study of combined therapy with ω-3 fatty acids and niacin in atherogenic dyslipidemia," Journal of Clinical Lipidology, 1, 211-217 (2007).

Itoh et al., "Increased adinponectin secretion by highly purified eicosapentaenoic acid in rodent models of obesity and human obses subjects," Arterioscler. Thromb. Vasc. Biol., pp. 1918-1925 (together with online Supplements 1-15) (2007).

Jacob RF, Mason RP. Lipid peroxidation induces cholesterol domain formation in model membranes. J. Biol. Chem. 2005;280(47):39380-39387.

Jacob RF, Walter MF, Self-Medlin Y, Mason RP. Atorvastatin active metabolite inhibits oxidative modification of small dense low-density lipoprotein. J. Cardiovasc. Pharmacol. 2013;62(2):160-166.

Jacobson et al. "Hypertriglyceridemia and Cardiovascular Risk Reduction", Clinical Therapeutics, vol. 29 pp. 763-777 (2007).

Jacobson TA. Opening a new lipid "apo-thecary": incorporating apolipoproteins as potential risk factors and treatment targets to reduce cardiovascular risk. Mayo Clin. Proc. 2011;86:762-780.

Jacobson, T. Secondary Prevention of Coronary Artery Disease with Omega-3 Fatty Acids. Am J Cardiol; 98 [suppl]: 61 i-70i (2006).

Jacobson, T.A., "Role of n-3 fatty acids in the treatment of hypertriglyceridemia and cardiovascular disease." Am J Clin Nutr 87:1981S-90S (2008).

Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).

Jakus V, Rietbrock N. Advanced glycation end-products and the progress of diabetic vascular complications. Physiol. Res. 2004;53(2):131-142.

Jenner, "Presymptomatic Detection of Parkinson's Disease". J Neural Transm Suppl., 40:23-36. (Abstract only) (1993).

Jialal I, Devaraj S. Antioxidants and atherosclerosis: Don't throw out the baby with the bath water. Circulation. 2003;107:926-928.

Jialal, I. "Editorial: Remnant lipoproteins: measurement and clinical significance." Clinical Chemistry 48(2):217-219 (2002).

Jong et al., "Role of ApoCs in Lipoprotein Metabolism: Function Differences Between ApoC1, ApoC2, and ApoC3," Arteriosclerosis, Thrombosis and Vascular Biology. (1999) 19(3):472-484.

Journal of Practical Pharmacy, "Hyperlipidemia Drug," 58(4)1 303-1324 (2007) (with English abstract).

Journal of the Japan Diabetes Society, "The Relationship Between Postprandial ApoB48 Increase and Insulin Resistance in Type-2 Diabetes," 55(Suppl. 1):5310 (Apr. 2012) (with English Translation)(5 pages).

Journal of the Japanese Diabetes Society, "A Case of Familial Combined Hyperlipidemia Associated with Obesity, Type 2 Diabetes Mellitus and Severe Hypertriglyceridemia," 51(3), pp. 233-237 (Mar. 30, 2008) (with English abstract).

Jung, U.J. et al., "n-3 Fatty acids and cardiovascular disease: mechanisms underlying beneficial effects." Am J Clin Nutr 87: 2003S-9S (2008).

Kamanna et al., "Mechanism of Action of Niacin," *The American Journal of Cardiology* (Apr. 17, 2008), 101(8), S20 and S26.

Kamido et al., Lipid Composition of Platelets from Patients with Atherosclerosis:Effect of Purified Eicosapentaenoic Acid Ethyl Ester Administration, 1988, Lipids, 23, pp. 917-923 [Abstract only] (7 pages).

Kaminski WE, Jendraschak E, Kiefl R, et al. Dietary omega-3 fatty acids lower levels of platelet-derived growth factor mRNA in human mononuclear cells. Blood Apr. 1993 81 (7): 1871-9.

Kanayasu, T., et al., "Eicosapentaenoic acid inhibits tube formation of vascular endothelial cells in vitro." Lipids 26:271-276 (1991).

Kastelein et al., Omega-3 Free Fatty Acids for the Treatment of Severe Hypertriglyceridemia: The EpanoVa for Lowering Very High Triglycerides (EVOLVE) Trial, J. Clin. Lipidol. (JACL 597) 2013 (54 pages).

Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).

Katayama et al., "Efficacy and Safety of Ethyl Icosapentate (Epadel) Given for a Long Term Against Hyperlipidemia," Prog. Med., 21:457-467 (2001) (with English translation).

Kato, T., et al., "Palmitate impairs and eicosapentaenoate restores insulin secretion through regulation of SREBP-lc in pancreatic islets." Diabetes, 57(9):2382-2392 (2008) (published online May 5, 2008.).

Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi, 72(1):18-24 (1983).

Kawano, H., et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid", J. Atheroscler. Thromb., 9:170-177, (2002).

Kawashima, H., et al., "Oral Administration of Dihomo-γ-Linolenic Acid Prevents Development of Atopic Dermatitis in NC/Nga Mice." Lipids 43:37-43 (2008).

Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. 2005;366:1849-1861.

Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).

Kelley, et al., "Docosahexaenoic acid supplementation improves fasting and postprandial lip profiles in hypertriglyceridemic men." The American Journal of Clinical Nutrition, 86: 324-333 (2007).

Kellner-Weibel G, Yancey PG, Jerome WG, Walser T, Mason RP, Phillips MC, Rothblat GH. Crystallization of free cholesterol in model macrophage foam cells. Arterioscler. Thromb. Vasc. Biol. 1999;19(8):1891-1898.

Kendall BJ, Macdonald GA, Hayward NK, et al. The risk of Barrett's esophagus associated with abdominal obesity in males and females. Int. J. Cancer May 2013 132 (9): 2192-9.

Kerr, S., Brosnan MJ, Mcintyre M, Reid JL, Dominiczak AF, Hamilton CA. Superoxide anion production is increased in a model of genetic hypertension role of the endothelium. Hypertension. 1999;33:1353-1358.

Kew, S., et al., "Effects of oils rich in eicosapentaenoic and docosahexaenoic acids on immune cell composition and function in healthy humans." Am J Clin Nutr 79:674-81 (2004).

Kholodov et al., "Clinical Pharmacokinetics," M. Medicine. (1985) pp. 89-98, 134-138, 160, 378-380 [with English Summary](27 pages).

Kim F, Tysseling KA, Rice J, Gallis B, Haji L, Giachelli CM, Raines EW, Corson MA, Schwartz MW. Activation of IKKbeta by glucose is necessary and sufficient to impair insulin signaling and nitric oxide production in endothelial cells. J. Mol. Cell. Cardiol. 2005;39(2):327-334.

Kim KA, Park PW, Kim HK, Ha JM, Park JY. Effect of quercetin on the pharmacokinetics of rosiglitazone, a CYP2C8 substrate, in healthy subjects. J. Clin. Pharmacol. 2005;45:941-946.

Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).

Kinoshita, "Anti-hyperlipidemic agents," Nihon Rinsho, 60(5):968-74 (May 2002) (with English Abstract)(11 pages).

(56) References Cited

OTHER PUBLICATIONS

Kinsella, J.E., et al., "Dietary n-3 polyunsaturated fatty acids and amelioration of cardiovascular disease: possible mechanisms." Am J Clin Nutr 52:1-28 (1990).
Kitada, 9th Diabetes Drug and Drug Related Seminar Diabetes Q&A, Kanazawa Medical University, Diabetes and Endocrine Internal Medicine (http://plaza.umin.ac.jp/iby/etcdata/yakuyaku110410.pdf)(Apr. 10, 2011) (with English translation)(105 pages).
Knapp HR. Dietary fatty acids in human thrombosis and hemostasis. Am. J. Clin. Nutr. May 1997 65 (5 Suppl): 1687S-98S.
Knopp, R.H., et al., "Contrasting effects of unmodified and time-release forms of niacin on lipoproteins in hyperlipidemic subjects: clues to mechanism of action of niacin", Metabolism, 34:642-650, (1985).
Koba S, Hirano T, Ito Y, Tsunoda F, Yokota Y, Ban Y, Iso Y, Suzuki H, Katagiri T. Significance of small dense low-density lipoprotein-cholesterol concentrations in relation to the severity of coronary heart diseases. Atherosclerosis. 2006;189(1):206-214.
Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).
Kojda G, Harrison DG. Interactions between no. And reactive oxygen species: Pathophysiological importance in atherosclerosis, hypertension, diabetes and heart failure. Cardiovasc. Res. 1999;43:562-571.
Kojima, T, et al., "Long-term administration of highly purified eicosapentaenoic acid provides improvement of psoriasis." Dermatologica, 182:225-230 (1991).
Koroshetz, W.J. Huntington's Disease. In Samuels, M. (ed.) Office Practice of Neurology, pp. 654-661 (1996).
Kosonen, O., et al., "Inhibition by nitric oxide-releasing compounds of E-selectin expression in and neutrophil adhesion to human endothelial cells." European Journal of Pharmacology 394:149-156 (2000).
Koyama et al., Plaque Reduction and Stabilization Observed in Borderline Diabetes Using Coronary CT Angiogram During Administration of Purified Eicosapentaenoic Acid (EPA) Ther. Res. 31(2):219-225 (Feb. 2010) (with English translation)(20 pages).
Krauss RM. Heterogeneity of plasma low-density lipoproteins and atherosclerosis risk. Curr. Opin. Lipidol. 1994;5(5):339-349.
Kris-Etherton, P. M., et al., "Omega-3 Fatty Acids and Cardiovascular Disease—New Recommendations From the American Heart Association." Arterioscler Thromb Vasc Biol. 23:151-152 (2003).
Kris-Etherton, et al., "Fish Consumption, Fish Oil, Omega-3 Fatty Acids, and Cardiovascular Disease" Circulation, 106:2747-2757 (2002).
Krzynowek et al., "Purification of Omega-3 Fatty Acids from Fish Oils Using HPLC: An Overview," National Marine Fisheries—Proceedings of the first joint conference of the Tropical and Subtropical Fisheries Technological Soceity of the Americas with the Atlantic Fisheries Technological Society, pp. 74-77 (1988).
Ku, K., et al., "Beneficial Effects of to-3 Fatty Acid Treatment on the Recovery of Cardiac Function After Cold Storage of Hyperlipidemic Rats." Metabolism, 48(10):123-1209 (1999).
Kunimoto M, Inoue K, Nojima S. Effect of ferrous ion and ascorbate-induced lipid peroxidation on liposomal membranes. Biochem. Biophys.Acta. 1981;646(1):169-178.
Kurabayashi, T., et al., "Eicosapentaenoic acid effect on hyperlipidemia in menopausal Japanese women." Obstet Gynecol 96:521-8 (2000).
Labor Diagnostik Karlsruhe, "Target Values of Lipid Metabolism [Recommendation for lipid plasma levels in Germany]," (exact publication date unknown; circa 2006) (with English abstract)(4 pages).
Lada et al., "Associations of Low Density Lipoprotein Particle Compositions with Atherogenicity," Curr. Opin. Lipidol. (2004) 15(1):19-24.
Lai, E. et al "Suppression of niacin-induced vasodilation with an antagonist to prostaglandin D2 receptor subtype 1", Clin. Pharm. & Ther., 81:849-857, (2007).

Laidlaw, M., et al., "Effects of supplementation with fish oil-derived n-3 fatty acids and γ-linolenic acid on circulating plasma lipids and fatty acid profiles in women." Am J Clin Nutr 77:37-42 (2003).
Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. 2008;62(7): 1087-1095.
Lamharzi N, Renard CB, Kramer F, Pennathur S, Heinecke JW, Chait A, Bomfeldt KE. Hyperlipidemia in concert with hyperglycemia stimulates the proliferation of macrophages in atherosclerotic lesions: potential role of glucose-oxidized LDL. Diabetes. 2004;53(12):3217-3225.
Landmesser U, Dikalov S, Price SR, McCann L, Fukai T, Holland SM, Mitch WE, Harrison DG. Oxidation of tetrahydrobiopterin leads to uncoupling of endothelial cell nitric oxide synthase in hypertension. J. Clin. Invest. 2003;111:1201-1209.
Larsen, L.N., et al., "Heneicosapentaenoate (21:5n-3): Its incorporation into lipids and its effects on arachidonic acid and eicosanoid Synthesis." Lipids 32:707-714 (1997).
Laufs et al., "Upregulation of endothelial nitric oxide synthase by hmg coa reductase inhibitors," Circulation (1998) 97:1129-1135.
Law, M.R., et al., "Quantifying effect of statins on low density lipoprotein cholesterol, ischaemic heart disease, and stroke: systematic review and meta-analysis." Br Med J., 326:1423-1427 (2003).
Lawson et al., "Human absorption of fish oil fatty acids as triacylglycerols, free acids or ethyl esters," Biochemical and Biophysical Research Communications 152(1):328-335 (Apr. 15, 1988).
Leaf, "Hypertriglyceridemia: A Guide to Assessment and Treatment," Hospital Physician 17-23 (Sep. 2008).
Leaf, A., "Historical overview of n3 fatty acids and coronary heart disease." Am J Clin Nutr 87:1978S-80S. (2008).
Lee and G.Y.H. Lip, "The Role of Omega-3 Fatty Acids in the Secondary Prevention of Cardiovascular Disease", Q J Med, 96:465-480, (2003).
Lee C, Sigari F, Segrado T, Horkko S, Hama S, Subbaiah PV, Miwa M, Navab M, Witztum JL, Reaven PD. All ApoB-containing lipoproteins induce monocyte chemotaxis and adhesion when minimally modified. Modulation of lipoprotein bioactivity by platelet-activating factor acetylhydrolase. Arterioscler. Thromb. Vase. Biol. 1999; 19(6): 1437-1446.
Lee, J.H., et al., "Omega-3 fatty acids for cardioprotection." Mayo Clin Proc., 83(3):324-332 (2008).
Leigh-Firbank et al., "Eicosapentaenoic acid and docosahexanoic acid from fish oils: differential associations with lipid responses," Br. J. Nutr. 87:435-445 (2002).
Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).
Leonard, Brian E., "Neurological Aspects", Fundamentals of Psychopharmacology,186-187, (1997).
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, (1999).
Li, D., t al., "Effect of dietary a-linolenic acid on thrombotic risk factors in vegetarian men." Am J Clin Nutr 69:872-82 (1999).
Li, H. et al., "EPA and DHA reduce LPS-induced inflammation responses in HK-2 cells: Evidence for a PPAR-γ-dependent mechanism." Kidney Int'l. 67:867-74 (2005).
Libby, "Inflammation and atherosclerosis," Nature (2002) 420(6917):868-874.
Lichtman et al., "Depression and Coronary Heart Disease, Recommendations for Screening, Referral and Treatment," AHA Science Advisory, Circulation 118:1768-1775 (Oct. 21, 2008).
Lien, E.L., "Toxicology and safety of DHA." Prostaglandins Leukot Essent Fatty Acids., 81:125-132 (2009).
Lin, Pao-Yen, M.D., et al., "A Meta-Analytic Review of Double-Blind, Placebo-Controlled Trials of Antidepressant Efficacy of Omega-3 Fatty Acids", Psychiatry, 1056-1061 (Jul. 2007).

(56) References Cited

OTHER PUBLICATIONS

Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).

Lindsey, S., et al., "Low density lipoprotein from humans supplemented with n-3 fatty acids depresses both Ldl receptor activity and LDLr mRNA abundance in HepG2 cells." J Lipid Res., 33:647-658 (1992).

Lipitor [package insert]. New York, NY: Parke-Davis (2012). (22 pages).

Lipitor [product information] Dublin, Ireland: Pfizer Inc. ( 2007). (18 pages).

Liu et al., "Effects of stable fish oil and simvastatin on plasma lipoproteinc in patients with hyperlipidemia," Nutrion Res. , vol. 23, pp. 1027-1034 (2003).

Liu X, et al., Stearoyl CoA Desaturase 1: Role in Cellular Inflammation and Stress, Adv. Nutr. 2011;2:15-22.

Lohmussaar, E., et al., "ALOX5AP Gene and the PDE4D Gene in a Central European Population of Stroke Patients." Stroke, 36:731-736 (2005).

Lovaza (omega-3-acid ethyl esters) Capsules, Prescribing information, GlaxoSmithKline (Nov. 2008).(9 pages).

Lovaza [package insert]. Research Triangle Park, NC: GlaxoSmithKline (2012). (14 pages).

Lovaza Side Effects, web archived webpage, archived from Drugs. com website on (Jul. 31, 2010), Retrieved from URL <https://web.archive.org/web/20100731021902/https://www.drugs.com/sfx/lovaza-side-effects.html> (4 pages)(Jul. 2010).

Lovaza, (omega-3-acid ethyl esters) Capsules, Prescribing information Smith Kline Beechum (Jul. 2009).(17 pages).

Lovaza, GlaxoSmithKline, Lovaza Prescribing Information, Jun. 2008 [retrieved from the internet Jun. 6, 2012 <https://web.archive.org/web/20090206170311/http://us.gsk.com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.' (12 pages).

LOVAZA® (omega-3-acid ethyl esters) Capsules, Prescribing information, GlaxoSmithKline, (Dec. 2010)(12 pages).

Lovaza®, Physicians' Desk Reference 2699-2701 (62d ed., 2008). (4 pages).

Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (2004).

Lu, G., et al., "Omega-3 fatty acids alter lipoprotein subfraction distributions and the in vitro conversion of very low density lipoproteins to lowdensity lipoproteins." J Nutr Biochem., 10:151-158 (1999).

Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).

Luria, MH, "Effect of low-dose niacin on high-density lipoprotein cholesterol and total cholesterol/high density lipoprotein cholesterol ratio", Arch. Int. Med., 148:2493-2495, (1998).

Lvovich V, Scheeline A. Amperometric sensors for simultaneous superoxide and hydrogen peroxide detection. Anal. Chem. 1997;69:454-462.

Madhavi et al., "Effect of n-6 and n-3 fatty acids on the survival of vincristine sensitive and resistant human cervical carcinoma cells in vitro", Cancer Letters, vol. 84. No. 1, pp. 31-41 (1994).

Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).

Mak IT, Weglicki WB. Antioxidant properties of calcium channel blocking drugs. Methods Enzymol. 1994;234:620-630.

Maki, K.C., et al., "Baseline lipoprotein lipids and low-density lipoprotein cholesterol response to prescription omega-3 acid ethyl ester added to simvastatin therapy." Am J Cardiol., 105:1409-1412 (2010).

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).

Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007).

Malinski T, Taha Z. Nitric oxide release from a single cell measured in situ by a porphyrinic-based microsensor. Nature. 1992;358:676-678.

Mallat, Z., et al., "Apoptosis in the vasculature: mechanisms and functional importance." British Journal of Pharmacology 130:947-962 (2000).

Mallet, Z., et al., "Protective role of interleukin-10 in atherosclerosis." Circ. Res. 85:e17-e24 (1999).

Marangell, Lauren B., M.D., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003).

Marckmann, P., "Fishing for heart protection." Am J Clin Nutr, 78:1-2 (2003).

Marder, "An Approach to Treatment Resistance in Schizophrenia," British Journ. Psychiatry, 37:19-22 (1999).

Margolis, Simeon "What is Hyperlipidemia?" (http:www.healthcommunities.com/highcholesterol/whatishyperlipidemia.shtml, accessed Oct. 20, 2015, published Aug. 25, 2011)(4 pages).

Martinez-Gonzalez J, Raposo B, Rodriguez C, Badimon L. 3-hydroxy-3-methylglutaryl coenzyme a reductase inhibition prevents endothelial no synthase downregulation by atherogenic levels of native ldls: Balance between transcriptional and posttranscriptional regulation. Arterioscler. Thromb. Vasc. Biol. 2001;21:804-809.

Martinez-Gonzalez, Jose et al., "Estatinas y acidos grasos omega-3. Disminucion de la mortalidad cardiovascular dependiente e independiente de la reduccion de la colesterolemia," (2006) Rev Esp Cardiol Suppl., 6(D):20D-30D [with English abstract].

Martin-Jadraque, R. et al., Effectiveness of low dose crystalline nicotinic acid in men with low density lipoprotein cholesterol levels. Arch. Int. Med. 156: 1081-1088. (1996).

Martz, "Moving Upstream in Huntington's," Science-Business eXchange, 2 pgs., 2008.

Mason et al., "Comparative lipid antioxidant effects of omega-3 fatty acids in combination with HMG-CoA reductase inhibitors," Journ. Clin. Lipidology (2011) 5(3):20.

Mason et al., "Direct evidence for cholesterol crystalline domains in biological membranes: role in human pathobiology," Biochimica et Biophysica Acta 198-207 (Mar. 10, 2003).

Mason et al., "Eicosapentaenoic Acid (EPA) inhibits the formation of membrane cholesterol crystalline domains by a potent antioxidant mechanism," Journ. Clin. Lipid., 7(3): 272-273 (2013) [Abstract only].

Mason et al., "Eicosapentaenoic acid inhibits glucose-induced membrane cholesterol crystalline domain formation through a potent antioxidant mechanism," Biochim. Biophy. Acta., 1848(2):502-9, (Feb. 2015).

Mason et al., "Eicosapentaenoic Acid Inhibits Oxidation of ApoB-containing Lipoprotein Particles of Different Size In Vitro When Administered Alone or in Combination With Atorvastatin Active Metabolite Compared With Other Triglyceride-lowering Agents," J. Cardiovasc. Pharmacol., 68(1):33-40 (Jul. 2016).

Mason et al., "Eicosapentaenoic acid reduces membrane fluidity, inhibits cholesterol domain formation, and normalizes bilayer width in atherosclerotic-like model membranes," Biochim. Biophy. Acta., 1858(12):3131-3140 (Dec. 2016).

Mason RP, Gonye GE, Chester DW, Herbette LG. Partitioning and location of Bay K 8644, 1,4-dihydropyridine calcium channel agonist, in model and biological membranes. Biophys. J. 1989;55(4):769-778.

Mason RP, Jacob RF, Kubant R, Walter MF, Bellamine A, Jacoby A, Mizuno Y, Malinski T. Effect of enhanced glycemic control with

(56) References Cited

OTHER PUBLICATIONS saxagliptin on endothelial nitric oxide release and CD40 levels in obese rats. J. Atheroscler. Thromb. 2011;18:774-783.

Mason RP, Jacob RF. Membrane microdomains and vascular biology: Emerging role in atherogenesis. Circulation. May 6, 2003; 107:2270-2273.

Mason RP, Kalinowski L, Jacob RF, Jacoby AM, Malinski T. Nebivolol reduces nitroxidative stress and restores nitric oxide bioavailability in endothelium of black americans. Circulation. 2005;112:3795-3801.

Mason RP, Kubant R, Heeba G, Jacob RF, Day CA, Medlin YS, Funovics P, Malinski T. Synergistic effect of amlodipine and atorvastatin in reversing ldl-induced endothelial dysfunction. Pharm. Res. 2008;25:1798-1806.

Mason RP, Walter MF, Day CA, Jacob RF Active metabolite of atorvastatin inhibits membrane cholesterol domain formation by an antioxidant mechanism. J. Biol. Chem. 2006;281(14):9337-9345.

Mason RP, Walter MF, Day CA, Jacob RF. Intermolecular differences for HMG-CoA reductase inhibitors contribute to distinct pharmacologic and pleiotropic actions. Am. J Cardiol. 2005;96(5A):11F-23F.

Mason RP, Walter MF, Jacob RF. Effects of hmg-coa reductase inhibitors on endothelial function: Role of microdomains and oxidative stress. Circulation. 2004;109:1134-1141.

Mason RP, Walter MF, Mason PE. Effect of oxidative stress on membrane structure: Small angle x-ray diffraction analysis. Free Radic. Biol. Med. 1997;23(3):419-425.

Mason RP. Molecular basis of differences among statins and a comparison with antioxidant vitamins. Am. J. Cardiol. 2006;98:34P-41P.

Mataki et al., "Effect of Eicosapentaenoic Acid in Combination with HMG-CoA Reductase Inhibitor on Lipid Metabolism," Int. Med. J. 5(1):35-36 (Mar. 1998).

Mater, M.K., et al., "Arachidonic acid inhibits lipogenic gene expression in 313-L1 adipocytes through a prostanoid pathway." J. Lipid Res. 39:1327-1334 (1998).

Matsumoto, M., et al., "Orally administered eicosapentaenoic acid reduces and stabilizes atherosclerotic lesions in ApoE-deficient mice." Atherosclerosis, 197(2):524-533 (2008).

Matsuzaki et al., "Incremental Effects of Eicosapentaenoic Acid on Cardiovascular Events in Statin-Treated Patients with Coronary Artery Disease," Circ. J. 73:1283-1290 (2009).

Matsuzawa, Y., et al., "Effect of Long-Term Administration of Ethyl Icosapentate (MND-21) in Hyperlipaemic Patients," J. Clin Therapeutic & Medicines, 7: 1801-16 (1991).

Mattson MP. Modification of ion homeostasis by lipid peroxidation: roles in neuronal degeneration and adaptive plasticity. Trends Neurosci. 1998;21(2):53-57.

Mayatepek, E., et al., The Lancet, vol. 352, Leukotriene C4-synthesis deficiency: a new inborn error of metabolism linked to a fatal developmental syndrome, pp. 1514-1517 (1998).

Mayo Clinic at http://www.mayoclinic.org.diseases-conditions/high-blood-cholesterol/in-depth/cholesterol (2014)(5 pages).

McElroy, S.L., et al., "Clozapine in the Treatment of Psychotic Mood Disorders, Schizoaffective Disorder, and Schizophrenia", Journal of Clinical Psychiatry, vol. 52, No. 10, pp. 411-414 (1991).

McIntyre M, Hamilton CA, Rees DD, Reid JL, Dominiczak AF. Sex differences in the abundance of endothelial nitric oxide in a model of genetic hypertension. Hypertension. 1997;30:1517-1524.

McKenney et al., "Prescription omega-3 fatty acids for the treatment of hypertriglyceridemia," Am. J. Health Syst. Pharm., 64(6):595-605 (2007).

McKenney et al., CMRO, "Comparison of the efficacy of rosuvastatin versus atorvastatin, simvastatin and pravastatin in achieving lipid goals: results from the STELLAR trial", 689-98 (2003).

McKenney, J., "Niacin for dyslipidemia: considerations in product selection", Am. J. Health Syst. Pharm., 60:995-1005, (2003).

McKenney, J.M. et al. Study of the pharmacokinetic interaction between simvastatin and prescription omega-3-acid ethyl esters. J. Clin. Pharmacol. 46, 785-791 (2006).

McKenney, James et al., "Role of prescription omega-3 fatty acids in the treatment of Hypertriglyceridemia," Pharmacotherapy, LNKD-Pubmed: 17461707, vol. 27, No. 5, pp. 715-728 (2007).

McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (1997).

McMurchie, E.J., et al., "Incorporation and effects of dietary eicosapentaenoate (20 : 5(n-3)) on plasma and erythrocyte lipids of the marmoset following dietary supplementation with differing levels of linoleic acid." Biochimica et Biophysics Acta, 1045:164-173 (1990).

McNamara JR, et al., Remnant-like particle (RLP) Cholesterol is an independent cardiovascular disease risk factor in women: results from the Framingham Heart Study, Atherosclerosis, vol. 154(1), pp. 229-36 (2001).

MedlinePlus. "Coronary heart disease," Available at: https://medlineplus.gov/ency/article/007115.htm (review date Jul. 14, 2015)(accessed Sep. 2, 2016)(5 pages).

Menuet, R. et al., "Importance and management of dyslipidemia in the metabolic syndrome," American Journal of the Medical Sciences Dec. 2005 US, vol. 33, No. 6, pp. 295-302 (2005).

Merched, A.J., et al., "Atherosclerosis: evidence for impairment of resolution of vascular inflammation governed by specific lipid mediators." FASEB J. 22:3595-3606 (2008).

Merkl et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, vol. 118, pp. 743-753 (2008).

Mesa, M., "Effects of oils rich in Eicosapentaenoic and docosahexaenoic acids on the oxidizability and thrombogenicity of low-density lipoprotein," Artherosclerosis 175, pp. 333-343 (2004).

Metcalf, R.G. et al., "Effect of dietary n-3 polyunsaturated fatty acids on the inducibility of ventricular tachycardia in patients with ischemic cardiomyopathy." Am J Cardiol 101:758-761 (2008).

Metcalf, R.G., et al., "Effects of fish-oil supplementation on myocardial fatty acids in humans." Am J Clin Nutr 85:1222-28 (2007).

Meyer, et al., "Dose-Dependent Effects of Docosahexaenoic Acid Supplementation on Blood Lipids in Statin-Treated Hyperlipidaemic Subjects." Lipids, 42:109-115 (2007).

Meyers, et al., "Nicotinic acid induces secretion of prostaglandin D2 in human macrophages: An in vitro model of the niacin-flush", Atherosclerosis, 192:253-258, (2007).

Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. 2004;24:136-140.

Michos et al., "Niacin and Statin Combination Therapy for Atherosclerosis Regression and Prevention of Cardiovascular Disease Events," Journ. Amer. Coll. Cardiol., vol. 59, No. 23:2058-2064 (2012).

Mii S. et al., "Perioperative use of eicosapentaenoic acid and patency of infrainguinal vein bypass: a retrospective chart review." Curr Ther Res Clin Exp. 68:161-174 (2007).

Miles, et al., "Effect of orlistat in overweight and obese patients with type 2 diabetes treated with metformin," Diabetes Care, 25(7):1123-1128 (2002).

Miller AK, DiCicco RA, Freed MI. The effect of ranitidine on the pharmacokinetics of rosiglitazonein healthy adult male volunteers. Clin. Ther. 2002;24:1062-1071.

Miller AK, Inglis AM, Culkin KT, Jorkasky DK, Freed MI. The effect of acarbose on the pharmacokinetics of rosiglitazone. Eur. J. Clin. Pharmacol. 2001;57:105-109.

Miller M, Stone NJ, Ballantyne C, et al. Triglycerides and cardiovascular disease: a scientific statement from the American Heart Association. Circulation. 2011;123:2292-2333.

Miller, M., et al., "Impact of lowering triglycerides on raising HDL-C in hypertriglyceridemic and non-hypertriglyceridemic subjects." International Journal of Cardiology 119:192-195 (2007).

Minihane, A.M., et al., "ApoE polymorphism and fish oil supplementation in subjects with an atherogenic lipoprotein phenotype." Arterioscler. Thromb. Vasc. Biol. 20:1990-1997 (2000).

(56) References Cited

OTHER PUBLICATIONS

Mishra, A., et al., "Oxidized omega-3 fatty acids inhibit NF-κB activation via a PPARα-Dependent Pathway." Arterioscler Thromb Vasc Biol. 24:1621-1627 (2004).
Missouri DUReport, Statin Therapy (Oct./Nov. 2003) Drug Use Review Newsletter 8(6):1-9.
Mita, T. et al., Eicosapentaenoic acid reduces the progression of carotid intima-media thickness in patients with type 2 diabetes, Atherosclerosis 191:162-167 (2007).
Mizota M, Katsuki Y, Mizuguchi K, Endo S, Miyata H, Kojima M, Kanehiro H et al. "Pharmacological studies of eicosapentaenoic acid ethylester (EPA E) on high cholesterol diet-fed rabbits," Nippon Yakurigaku Zasshi, 91:255-66 (1988) (with English abstract).
Mizota M, Katsuki Y, Mizuguchi K, Endo S, Miyata H, Kojima M, Kanehiro H et al. "The effects of eicosapentaenoic acid ethylester (EPA E) on arterial thrombosis in rabbits and vascular lesions in rats," Nippon Yakurigaku Zasshi, 91:81-9 (1988)(with English abstract).
Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol., 59:3307-12 (1992).
Mizuguchi, K., et al., "Ethyl all-cis-5,8,11,14,17-icosapentaenoate modifies the biochemical properties of rat very low-density lipoprotein." European Journal of Pharmacology, 231:221-227 (1993).
Mizuguchi, K., et al., "Mechanism of the lipid-lowering effect of ethyl all-cis-5,8,11,14,17-icosapentaenoate." European Journal of Pharmacology, 231:121-127 (1993).
Mochida Press Release, Pharmaceutical Col., Ltd.: Conclusion of Distributorship Agreement Concerning Switch-OTC Drug for Hyperlipidemia Treatment, Epadel, (2009)(1 page).
Mochida, Announcement, Mochida Announces Completion of "JELIS" Major Clinical Trial for "Epadel," Mar. 22, 2005 (2 pages).
Mochida's Epadel Reduces Risk of Stroke Recurrence—New Results of JELIS Major Clinical Trial, JCNNetwork Newswire Nov. 13, 2006 (2 pages).
Mora, S., et al., "LDL particle subclasses, LDL particle size, and carotid atherosclerosis in the Multi-Ethnic Study of Atherosclerosis (MESA)." Atherosclerosis. 2007;192:211-217 (2007).
Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (2000).
Mori TA, Woodman RJ. "The independent effects of eicosapentaenoic acid and docosahexaenoic acid on cardiovascular risk factors in humans," Curr Opin Clin Nutr Metab Care 2006; 9:95-104 (2006).
Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 71:1085-1094 (2000).
Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (2003).
Mori, Trevor A., et al., "Docosahexaenoic Acid but Not Eicosapentaenoic Acid Lowers Ambulatory Blood Pressure and Heart Rate in Humans", Hypertension, 34(2):253-60 (Aug. 1999).
Morita, I., et al., "Effects of purified eicosapentaenoic acid on arachidonic acid metabolism in cultured murine aortic smooth muscle cells, vessel walls and platelets." Lipids 18:42-490 (1983).
Morrow, JD, "Release of markedly increased quantities of prostaglandin D2 in vivo in humans following the administration of nicotinic acid", Prostaglandins, 38:263-274, (1989).
Morton, R.E., "Specificity of lipid transfer protein for molecular species of cholesteryl ester." J Lipid Res., 27:523-529 (1986).
Mosher LR et al., "Nicotinic Acid Side Effects and Toxicity: A review," Am J Psychiat., 126: 1290-1296 (1970).

Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (2007).
Mostad, I.L., et al., "Effects of n-3 fatty acids in subjects with type 2 diabetes: reduction of insulin sensitivity and time-dependent alteration from carbohydrate to fat oxidation." Am J Clin Nutr 84:540-50 (2006).
Mozaffarian et al., "Omega-3 fatty acids and cardiovascular disease: effects on risk factors, molecular pathways and clinical events," J. Am. Coll. Cardiol. (2011) 58(2):2047-2067.
Mozaffarian, "JELIS, fish oil, and cardiac events," www.thelancet.com vol. 369, pp. 1062-1063 (2007).
Mozaffarian, D., "Fish and n-3 fatty acids for the prevention of fatal coronary heart disease and sudden cardiac death." Am J Clin Nutr, 87:1991S-6S (2008).
Mozaffarian, D., et al., "Dietary fish and w-3 fatty acid consumption and heart rate variability in US adults." Circulation, 117:1130-1137 (2008).
Naba, H., et al., "Improving effect of ethyl eicosapentanoate on statin-induced rhabdomyolysis in Eisai hyperbilirubinemic rats." Biochemical and Biophysical Research Communications, 340:215-220 (2006).
Na gakawa et al., Effect of [EPA] on the Platelet Aggregation and Composition of Fatty Acid in Man: A Double Blind Study, Atherosclerosis 47(1):71-75 (1983).
Naik H, Wu JT, Palmer R, McLean L. The effects of febuxostat on the pharmacokinetic parameters of rosiglitazone, a CYP2C8 substrate. Br. J. Clin. Pharmacol. Jan. 13, 2012;74:327-335.
Nakamura et al., Remnant lipoproteniemia is a risk factor for endothelial vasomotor dysfuction and coronary artery disease in metabolic syndrome, Atherosclerosis, vol. 181(2), pp. 321-327 (2005).
Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).
Nakamura, H., et al., "Evaluation of ethyl icosapentate in the treatment of hypercholesterolemia in kidney transplant recipients." Transplantation Proceedings, 30:3047-3048 (1998).
Nakamura, N. et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999).
Nambi, V., et al., "Combination therapy with statins and omega-3 fatty acids." Am J Cardiol 98:34i-38i (2006).
Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).
Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005)(16 pages).
Nattel, S. et al., "Atrial remodeling and atrial fibrillation: Mechanisms and implications." Circ Arrhythmia Electrophysiol, 1:62-73 (2008).
Negre-Salvayre, A., et al., "Advanced lipid peroxidation end products in oxidative damage to proteins. Potential role in diseases and therapeutic prospects for the inhibitors." British Journal of Pharmacology 153:6-20 (2008).
Nelson, G.J., et al., "The Effect of Dietary Docosahexaenoic Acid on Plasma Lipoproteins and Tissue Fatty Acid Composition in Humans", Lipids, 32(11):1137-1146, (1997).
Nemets, Boris, M.D., Addition of Omega-3 Fatty Acid to Maintenance Medication Treatment for Recurrent Unipolar Depressive Disorder, Am. J. Psychiatry, 159(3):477-479, (Mar. 2002).
Nemoto et al., "Ethyl-eicosapentaenoic Acid Reduces Liver Lipids and Lowers Plasma Levels of Lipids in Mice Fed a High-Fat Diet, in vivo," 23:685-690 2009).

(56) References Cited

OTHER PUBLICATIONS

Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (1992).
Nestel, et al., "The n-3 fatty acids eicosapentaenoic acid and docosahexaenoic acid increase systemic arterial compliance in humans," Am J Clin Nutr., 76:326-30 (2002).
Nestel, P.J., "Effects of N-3 fatty acids on lipid metabolism." Ann Rev Nutr., 10:149-167 (1990).
Niemi M, Backman JT, Grantors M, Laitila J, Neuvonen M, Neuvonen PJ. Gemfibrozil considerably increases the plasma concentrations of rosiglitazone. Diabetologia. 2003;46: 1319-1323.
Niemi M, Backman JT, Neuvonen PJ. Effects of trimethoprim and rifampin on the pharmacokinetics of the cytochrome P450 2C8 substrate rosiglitazone. Clin. Pharmacol. Ther. 2004;76:239-249.
Nigon F, Lesnik P, Rouis M, Chapman MJ. Discrete subspecies of human low density lipoproteins are heterogeneous in their interaction with the cellular LDL receptor. J. Lipid Res. 1991;32(11):1741-1753.
Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (1997).
Nobukata, H., et al., "Age-related changes in coagulation, fibrinolysis, and platelet aggregation in male WBN/Kob rats." Thrombosis Research 98: 507-516 (2000).
Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).
Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).
Noguchi et al., "Chemoprevention of DMBA-induced mammary carcinogenesis in rats by low-dose EPA and DHA." Br. J. Cancer 75(3): 348-353 (1997).
Nomura et al., "The effects of pitavastatin, eicosapentaenoic acid and combined therapy on platelet-derived microparticles and adiponectin in hyperlipidemic, diabetic patients." Platelets, 20(10:16-22 (2009).
Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).
Nozaki S. et al., "Effects of purified Eicosapentaenoic acid ethyl ester on plasma lipoproteins in primary hypercholesterolemia" Int J Vitam Nutr Res. 62(3):256-260 (1992).
Obata, et al., "Eicosapentaenoic acid inhibits prostaglandin D2 generation by inhibiting cyclo-oxygenase in cultured human mast cells", Clin. & Experimental Allergy, 29:1129-1135, (1999).
O'Donnell, C.J., et al., "Leukocyte telomere length and carotid artery intimal medial thickness—the Framingham heart study." Arteriosclerosis, Thrombosis, and Vascular Biology.28:1165-1171 (2008).
Oemar BS, Tschudi MR, Godoy N, Brovkovich V, Malinski T, Luscher TF. Reduced endothelial nitric oxide synthase expression and production in human atherosclerosis. Circulation. 1998;97:2494-2498.
Oh, Robert C et al., Management of Hypertriglyceridemia, American Family Physician, LNKD-PUBMED: 17508532, vol. 75, No. 9, pp. 1365-1371 (2007).
Ohara Y, Peterson TE, Harrison DG. Hypercholesterolemia increases endothelial superoxide anion production. J. Clin. Invest. 1993;91:2546-2551.
Okuda, Y. et al., Eicosapentaenoic acid enhances nitric oxide production by cultured human endothelial cells. Biochem. Biophys. Res. Commun. 232: 487-491 (1997).
Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).
Okumura, T., et al., "Eicosapentaenoic acid improves endothelial function in hypertriglyceridemic subjects despite increased lipid oxidizability." Am J Med Sci 324(5):247-253 (2002).
Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126, 261-268 (1992).
Olofsson et al., "Apolipoprotein B: a clinically important apolipoprotein which assembles atherogenic lipoproteins and promotes the development of atherosclerosis" Journal of Internal Medicine, 258: 395-410 (2005).
OMACOR® Prescribing Information (Omega-3-acid ethyl esters, capsules) (2004). (9 pages).
Omacor®, Physicians' Desk Reference 2735 (60th ed. 2006)(3 pages).
Ona, V.O., et al., NATURE, vol. 399, Inhibition of caspase-1 slows disease progression in a mouse model of Huntington's disease, pp. 263-267 (1999).
Ooi EM, "Apolipoprotein C-III: Understanding an emerging cardiovascular risk factor", Clin.Sci. (London), vol. 114, pp. 611-624 (2008).
Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003)(2 pages).
O'Riordan, "DHA and EPA have differential effects on LDL-cholsterol," May 24, 2011 [online][Retrieved on Aug. 21, 2015] Retrieved from website: http://www.medscape.com/viewarticle/743305 (2 pages).
Osher et al., "Omega-3 Eicosapentaenoic Acid in Bipolar Depression: Report of a Small Open-Label Study," J. Clin. Psych. 66:726-729 (2005).
Ou Z, Ou J, Ackerman AW, Oldham KT, Pritchard KA, Jr. L-4f, an apolipoprotein a-1 mimetic, restores nitric oxide and superoxide anion balance in low-density lipoprotein-treated endothelial cells. Circulation. 2003;107:1520-1524.
Ozaki M, Kawashima S, Yamashita T, Hirase T, Namiki M, Inoue N, Hirata K, Yasui H, Sakurai H, Yoshida Y, Masada M, Yokoyama M. Overexpression of endothelial nitric oxide synthase accelerates atherosclerotic lesion formation in apoe-deficient mice. J. Clin. Invest. 2002; 110:331-340.
Ozawa, Akio, Nakamura E, Jinbo H. Fujita T, Hirai A, Terano T, Hamazaki T et al., "Determination of highger fatty acids in various lipid fractions of human plasma, platelets, and erythrocyte membrane using thin layer chromatography and gas chromatography," Bunseki Kagaku, 32:174-8 (1982) (with English abstract).
Padgett et al., "Phylogenetic and immunological definition of four lipoylated proteins from Novosphingobium aromaticivorans, implications for primary biliary cirrhosis," Journ. Autoimmunity 24:209-219 (May 2005).
Park JH, Park DI, Kim HJ, et al. Metabolic syndrome is associated with erosive esophagitis. World J. Gastroenterol. Sep. 14, 2008 (35): 5442-7.
Park JY, Kim KA, Kang MH, Kim SL, Shin JG. Effect of rifampin on the pharmacokinetics of rosiglitazone in healthy subjects. Clin. Pharmacol. Ther. 2004;75:157-162.
Park, Y. et al., "Omega-3 fatty acid supplementation accelerates chylomicron triglyceride clearance." J. Lipid Res. 44:455-463 (2003).
Patel et al., "Rosiglitazone monotherapy improves glycaemic control in patients with type 2 diabetes: a twelve-week, randomized, placebo-controlled study," Diabetes, Obesity and Metabolism, vol. 1, pp. 165-172 (1999).
Paton, CM, Ntambi, JM., Biochemical and physiological function of stearoyl-CoA desaturase, Am. J. Physiol. Endocrinol. Metab. 2009;297:E28-E37.
PCT/GB00/00164 International Search Report dated Oct. 20, 2000 (8 pages).
PCT/US2011/062247 International Search Report and Written Opinion dated Jun. 14, 2012 (12 pages).

(56) References Cited

OTHER PUBLICATIONS

PCT/US2013/020526 International Search Report dated Mar. 29, 2013 (2 pages).
PCT/US2013/048241 International Search Report dated Dec. 13, 2013 (3 pages).
PCT/US2013/048516 International Search Report dated Dec. 20, 2013 (3 pages).
PCT/US2013/048559 International Search Report dated Dec. 13, 2013 (3 pages).
PCT/US2013/068647 International Search Report and Written Opinion dated May 13, 2014 (18 pages).
PCT/US2014/019454 International Search Report and Written Opinion dated Jun. 3, 2014 (12 pages).
Pedersen RS, Damkier P, Brosen K. The effects of human CYP2C8 genotype and fluvoxamine on the pharmacokinetics of rosiglitazone in healthy subjects. Br. J. Clin. Pharmacol. 2006;62:682-689.
Pedersen, T., et al., "Randomised trial of cholesterol lowering in 4444 patients with coronary heart disease: the Scandinavian Simvastation Survival Study (4S)", The Lancet, No. 19, vol. 344, 8934, p. 1383-1389 (1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919, (2002).
Peet, M., et al., Phospholipid Spectrum Disorder in Psychiatry pp. 1-19, (1999).
Pejic et al., "Hypertriglyceridimia," Journ. Amer. Board Fam. Med., vol. 19(3):310-316 (2006).
P.ennathur S, Heinecke JW. Mechanisms for oxidative stress in diabetic cardiovascular disease. Antioxid. Redox Signal. 2007;9(7):955-969.
Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358 (1998).
Piche, "Tumor Necrosis Factor-Alpha, and Fibrinogen to Abdominal Adipose Tissue, Blood Pressure, and Cholesterol and Triglyceride Levels in Healthy Postmenopausal Women", American Journal of Cardiology, 2005, 96(1), 92-97.
Pike, NB, "Flushing out the role of GPR109A (HM74V) in the clinical efficacy of nicotinic acid", J. Clin. Invest., 115:3400-3403, (2005).
PLUSEPA® Product brochure "Super Critically" Different from Other Omega-3 Fish Oil Supplements for Depression and ADHD, by Minami Nutrition (Apr. 2009, pp. 1-6).
Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).
Press Release: Amarin Corporation Says Huntington's Diease Drug Failed in Trials, http://www.fiercebiotech.com/node/6607/print (Apr. 24, 2007) (Printed on Aug. 22, 2008)(2 pages).
Pritchard KA, Ackerman AW, Ou J, Curtis M, Smalley DM, Fontana JT, Stemerman MB, Sessa WC. Native low-density lipoprotein induces endothelial nitric oxide synthase dysfunction: Role of heat shock protein 90 and caveolin-1. Free Radic. Biol. Med. 2002;33:52-62.
Pritchard KA, Jr., Groszek L, Smalley DM, Sessa WC, Wu M, Villalon P, Wolin MS, Stemerman MB. Native low-density lipoprotein increases endothelial cell nitric oxide synthase generation of superoxide anion. Circ. Res. 1995;77:510-518.
Pun et al., "Reduction in Cerebral Atrophy Associated with Ethyl-eicosapentaenoic Acid Treatment in Patients with Huntington's Disease," Journ. Int'l. Med. Research, 36:896-905 (Sep.-Oct. 2008).
Pun, B., et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (2001).
Pun, B., et al., Archives of General Psychiatry, No. 55, "Sustained remission of positive and negative symptoms of schizophrenia following treatment with eicosapentaenoic acid," pp. 188-189, (1998).
Puri, B.K., et al., "Ethyl-EPA in Huntington Disease: A Double-Blind, Randomized, Placebo-Controlled Trial", Neurology, 65:286-292, (2005).
Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).
Rader, Lipid Disorders, in Eric J. Topol (ed.)Textbook of Cardiovascular Medicine pp. 55-75 (2007).
Rahimy M, Hallen B, Narang P. Effect of tolterodine on the anticoagulant actions and pharmacokinetics of single-dose warfarin in healthy volunteers. Arzneimittelforschung 2002 52 (12): 890-5.
Raitt, M.H., et al., "Fish oil supplementation and risk of ventricular tachycardia and ventricular fibrillation in patients with implantable defibrillators—a randomized controlled trial." JAMA. 293(23):2884-2891 (2005).
Rambjor, Gro S., et al., "Elcosapentaenoic Acid is Primarily Responsible for Hypotrigylceridemic Effect of Fish Oil in Humans", Fatty Acids and Lipids from Cell Biology to Human Disease: Proceedings of the 2nd international Congress of the Issfal (International Society for the Study of Fatty Acids and Lipids, AOCS Press, 31:S-45-S-49, (1996).
Randomised trial of cholesterol lowering in 4444 patients with coronary heart disease. The Scandinavian Simvastatin Survival Study, Lancet. 344: 1383-1389 (1994).
Rao MN, Mullangi R, Katneni K, et al. Lack of effect of sucralfate on the absorption and pharmacokinetics of rosiglitazone. J. Clin. Pharmacol. 2002;42:670-675.
Rees DD, Palmer RM, Moncada S. The role of endothelium-derived nitric oxide in the regulation of blood pressure. Proc. Natl. Acad. Sci. USA. 1989;86:3375-3378.
Reich, "Formulation and physical properties of soft capsules," Pharmaceutical capsules. (2004) Chapter 11:201-212.
Reiffel, J.A., et al., "Antiarrhythmic effects of omega-3 fatty acids." Am J Cardiol 98:50i-60i (2006).
Reiner Z, Catapano AL, De BG, et al. ESC/EAS Guidelines for the management of dyslipidaemias: the Task Force for the management of dyslipidaemias of the European Society of Cardiology (ESC) and the European Atherosclerosis Society (EAS). Eur. Heart J. 2011;32:1769-1818.
Richter, Werner O., "Hypertriglyceridamie: Ein klinischer•Leitfaden," Wissenschaftliche Verlagsgesellschaft mbH Stuttgart, front page to p. V, pp. 2 to 55, 64 to 85, 90 to 97 (2008) (with English Summary).
Ridker, "C-Reactive Protein : A Simple Test to Help Predict Risk of Heart Attack and Stroke", Circulation: Journal of the American Heart Association, 2003, 108, e81-e85.
Riediger, N.D., et al., "A systemic review of the roles of n-3 fatty acids in health and disease." J Am Diet Assoc. 109:668-679. (2009).
Rifai, "High-Sensitivity C-Reactive Protein: A Novel and Promising Marker of Coronary Heart Disease", Clinical Chemistry, 2001, 47(3), 403-411.
Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).
Rissanen et al., "Fish Oil-Derived Fatty Acids, Docosahexaenoic Acid and Docosapentaenoic Acid, and the Risk of Acute Coronary Events the Kuopio Ischaemic Heart Disease Risk Factor Study," Circulation. (Nov. 28, 2000)(102):2677-2679 doi:10.1161/01.CIR. 102.22.2677.
Rizzo M, Bemeis K. Low-density lipoprotein size and cardiovascular risk assessment. Q. J. Med. 2006;99(1): 1-14.
Roach, P.D., et al., "The effects of dietary fish oil on hepatic high density and low density lipoprotein receptor activities in the rat." FEBS Lett., 222: 159-162 (1987).
Robinson, J.G., et al., "Meta-analysis of the relationship between non-high-density lipoprotein cholesterol reduction and coronary heart risk." J Am Coll Cardiol., 53: 316-322 (2009).

(56) References Cited

OTHER PUBLICATIONS

Roche, H.M., et al., "Effect of long-chain n-3 polyunsaturated fatty acids on fasting and postprandial triacylglycerol metabolism." Am J Clin Nutr 71:232S-7S (2000).
Roche, H.M., et al., "Long-chain n-3 polyunsaturated fatty acids and triacylglycerol metabolism in the postprandial state." Lipids 34: S259-S265 (1999).
Rodriguez, Y., et al., "Long-chain ω36 polyunsaturated fatty acids in erythrocyte phospholipids are associated with insulin resistance in non-obese type 2 diabetics." Clinica Chimica Acta 354:195-199 (2005).
Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).
Rost KL, Roots I. Nonlinear kinetics after high-dose omeprazole caused by saturation of genetically variable CYP2C19. Hepatology Jun. 1996 23 (6): 1491-7.
Rubins, HB, et al., "Distribution of lipids in 8,500 men with coronary artery disease: Department of Veterans Affairs HDL Intervention Trial Study Group," Am. J. Cardiol, 75:1196-1201, (1995).
Rubins, HB, et al., "Gemfibrozil for the prevention of coronary heart disease in men with low levels of high-density lipoprotein cholesterol: Veterans Affairs HDL-C Intervention Trial Study Group", N. Eng. J. Med., 341:410-418, (1999).
Ruiz-Narváez, E.A., et al., "Abdominal obesity and hyperglycemia mask the effect of a common APOC3 haplotype on the risk of myocardial infarction." Am J Clin Nutr 87:1932-8 (2008).
Ruocco MJ, Shipley GG. Interaction of cholesterol with galactocerebroside and galactocerebroside phosphatidylcholine bilayer membranes. Biophys. J. 1984;46:695-707.
Rustan, A.C., et al., "Eicosapentaenoic acid inhibits cholesterol esterification in cultured parenchymal cells and isolated microsomes from rat liver." J. Bio. Chem. 263(17):8126-32 (1988).
Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).
Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).
Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).
Ryan, A.S., et al., "Clinical overview of algal-docosahexaenoic acid: effects on triglyceride levels and other cardiovascular risk factors." Am J Ther., 16:183-192 (2009).
Sacks, Frank M., "The apolipoprotein story," Atherosclerosis Supplements, 23-27 (2006).
Saito et al., "Effects of EPA on coronary artery disease in hypercholesterolemic patients with multiple risk factors: Sub-analysis of primary prevention cases from the Japan EPA Lipid Intervention Study (JELIS)," Atherosclerosis, 200:135-140 (2008).
Saito et al., "Results of Clinical Usage of Improved Formulation (MND-21S) Epadel Capsule 300 with Respect to Hyperlipidemia," 26(12) Jpn. Pharmacol. Ther. 2047-62 (1998) (with English abstract).
Saito, J., et al., "Mechanisms of enhanced production of PGI2 in cultured rat vascular smooth muscle cells enriched with eicosapentaenoic acid." Atherosclerosis 131: 219-228 (1997).
Sampath H, Ntambi JM., Role of stearoyl-CoA desaturase in human metabolic disease, Future Lipidol. 2008;3.163-73.
Sampath H, Ntambi JM., The Role of stearoyl-CoA desaturase in obesity, insulin resistance, and inflammation, Ann. NY. Acad. Sci. 2011; 1243:4 7-53.
Samuels, Martin A., M. D., et al., "Huntington's Disease", Office Practice of Neurology, (122):654-655, (1996).

Sanders, A. Hinds and C.C. Pereira, "Influence of n-3 fatty acids on blood lipids in normal subjects" Journal of Internal Medicine. 225:99-104,(1989).
Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (2006).
Sanders, T.A., et al., "Effect of varying the ratio of n-6 to n-3 fatty acids by increasing the dietary intake of a-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).
Sanders, T.A., et al., "Triglyceride-lowering effect of marine polyunsaturates in patients with hypertriglyceridemia." Arterioscler. Thromb. Vasc. Biol. 5:459-465 (1985).
Sasaki J, Miwa T, Odawara M. Administration of highly purified eicosapentaenoic acid to statintreated diabetic patients further improves vascular function. Endocr. J. 2012;59:297-304.
Sasaki J, Yokoyama M, Matsuzaki M, et al. Relationship between coronary artery disease and non-HDL-C, and effect of highly purified EPA on the risk of coronary artery disease in hypercholesterolemic patients treated with statins: sub-analysis of the Japan EPA Lipid Intervention Study (JELIS). J. Atheroscler. Thromb. 2012;19:194-204.
Sasaki, Y.F., et al., "Bio-anticlastogenic effects of unsaturated fatty acids included in fish oil—docosahexaenoic acid, docosapentaenoic acid, and eicosapentaenoic acid in cultured Chinese hamster cells." Mutation Research, 320: 9-22 (1994).
Sato et al., "General Pharmacological Studies on 5 8 11 14 17 Eicosapentaenoic Acid Ethyl Ester EPA-E", Folia Pharmacol JPN, 94 (1), 35-47. (1989) (with English abstract).
Sato, "Effects of Highly Purified Ethyl All-cis-5,8,11,14,17-icosapentaenoate (EPA-E) on Rabbit Platelets," Biol. Pharm. Bull., 16(4)362-367 (1993).
Satoh et al., "Highly purified eicosapentaenoic acid reduces cardio-ankle vascular index in association with decreased serum amyloid A-LDL in metabolic syndrome," Hypertension Research (2009) (32):1004-1008.
Satoh, N., et al., "Purified eicosapentaenoic acid reduces small dense Ldl, remnant lipoprotein particles, and C-reactive protein in metabolic syndrome." Diabetes Care, 30(1): 144-146 (2007).
Satoh-Asahara N, Shimatsu A, Sasaki Y, Nakaoka H, Himeno A, Tochiya M, Kono S, Takaya T, Ono K, Wada H, Suganami T, Hasegawa K, Ogawa Y., "Highly purified eicosapentaenoic acid increases interleukia-10 levels of peripheral blood monocytes in obese patients with dyslipidemia." Diabetes Care. 2012;35(12):2631-2639.
Schaefer, E.J., et al., "Effects of eicosapentaenoic acid, docosahexaenoic acid, and olive oil on cardiovascular disease risk factors [abstract 20007]." Circulation, 122:A20007 (2010) (Abstract only).
Schectman, G. & Hiatt, J., "Drug therapy for hypercholesterolemia in patients with cardiovascular disease: factors limiting achievement of lipid goals", Am. J. Med., 100:197-204, (1996).
Schectman, G., et al., "Dietary fish oil decreases low-density-lipoprotein clearance in nonhuman primates." Am J Clin Nutr., 64:215-221 (1996).
Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).
Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).
Schmitz PG, McCloud LK, Reikes ST, et al. Prophylaxis of hemodialysis graft thrombosis with fish oil: double-blind, randomized, prospective trial. J. Am. Soc. Nephrol. Jan. 2002 13 (1): 184-90.
Schmitz, G., et al., "The opposing effects of n-3 and n-6 fatty acids." Progress in Lipid Research, 47:147-155 (2008).
Schreiner et al., Lipoprotein[a] as a Risk Factor for Preclinical Atherosclerosis, 13 Atherosclerosis, Thrombosis & Vascular Biology 826, 826 (1993).

(56) References Cited

OTHER PUBLICATIONS

Schuirmann, D.J. A comparison of the two one-sided tests procedure and the power approach for assessing the equivalence of average bioavailability. J. Pharmacokinet. Biopharm. 15, 657-680 (1987).

Schwarz, S., et al., "Lycopene inhibits disease progression in patients with benign prostate hyperplasia." J. Nutr. 138: 49-53 (2008).

Schwellenbach et al., "The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides." J. Am. Coll. Nutr. 25(6):480-485 (2006).

Segrest et al., Structure of Apolipoprotein B-100 in Low Density Lipoproteins, J. Lipid Res. 42(9):1346-1367 (2001).

Self-Medlin Y, Byun J, Jacob RF, Mizuno Y, Mason RP. Glucose promotes membrane cholesterol crystalline domain formation by lipid peroxidation. Biochim. Biophys. Acta. 2009; 1788(6): 1398-1403.

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Sevanian A, F. Ursini Lipid peroxidation in membranes and low-density lipoproteins: similarities and differences. Free Radic. Biol. Med. 2000;29(3-4):306-311.

Shah, S. et al., "Eicosapentaenoic Acid (EPA) as an Adjunct in the Treatment of Schizophrenia", Schizophrenia Research, vol. 29, No. 1/02 (1998).

Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).

Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (2003).

Shimizu, H., et al., "Long-term effect of eicosapentaenoic acid ethyl (EPA-E) on albuminuria of non-insulin dependent diabetic pateints." Diabeters Research and Clinical Practice 28: 35-40 (1995).

Shimokawa H, Flavahan NA, Vanhoutte PM. Loss of endothelial pertussis toxin-sensitive g protein function in atherosclerotic porcine coronary arteries. Circulation. 1991;83:652-660.

Shinozaki K. et al., "The long-term effect of Eicosapentaenoic acid on serum levels of lipoprotein (a) and lipids in patients with vasciular disease" J Atheroscler Thromb. 2(2):207-9 (1996).

Shishehbor MH, Brenna ML, Aviles RJ, Fu X, Penn MS, Sprecher DL, Hazen SL. Statins promote potent systemic antioxidant effects through specific inflammatory pathways. Circulation. 2003;108(4):426-431.

Sicherer et al., "Prevalence of seafood allergy in the United States determined by a random telephone survey," J. Allergy Clin. Immunol., 114(1):159-165 (Jul. 2004).

Sierra, S., et al., "Dietary eicosapentaenoic acid and docosahexaenoic acid equally incorporate as decosahexaenoic acid but differ in inflammatory effects." Nutrition 24: 245-254 (2008).

Silvers, Karen M., et al., "Randomised double-blind placebo-controlled trial of fish oil in the treatment of depression", Prostagandins, Leukotrienes and Essential Fatty Acids, 72:211-218, (2005).

Simoens, C.M., et al., "Inclusion of 10% fish oil in mixed medium-chain triacylglycerol-long chain triacylglycerol emulsions increases plasma triacylglycerol clearance and induces rapid eicosapentaenoic acid (20:5n-3) incorporation into blood cell phospholipids." Am J Clin Nutr 88: 282-8 (2008).

Simon, Joel A., et al., "Serum Fatty Acids and the Risk of Coronary Heart Disease", American Journal of Epidemiology, 142(5):469-476, (1995).

Simopolous, The Importance of the Omega-6/Omega-3 Fatty Acid Ratio in Cardiovascular Disease and Other Chronic Diseases, Exp. Biol. Med, 233:674-688 (Apr. 11, 2008).

Simopoulos, "Omega-3 fatty acids in health and disease and in growth and development," Am. J. Clin. Nutr. 54:438-63 (1991).

Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005).

Singh, R.B., et al., "Randomozed double-blind, placebo-controlled trial of fish oil and mustard oil in patients with suspected acute myocardial infarction: the Indian experiment of infarct survival-4." Cardiovascular Drugs and Therapy 11:485-491 (1997).

Sidon, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).

Skinner JS, Cooper A, & Feder GS and on behalf of the Guideline Development Group. "Secondary prevention for patients following a myocardial infarction; summary of NICE guidance," Heart, 93:862-864 (2007).

Slides for the Oct. 16,2013 Meeting of the Endocrinologic and Metabolic Drugs Advisory Committee, (158 pages).

Smith et al., Pharmacokinetics and Pharmacodynamics of Epoetin Delta in Two Studies in Health Volunteers and Two Studies in Patients with Chronic Kidney Disease, Clinical Therapeutics/vol. 29, pp. 1368-1380 (2007).

Sniderman A, Kwiterovich PO. Update on the detection and treatment of atherogenic low-density lipoproteins. Curr. Opin. Endocrinol. Diabetes Obes. Apr. 20, 2013;20:140-147.

Sohma, R., et al., "Protective effect of n-3 polyunsaturated fatty acid on primary culture of rat hepatocytes without glycemic alterations." Journal of Gastroenterology and Hepatology 22: 1965-1970 (2007).

Spector, A.A., "Arachidonic acid cytochrome P450 epoxygenase pathway." Journal of Lipid Research, 50: S52-S56 (2009) (published online on Oct. 23, 2008.).

Spector, A.A., et al., "Epoxyeicosatrienoic acids (EETs): metabolism and biochemical function." Progress in Lipid Research 43: 55-90 (2004).

Springer, T.A., "Traffic signals for lymphocyte recirculation and leukocyte emigration: The multistep paradigm." Cell, 76: 301-314 (1994).

Squires, RW, et al., "Low-dose, time release nicotinic acid: effects in selected patients with low concentrations of high density lipoprotein cholesterol", Mayo Clinic Proc., 67:855-860, (1992).

Srinivas, et al., "Controlled release of lysozyme from succinylated gelatin microspheres," J. Biomater. Sci., Polymer Ed., vol. 12(2):137-148 (2001).

Stalenhoef, A.F.H., et al., "The effect of concentrated n-3 fatty acids versus gemfibrozil on plasma lipoproteins, low density lipoprotein heterogeneity and oxidizability in patients with hypertriglyceridemia." Atherosclerosis 153: 129-138 (2000).

Stampfer MJ, Krauss RM, Ma J, et al. A prospective study of trig lyceride level lowdensity lipoprotein particle diameter, and risk of myocardial infarction. JAMA. 1996;276:882-888.

Stancu et al., "Statins: Mechanism of Action and Effects," *Journal of Cellular and Molecular Medicine* (Oct.-Dec. 2001), 5(4), 378-387.

Stark, K.D. & Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (2004).

Stark, K.D., "The percentage of n-3 highly unsaturated fatty acids in total HUFA as a biomarker for omega-3 fatty acid status in tissues." Lipids 43:45-53 (2008).

Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).

Stein et al., "Effect of Statin Therapy on Remnant Lipoprotein Cholesterol Levels in Patients with Combined Hyperlipidemia," Arteriosclerosis, Thrombosis and Vascular Biology, vol. 21, pp. 2026-2031(Dec. 2001).

(56) References Cited

OTHER PUBLICATIONS

Steinberg D, Witztum JL. Is the oxidative modification hypothesis relevant to human atherosclerosis? Do the antioxidant trials conducted to date refute the hypothesis? Circulation. 2002;105:2107-2111.
Steinberg D. Lewis A. Conner Memorial Lecture: Oxidative modification of LDL and atherogenesis. Circulation. 1997;95(4):1062-1071.
Stepp DW, Ou J, Ackerman AW, Welak S, Klick D, Pritchard KA, Jr. Native ldl and minimally oxidized ldl differentially regulate superoxide anion in vascular endothelium in situ. Am. J. Physiol. 2002;283:H750-H759.
Sternbach "The Glasgow Coma Scale." The Journal of Emergency Medicine, 19(1):67-71 (Feb. 8, 2000).
Stiles, FDA approves EPA-only omega-3 PUFA capsule for high TG, http://www.medscape.com/viewarticle/791268, accessed Dec. 17, 2014 (1 page).
Stojancevic et al., "The impact of farnesoid X receptor activation on intestinal permeability in inflammatory bowel disease," Can. J Gastroenterol. 26(9):631-637 (2012).
Stoll, Andrew L. et al., "Omega 3 Fatty Acids in Bipolar Disorder", Arch. Gen. Psychiatry, 56:407-412, (May 1999).
Si, Kuan-Pin, et al., "Omega-3 Fatty Acids in Major Depressive Disorder A Preliminary Double-Blind, Placebo-Controlled Trial", European Neuropsychopharmacology, 13:267-271, (2003).
Sugiyama et al., "A Comparison of the Hypotensive Effects of Eicosapentaenoic Acid Ethyl (EPA) on Three Diseases (Occluded Arteriosclerosis, Hyperlipidemia, and These Two Diseases Combined) P2-504 Abstract," Annual Meeting of the Japanese Society of Pharmaceutical Health Care and Sciences 20:473 (Nov. 2010) (with English translation)(3 pages).
Sugiyama, E., et al., "Eicosapentaenoic acid lowers plasma and liver cholesterol levels in the presence of peroxisome proliferators-activated receptor alpha." Life Sciences, 83:19-28 (2008).
Superko et al., "Lipid Management to Reduce Cardiovascular Risk: A New Strategy is Required," Circulation, 117:560-568 (2008).
Surette, M.E., et al., "Dependence on dietary cholesterol for n-3 polyunsaturated fatty acid induced changes in plasma cholesterol in the Syrian hamster." J Lipid Res., 33:263-271 (1992).
Surette, M.E., et al., "Evidence for mechanisms of the hypotriglyceridemic effect of n-3 polyunsaturated fatty, acids." Biochimica et Biophysic Acta, 1126: 199-205 (1992).
Takaki A, Umemoto S, Ono K, Seki K, Ryoke T, Fujii A, Itagaki T, Harada M, Tanaka M, Yonezawa T, Ogawa H, Matsuzaki M. Add-on therapy of epa reduces oxidative stress and inhibits the progression of aortic stiffness in patients with coronary artery disease and statin therapy: A randomized controlled study. J. Atheroscler. Thromb. 2011;18:857-866.
Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991) (with English Translation)(27 pages).
Talayero BG, Sacks FM. The role of triglycerides in atherosclerosis. Curr. Cardiol. Rep. 2011;13:544-552.
Tamura, et al., "Study of the Clinical Usefulness of Ethyl Icosapentate (MND-21) in Long-Term Treatment of Hyperlipaemic Patients." J Clin Thera & Medicines, 7:1817-1834 (1991).
Tanaka et al., "Genome-Wide Association Study of Plasma Polyunsaturated Fatty Acids in the InCHIANTI Study." PLoS Genetics 5(1):1-8 (Jan. 2009).
Tanaka et al., "Suppression of prostaglandin synthesis by arachidonic acid or eicosapentaenoic acid in a macrophage-like cell line, RAW 264.7, treated with LPS," Biol. Pharm. Bull., 22(10)1 057-7 (1999).
Tanaka et al., "Administration of high dose eicosapentaenoic acid enhances anti-inflammatory properties of high-density lipoprortein in Japanese patients with dyslipidemia," Atherosclerosis, 237(2):577-83 (Dec. 2014).
Tanaka et al., "Eicosapentaenoic Acid-Enriched High-Density Lipoproteins Exhibit Anti-Atherogenic Properties," Circ. J., doi: 10.1253/circj.CJ-17/0294. [Epub ahead of print] (Jun. 23, 2017)(6 pages).

Tanaka, K.T., et al., "Reduction in the recurrence of stroke by eicosapentaenoic acid for hypercholesterolemic patients—Subanalysis of the JELIS trial." Stroke, 39(7):2052-8 (2008).
Tatarczyk, et al., "Analysis of long-chain GJ-3 fatty acid content in fish-oil supplements," Wien Klin Wochenschr, 119/13-14: 417-422 (2007).
Tatsuno et al., Efficacy and safety of TAK-085 compared with eicosapentaenoic acid in Japanese subjects with hypertriglyceridemia undergoing lifestyle modification: The omega-3 fatty acids randomized double-blind (ORL) study, J. Clin. Lipid; vol. 7(6), pp. 615-625 (Sep. 12, 2013).
Taylor et al., "Fish allergy: fish and products thereof," Journal Food Science (2004) 69.8 R175-R180.
Taylor, A.J., et al., "Arterial Biology for the Investigation of the Treatment Effects of Reducing Cholesterol (ARBITER) 2: a double-blind, placebo-controlled study of extended-release niacin on atherosclerosis progression in secondary prevention patients treated with statins", Circulation, 110:3512-3517, (2004).
Tedgui, A., et al., "Anti-inflammatory mechanisms in the vascular wall." Circ. Res. 88:877-887 (2001).
Teissier E, Nohara A, Chinetti G, Paumelle R, Cariou B, Fruchart JC, Brandes RP, Shah A, B. Steels Peroxisome proliferator-activated receptor alpha induces NADPH oxidase activity in macrophages, leading to the generation of LDL with PPAR-alpha activation properties. Circ. Res. 2004;95(12):1174-1182.
Terano, et al., "Effect of Oral Administration of Highly Purified Eicosapentaenoic Acid on Platelet Function, Blood Viscosity and Red Cell Deformability in Healthy Human Subjects," Atherosclerosis, 46, 321-331 (1983).
Theilla, M., et al., "A diet enriched in eicosapentaenoic acid, gamma-linolenic acid and antioxidants in the prevention of new pressure ulcer formation in critically ill patients with acute lung injury: A randomized, prospective, controlled study." Clinical Nutrition 26: 752-757 (2007).
Theobald et al., "LDL Cholesterol-Raising Effect of Low-Dose Docosahexaenoic Acid in Middle-Aged Men and Women," Am. J. Clin. Nutr. 79:558-63 (2004).
Thies, F., et al., "Association of n-3 polyunsaturated fatty acids with stability of atherosclerotic plaques: a randomised controlled trial." Lancet 361: 477-85 (2003).
Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).
Third Report of the NCEP Expert Panel on Detection, Evaluation, and Treatment of High Blood Cholesterol in Adults (Adult Treatment Panel III) Final Report, NIH Publication No. 02-5215 Sep. 2002 (220 paegs in three parts).
Thorwest M, Balling E, Kristensen SD, et al. Dietary fish oil reduces microvascular thrombosis in a porcine experimental model. Thromb. Res. Jul. 2000 99 (2): 203-8.
Tilg H, Moschen AR. Inflammatory Mechanisms in the Regulation of Insulin Resistance. Mol. Med. 2008;14(3-4):222-231.
Tirosh et al., "Changes in Triglyceride Levels and Risk for Coronary Heart Disease in Young Men," American College of Physicians, pp. 377-385 (2007).
Torrejon, C. et al., "n-3 Fatty acids and cardiovascular disease: Actions and molecular mechanisms," Prostaglandins Leukotrienes & Essent. Fatty Acids, doi:10.1016/j.plefa.2007.10.014 (2007).
Transcript from Oct. 16, 2013 Meeting of the Endocrinologic and Metabolic Drugs Advisory Committee, 76 pages.
TREND-HD Investigators, Randomized controlled trial of ethyl-eicosapentaenoic acid in Huntington disease: the TREND-HD study, Arch Neurol., vol. 65(12): 1582-9 (2008).
Tribble DL, Holl LG, Wood PD, Krauss RM. Variations in oxidative susceptibility among six low density lipoprotein subfractions of differing density and particle size. Atherosclerosis. 1992;93(3):189-199.
Tribble DL, Rizzo M, Chait A, Lewis DM, Blanche PJ, Krauss RM. Enhanced oxidative susceptibility and reduced antioxidant content of metabolic precursors of small, dense low-density lipoproteins. Am. J. Med. 2001;110(2):103-110.
Trilipix Package Insert (Sep. 2010)(10 pages).

(56) References Cited

OTHER PUBLICATIONS

Tsimikas S, Witztum JL, Miller ER, Sasiela WJ, Szarek M, Olsson AG, Schwartz GG. High-dose atorvastatin reduces total plasma levels of oxidized phospholipids and immune complexes present on apolipoprotein B-1 00 in patients with acute coronary syndromes in the MIRACL trial. Circulation. 2004;110(11):1406-1412.
Tsuruta K., et al., "Effects of purified eicosapentaenoate ethyl ester on fibriolytic capacity in patients with stable coronary artery disease and lower extremity ischaemia" Coron Artery Dis. 7(11):837-42 (Nov. 1996).
Tulenko TN, Chen M, Mason PE, Mason RP. Physical effects of cholesterol on arterial smooth muscle membrances: Evidence of immiscible cholesterol domains and alterations in bilayer width C during atherogenesis. J. Lipid Res. 1998;39:947-956.
Tungsiripat, et al., "Dyslipidemia in HIV patients," Cleveland Clinic Journal of Medicine, v. 72, No. 12 (2005).
Turini et al., "Short-term fish oil supplementation improved innate immunity, but increased ex vivo oxidation of LDL in man—a pilot study." Eur. J. Nutr. 40:56-65 (2001).
U.S. Appl. No. 14/245,499, filed Apr. 4, 2014 (now abandoned)(43 pages).
Ullian, M.E., "Fatty acid inhibition of angiotensin II-stimulated inositol phosphates in smooth muscle cells." Am J Physiol Heart Circ Physiol (1996).
Urakaze, Masaharu, et al., "Infusion of emulsified trieicosapentaenoylglycerol into rabbits. The effects on platelet aggregation, polymorphonuclear leukocyte adhesion, and fatty acid composition in plasma and platelet phospholipids", Thromb. Res., 44(5):673-682 (1986).
Urquhart et al., "Profile of eicosanoids produced by human saphenous vein endothelial cells and the effect of dietary fatty acids," Prostaglandins Leukot. Essent. Fatty Acid, 65(1):15-22 (2001).
US Food and Drug Administration and Dept of Health and Human Services. Substances affirmed as generally recognized as safe: Menhaden Oil. Fed Register, 62:30751-30757 (1997).
Vaagenes et al., "The Hypolipidaemic Effect of EPA is Potentiated by 2- and 3-Methylation." In P. Quant & S. Eaton (eds.) Current Views of Fatty Acid Oxidation and Ketogenesis from Organelles to Point Mutations; Advances in Experimental Medicine and Biology, vol. 466, pp. 221-226 (1999).
Vaddadi, K.S., et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002).
Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).
Van Do et al., "Allergy to fish parvalbumins: Studies on the cross-reactivity of allergens from 9 commonly consumed fish," Journ. Allergy & Clin. Immunol., 16(6):1314-1320 (Dec. 1, 2005).
van Wijk et al. Rosiglitazone improves postprandial triglyceride and free fatty acid metabolism in type 2 diabetes. Diabetes Care, vol. 28, No. 4, (2005) pp. 844-849.
Varbo et al., Remnant Cholesterol as a Causal Risk Factor for Ischemic Heart Disease, J. Am. Coll. Cardiol., vol. 61(4), pp. 427-436 (2013).
Varbo et al., Remnant cholesterol as a cause of ischemic heart disease: Evidence, definition, measurement, atherogenicity, high risk patients, and present and future treatment, Pharmacol. Ther., vol. 141(3), pp. 358-67 (2014).
Vascepa [package insert], Bedminster, NJ: Amarin Pharma Inc.; Jul. 2012. (12 pages).
Vascepa [package insert]. Bedminster, NJ: Amarin Pharma Inc.; Nov. 2013. (11 pages).
Vasudevan et al., "Effective Use of Combination of Lipid Therapy", Curr. Atheroscl. Rep., vol. 8, pp. 76-84 (2006).
Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).

Velliquette et al., "Regulation of human stearoyl-CoA desaturase by omega-3 and omega-6 fatty acids: Implications for the dietary management of elevated serum triglycerides," Journal of Clinical Lipdology. (2009) 3:281-288.
Vergnani L, Hatrik S, Ricci F, Passaro A, Manzoli N, Zuliani G, Brovkovych V, Fellin R, Malinski T. Effect of native and oxidized low-density lipoprotein on endothelial nitric oxide and superoxide production : Key role of l-arginine availability. Circulation. 2000;101:1261-1266.
Vidal F, Colome C, Martinez-Gonzalez J, Badimon L. Atherogenic concentrations of native low density lipoproteins down-regulate nitric-oxide-synthase mma and protein levels in endothelial cells. Eur. J. Biochem. 1998;252:378-384.
Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).
Virani et al., "The Role of Lipoprotein-associated Phospholipase A2 as a marker for atherosclerosis" Curr. Atheroscler. Rep. 9[2]: 97-103 (2007).
Visentainer et al., "Evaluation of lipid extraction and fatty acid composition of human plasma," Rev. Bras, Hematol., Hemoter., 32(6):439-443 (Jan. 1, 2010).
Volcik, K.A., et al., "Peroxisome proliferator-activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).
Von Schacky C, Baumann K, Angerer P. The effect of n-3 fatty acids on coronary atherosclerosis: results from SCIMO, an angiographic study, background and implications. Lipids 2001 36 Suppl: S99-102.
Von Schacky, C., "A review of omega-3 ethyl esters for cardiovascular prevention and treatment of increased blood triglyceride levels." Vascular Health and Risk Management 2(3): 251-262 (2006).
Von Schacky, C., et al., "The Effect of Dietary ω-3 Fatty Acids on Cornoray Atherosclerosis: A Randomized, Double-Blind, Placebo-Controlled Trial", American College of Physicians-American Society of Internal Medicine, 130(7):554-562, (1999).
Wada, M., et al., "Enzymes and receptors of prostaglandin pathways with arachidonic acid-derived versus eicosapentaenoic acid-derived substrates and products." J. Biol. Chem. 282(31): 22254-22266 (2007).
Wagner AH, Kohler T, Ruckschloss U, Just I, Hecker M. Improvement of nitric oxide-dependent vasodilation by hmg-coa reductase inhibitors through attenuation of endothelial superoxide anion formation. Arterioscler. Thromb. Vasc. Biol. 2000;20:61-69.
Walker G, Mandagere A, Dufton C, et al. The pharmacokinetics and pharmacodynamics of warfarin in combination with ambrisentan in healthy volunteers. Br. J. Clin. Pharmacol. May 2009 67 (5): 527-34.
Walldius, G., et al., "Editorial: Rationale for using apolipoprotein B and apolipoprotein A-I as indicators of cardiac risk and as targets for lipid-lowering therapy." European Heart Journal 26, 210-212 (2005).
Walter MF, Jacob RF, Bjork RE, Jeffers B, Buch J, Mizuno Y, Mason RP. Circulating lipid hydroperoxides predict cardiovascular events in patients with stable coronary artery disease: the PREVENT study. J. Am. Coll. Cardiol. 2008;51(12):1196-1202.
Walter MF, Jacob RF, Jeffers B, Ghadanfar MM, Preston GM, Buch J, Mason RP. Serum levels of TBARS predict cardiovascular events in patients with stable coronary artery disease: A longitudinal analysis of the PREVENT study. J. Am. Coll. Cardiol. 2004;44(10):1996-2002.
Wander, R.C., et al., "Influence of long.chain polyunsaturated fatty acids on oxidation of low density lipoprotein." Prostaglandins, Leukotrienes and Essential Fatty Acids 59(2):143-151 (1998).
Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).

(56) References Cited

OTHER PUBLICATIONS

Wang, L., et al., "Triglyceride-rch lipoprotein lipolysisi releases neutral and oxidized FFAs that induce endothelial cell inflammation." J. Lipid Res. 50:204-213 (2009).
Warren, Stephen T., "The Expanding World of Trinucleotide Repeats", Science, 271:1374-1375, (1996).
Wassmann S, Laufs U, Muller K, Konkol C, Ahlbory K, Baumer AT, Linz W, Bohm M, Nickenig G. Cellular antioxidant effects of atorvastatin in vitro and in vivo. Arterioscler. Thromb. Vasc. Biol. 2002;22:300-305.
Watanabe et al., "Bile acids lower triglyceride levels via a pathway involving FXR, SHP, and SREBP-1c," J Clin Invest. 113(10): 1408-1418 (May 2004).
Watanabe, Ikuyoshi, et al., "Usefulness of EPA-E (eicosapentaenoic acid ethyl ester) in preventing neointimal formation after vascular injury", Kokyu to Junkan, 42(7):673-677 (1994) (with English summary).
Weaver, K.L., et al., "Effect of Dietary Fatty Acids on Inflammatory Gene Expression in Healthy Humans." J. Biol. Chem., 284(23): 15400-15407 (2009) (published online Apr. 9, 2009).
Webcast Information for the Oct. 16, 2013 Meeting of the Endocrinologic and Metabolic Drugs Advisory Committee, (1 page).
Weber, P. "Triglyceride-lowering effect of n-3 long chain polyunsaturated fatty acid: eicosapentaenoic acid vs. docosahexaenoic acid." Lipids 34: S269 (1999).
Wei et al., Effects of [EPA] Versus [DHA] on Serum Lipids: A Systematic Review and Meta-Analysis, 13 Current Atherosclerosis Rep. 13(6):474-483 (2011).
Westerveld H.T. et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993).
Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).
Whelan, J., et al., "Evidence that dietary arachidonic acid increases circulating triglycerides." Lipids 30, 425-429 (1995).
Wierzbicki, A.S., "Editorial: Newer, lower, better? Lipid drugs and cardiovascular disease—the continuing story." Int J Clin Pract, 61(7):1064-1067 (2007).
Wierzbicki, A.S., "Editorial: Raising HDL-C: back to the future?" Int J Clin Pract, 61(7): 1069-1071 (2007).
Williams et al., "NADPH Oxidase Inhibitors New Antihypertensive Agents?" J. Cardiovasc Pharmacol 50(1):9-16 (Jul. 1, 2007).
Willumsen, N. et al., Biochimica et Biophysica Acta. vol. 1369, "On the effect of 2-deuterium- and 2-methyl-eiocosapentaenoic acid derivatives on triglycerides, peroxisomal beta-oxidatin and platelet aggregation in rats," pp. 193-203, (1998).
Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).
Wilson Omega 3 fish oil: EPA versus DHA (Dietivity.com, 1-16) (2006).
Wilt, VM & Gumm, JG, "Isolated low high-density lipoprotein cholesterol", Ann. Pharmacol., 31:89-97, (1997).
Wink, J., et al., "Effect of very-low-dose niacin on high-density lipoprotein in patients undergoing long-term statin therapy", Am. Heart J., 143:514-518, (2002).
Witztum JL. The oxidation hypothesis of atherosclerosis. Lancet. 1994;344(8925):793-795.
Wojenski, C.M., et al., "Eicosapentaenoic acid ethyl ester as an antithrombotic agent: comparison to an extract of fish oil." Biochimica et Biophysica Acta. 1081:33-38 (1991).
Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).

Wood et al., "Carbohydrate Restriction Alters Lipoprotein Metabolism by Modifying VLDL, LDL and HDL Subraction Distribution and Size in Overweight Men," Journ. of Nutrition, 136(2):384-9 (2006).
Woodman et al., "Effects of Purified Eicosapentaenoic and Docosahexaenoic Acids on Glycemic Control, Blood Pressure, and Serum Lipids in Type 2 Diabetic Patients with Treated Hypertension", The American Journal of Clinical Nutrition: Official Journal of the American Society for Clinical Nutrition, Inc., 76(5):1007-1015 (2002).
Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).
Wu et al., "Diabetic dyslipidemia," Metabolism Clinical and Experimental, 63:1469-1479 (Dec. 2014).
Wu, W.H., et al., "Effects of docosahexaenoic acid supplementation on blood lipids, estrogen metabolism, and in vivo oxidative stress in postmenopausal vegetarian women." Eur J Clin Nutr., 60:386-392 (2006).
Xiao, Y.F., et al., "Inhibitory effect of n-3 fish oil fatty acids on cardiac Na+/Ca2+ exchenage currents in HEK2931T cells." Biochemical and Biophysical Research Communications 321: 116-123 (2004).
Xiao, Y-F., et al "Blocking effects of polyunsaturated fatty acids on Na+ channels of neonatal rat ventricular myocytes." Proc. Natl. Acad. Sci. 92: 11000-11004 (1995).
Xiao, Y-F., et al., "Fatty acids suppress voltage-gated Na+ currents in HEK293t cells transfected with the a-subunit of the human cardiac Na+ channel." Proc. Natl. Acad. Sci. 95: 2680-2685 (1998).
Xydakis, A M et al., "Combination therapy for combined dyslipidemia," American Journal of Cardiology, Nov. 20, 2002 US, vol. 90, No. 10 Suppl. 2, p. 21 K-29 K (2002).
Yacyshyn BR, Thomson AB. The clinical importance of proton pump inhibitor pharmacokinetics. Digestion 2002 66 (2): 67-78.
Yagi K. Assay for blood plasma or serum. Methods Enzymol. 1984;105:328-331.
Yamamoto, H. et al., Improvement of coronary vasomotion with Eicosapentaenoic acid does not inhibit acetylcholine-induced coronary vasospasm in patients with variant angina: Jpn Cir J. 59(9):608-16 (1995).
Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).
Yamashita et al., J. Biochem., vol. 122, No. 1, "Acyl-transferases and Transaclyases Involved in Fatty Acid Remoding of Phospholipids and Metabolism of Bioactive Lipids in Mammalian Cells", pp. 1-16 (1997).
Yamashita, N., et al., "Inhibition of natural killer cell activity of human lymphocytes by eicosapentaenoic acid." Biochem. Biophys. Res. Comm. 138(3): 1058-1067 (1986).
Yamazaki et al., "Changes in fatty acid composition in rat blood and organs after infusion of eicosapentaenoic acid ethyl ester", Biochim. Biophys. ACATA, 1128(1):35-43, (1992).
Yamazaki, et. al., "Dissolution tests by RDC method for soft gelatin capsules containing ethyl icosapentate,", Pharm. Tech. Japan, vol. 15, No. 4, pp. 595-603 Abstract (1999) (with English abstract).
Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).
Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi, 115:843-51 (1995).
Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).
Yates RA, Wong J, Seiberling M, et al. The effect of anastrozole on the single-dose pharmacokinetics and anticoagulant activity of warfarin in healthy volunteers. Br. J. Clin. Pharmacol. May 2001 51 (5): 429-35.

(56) References Cited

OTHER PUBLICATIONS

Yerram, N.R., et al., "Eicosapentaenoic acid metabolism in brain microvessel endothelium: effect on prostaglandin formation." J. Lipid Res.30:1747-1757 (1989).

Yokoyama et al., "Effects of eicosapentaenoic acid on cardiovascular events in Japanese patients with hypercholeterolemia: Rationale, design, and baseline characteristics of the Japan EPA Lipid Intervention Study (JELIS)," Amer. Heart Journal 146(4):613-620 (2003).

Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).

Yorioka, N, "Lipid-lowering therapy and coagulation/fibrinolysis parameters in patients on peritoneal dialysis," The International Journal of Artificial Organs, vol. 23(1):27-32 2000.

Yoshimura et al., "Effects of highly purified eicosapentaenoic acid on plasma beta thromboglobulin level and vascular reactivity to angiotensin II", Artery, 14(5):295-303 (1987).

Zaima, N., et al., "Trans geometric isomers of EPA decrease LXRa-induced cellular triacylglycerol via suppression of SREBP-1c and PGC-1β," J. Lipid Res. 47: 2712-2717 (2006).

Zalewski et al., Role of Lipoprotein-Associated Phospholipase A2 in Atherosclerosis: Biology, Epidemiology, and Possible Therapeutic Target, Arteriosclerosis, Thrombosis, & Vascular Biology 25(5):923-931 (2005).

Zanarini, et al., "Omega-3 Fatty Acid Treatment of Women with Borderline Personality Disorder: A Double-Blind, Placebo-Controlled Pilot Study," Am J Psychiatry, 160:167-169 (2003).

Zhan, S. et.al."Meta-analysis of the effects of soy protein containing isoflavones on the lipid profile," Am. J. Clin. Nutr. (Feb. 2005), 81, p. 397-408.

Zhang, M., et al., "Effects of eicosapentaenoic acid on the early stage of type 2 diabetic nephropathy in KKAy/Ta mice: Involvement of anti-inflammationand antioxidative stress." Metabolism Clinical and Experimental 55:1590-1598 (2006).

Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).

Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).

Zhao et al., "Polyunsaturated Fatty Acids are FXR Ligands and Differentially Regulate Expression of FXR Targets," DNA and Cell Biology, 23(8):519-526 (Aug. 2004).

Zhao, G. et al., "Dietary α-linolenic acid inhibits proinflammatory cytokine production by peripheral blood mononuclear cells in hypercholesterolemic subjects." Am J Clin Nutr 85:385-91 (2007).

Zhao, G., et al., "Dietary α-linolenic acid reduces inflammatory and lipid cardiovascular risk factors in hypercholesterolemic men and women." J. Nutr. 134: 2991-2997 (2004).

Ziegler, D., et al., "Treatment of symptomatic diabetic polyneuropathy with the antioxidant a-lipoic acid: A 7-month multicenter randomized controlled trial (ALADIN III Study)." Diabetes Care 22:1296-1301 (1999).

Zimmerman JJ, Raible DG, Harper DM, et al. Evaluation of a potential tigecycline-warfarin drug interaction. Pharmacotherapy Jul. 2008 28 (7): 895-905.

Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, pp. 89-100 (2000).

Zuijdgeest-van Leeuwen, S.D., et al., "Incorporation and washout of orally administered n-3 fatty acid ethyl esters in different plasma lipid fractions." British Journal of Nutrition 82:481-488 (1999).

Zuijdgeest-van Leeuwen, SD, et al., "Eicosapentaenoic acid inhibits lipolysis in weight-losing cancer patients as well as in healthy volunteers," Eur J Gastroenterol & Hepatol., 10(12):A67 (1998).

Zvyaga T, Chang SY, Chen C, et al. Evaluation of six proton pump inhibitors as inhibitors of various human cytochromes P450: focus on cytochrome P450 2C19. Drug Metab. Dispos. Sep. 2012 40 (9): 1698-711.

Amarin, Next Generation Lipid Modification in Cardiovascular Disease, Investor Meetings, Nov. 2010, (http://files.shareholder.com/downloads/AMRN/0x0x417754/AA72705F-1D67-4E1D-A989-5805E5CF0244/Investor_Presentation_2010_Nov_10.pdf, accessed Jan. 6, 2015.

Astarita et al., "Targeted lipidomics strategies for oxygenated metabolites of polyunsaturated fatty acids," Biochim Biophys Acta, 1851(4):456-168 (Apr. 2015).

Harada-Shiba et al., Journal of Clinical and Experimental Medicine, Jun. 30, 2007, vol. 221, No. 13, pp. 1068-1073 (with English translation).

Maki et al., "Effects of Adding Prescription Omega-3 Acid Ehtyl Esters to Simvastatin (20 mg/day) on Lipids and Lipoprotein Particles in Men and Women with Mixed Dyslipidemia," Am. J. Cardiol., 102:429-433 (Aug. 15, 2008).

Marcoux et al., "Plasma remnant-like particle lipid and apolipoprotein levels in normolipidemic and hyperlipidemix subjects," Atherosclerosis, vol. 139, pp. 161-171 (1998).

Nippon Rinsho, Metabolic Syndrome 2nd Edition—Basics and New Clinical Findings, Jan. 20, 2011, Special Issue 1 (vol. 992), pp. 503-506 (with English translation).

Ohashi, Journal of Clinical and Experimental Medicine, Feb. 14, 2009, vol. 228, No. 7, pp. 795-805 (with English translation).

Wojczynski et al., "High-fat meal effect on LDL, HDL and VLDL particle size and number in the Genetics of Lipid-Lowering Drugs and Diet Network (GOLDN): an interventional study," Lipids in Health and Disease 10:181, pp. 1-11 (Oct. 18, 2011).

Aaresetoey H, Gurndt H, Nygaard O. The Role of Long-Chained Marine N-3 Polyunsaturated Fatty Acids in Cardiovascular Disease. Cardiol Res Pract. 2012. Epub Dec. 13, 2012.

Albert CM, Campos H, Stampfer MJ, et al. Blood Levels of Long-Chain n-3 Fatty Acids and the Risk of Sudden Death. N Engl J Med 346(15):1113-1138, 2002.

Alberti K, et. al. Harmonizing the Metabolic Syndrome: A Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity. Circulation. 120:1640-1645; 2009.

American Heart Association. Heart Disease and Stroke Statistics—2010 Update. Dallas, Texas: American Heart Association; 2010.

Anand RG, Alkadri M, Lavie CJ, Milani RV. The Role of Fish Oil in Arrhythmia Prevention. J Cardioplin Rehabil Preven. 2008;28:92-98.

Armaganijan L, Lopes RD, Healey JS, Piccini JP, Nair GN, Morillo CA. Do Omega-3 fatty acids prevent artrial fibrillation after open heart surgery? A meta-analysis of randomized controlled trials. Clinics. 2011;66(11):1923-1928.

Anderson JL, Adams CD, Antman EM, et al. ACC/AHA 2007 guidelines for the management of patients with unstable angina/non-ST-elevation myocardial infarction—executive summary. A report of the American College of Cardiology/American Heart Association Task Force on Practice Guidelines (Writing Committee to Revise the 2002 Guidelines for the Management of Patients With Unstable Angina/Non-ST-Elevation Myocardial Infarction) developed in Collaboration with the American College of Emergency Physicians, the Society for Cardiovascular Angiography and Interventions, and the Society of Thoracic Surgeons Endorsed by the American Association of Cardiovascular and Pulmonary Rehabilitation and the Society for Academic Emergency Medicine. J Am Coll Cardiol 50:652-726, 2007.

Antman E, Anbe D, Amstrong P, et al. ACC/AHA guidelines for the management of patients with ST-elevation myocardial infarction—executive summary. A report of the American College of Cardiology/American Heart Association Task Force on Practice Guidelines

(56) References Cited

OTHER PUBLICATIONS (Writing Committee to revise the 1999 guidelines for the management of patients with acute myocardial infarction). J Am Coll Cardiol 44:671-719, 2004.
Becker LB, Aufderheide TP, Geocadin RG, Callaway CW, Lazar RM, Donnino MW, Nadkarni VM, Abella BS, Adrie C, Berg RA, Merchant RM, O'Connor RE, Meltzer DO, Holm MB, Longstreth WT, Halperin HR. AHA Consensus Statement: Primary Outcomes for Resuscitation Science Studies: A Consensus Statement From the American Heart Association. Circulation 2011; CIR. 0b013e3182340239 published online before print Oct. 3 2011, doi:10.1161/CIR. 0b013e3182340239.
Burr ML, Sweetham PM, Fehily AM. Diet and reinfarction. Eur Heart J 15:1152-1153, 1994.
Calder PC. Omega-3 Fatty Acids and Inflammatory Processes. Nutrients 2(3):355-374, 2010.
Cao H, Wang X, Huang H, Ying SZ, Guy W, Wang T, Huang CX. Omega-3 Fatty Acids in the Prevention of Atrial Fibrillation Recurrences after Cardioversion: A Meta-analysis of Randomized Controlled Trials. Int Med. 2012;51:2503-2508.
Caughey GE, Mantzioris E, Gibson RA, Cleland LG, James MJ. The effect on human tumor necrosis factor α and interleukin 1β production of diets enriched in n-3 fatty acids from vegetable oil or fish oil. Am J Clin Nutr. 1996;63:116-122.
Cawood AL, Ding R, Napper FL, et al. Eicosapentaenoic acid (EPA) form highly concentrated n-3 faty acid ethyl esters is incorporated into advanced atherosclerotic plaques and higher plaque EPA is associated with decreased plaque inflammationand increased stability. Atherosclerosis. 2010;212:252-259.
Chang CL, Seo T, Du CB, Accili D, Deckelbaum RJ. n-3 Fatty Acids Decrease Arterial Low-Density Lipoprotein Cholesterol Delivery and Lipoprotein Lipase Levels in Insulin-Resistant Mice. Arterioscler Thromb Vasc Biol. 2010;30(12):2510-2517.
Citizen Petition, Pronova BioPharma Norge AS, (Aug. 4, 2009), at ii (Appendix), available at www.regulations.gov.
Costanzo S, di Niro V, Castelnuovo AD, et al. Prevention of postoperative atrial fibrillation in open heart surgery patients by preoperative supplementation of n-3 polyunsaturated fatty acids: An updated meta-analysis. Periop Manga. 2013; Apr. 12 epub.
DeMets DL, Lan KK. Interim Analysis: the Alpha Spending Function Approach. Stat Med 1994;13(13-14):1341-52.
Dewey FE, Gusarova V, O'Dushlaine C, et al. Supplement to: Inactivating variants in ANGPTL4 and risk of coronary artery disease. N Engl J Med. DOI: 10.1056/NEJMoa1510926; 2016.
Djousse L, Akinkuolie AO, Wu JHY, Ding EL, Gaziano JM. Fish consumption, omega-3 fatty acids and risk of heart failure: A meta-analysis. Clin Nutr. 2012;31:846-853.
Do R, Willer CJ, Schmidt EM, et al. Common variants associated with plasma triglycerides and risk for coronary artery disease. Nat Genet 2013;45(11):1345-52.
Do R, Stitziel NO, Won HH, et. al. Exome sequencing identifies rare LDLR and APOA5 alleles conferring risk for myocardial infarction. Nature. 2015;518(7537):102-106.
Fraker TD, Fihn SD. Writing on behalf of the 2002 Chronic Stable Angina Writing Committee. 2007 chronic angina focused update of the ACC/AHA guidelines for the management of patients with chronic stable angina. A Report of the ACC/AHA Task Force on Practice Guidelines. Circulation 50:2264-2274, 2007.
Galan P, Kesse-Guyot E, Czernichow S, et al. Effects of B vitamins and omega 3 fatty acids on cardiovascular diseases: a randomised placebo controlled trial. Br Med J. 2010;341:c6273.
Geleijnse JM, Giltay EJ, Grobbee DE, Donders ART, Kok FJ. Blood pressure response to fish oil supplementation: metaregression analysis of randomized trials. J Hypertens. 2002;20(8):1493-1499.
Gillet L, Roger S, Bougnoux P, L Guennec JY, Besson P. Beneficial effecs of omega-3 long-chain fatty acids in breast cancer and cardiovascular diseases: voltage-gated sodium channels as a common feature? Biochimi. 2011;93:4-6.

Ginsberg HN, Elam MB, Lovato LC, et al, for the ACCORD Study Group. Effects of combination lipid therapy in Type 2 diabetes mellitus. N Engl J Med 362:1563-1574, 2010.
GISSI-HF Investigators. Effect of n-3 polyunsaturated fatty acids in patients with chronic heart failure (the GISSI-HF trial): a randomised, double-blind, placebo-controlled trial. Lancet. 2008;372(9645):1223-1230.
Goff DC, Lloyd-Jones DM, Bennett G, et al. ACC/AHA Prevention Guideline: 2013 ACC/AHA Guideline on the Assessment of Cardiovascular Risk: A Report of the American College of Cardiology/ American Heart Association Task Force on Practice Guidelines. Circulation. 2014;129:S74-S75.
Harris WS. International recommendations for consumption of longchain omega-3 fatty acids. J Cardiovasc Med (Hagerstown) 8(suppl 1):550-552, 2007.
Hoogeveen EK, Geleijnse JM, Kromhout D, et al. No effect of n-3 fatty acids supplementation on NT-proBNP after myocardial infarction: the Alpha Omega Trial. Eur J Prev Cardiol. May 2015;22:648-55.
HPS2-THRIVE Collaborative Group, Landray MJ, Haynes R, et al. Effects of extended-release niacin with laropiprant in high-risk patients. N Engl J Med. 2014;371(3):203-12.
Jinno Y, Nakakuki M, Kawano H, Notsu T, Mizuguchi K, Imada K. Eicosapentaenoic acid administration attenuates the pro-inflammatory properties of VLDL by decreasing its susceptibility to lipoprotein lipase in macrophages. Atheroscler. 2011;219:566-572.
Jørgensen AB, Frikke-Schmidt R, Nordestgaard BG, Tybjwrg-Hansen A. Loss-of-function mutations in APOC3 and risk of ischemic vascular disease. N Engl J Med. 2014; 371(1):32-41.
Jun M, Foote C, Lv J, et al. Effects of fibrates on cardiovascular outcomes: a systematic review and meta-analysis. Lancet 375 (9729):1875-1884, 2010.
Khoueiry G, Rafeh NA, Sullivan E, et al. Do omega-3 polyunsaturated fatty acids reduce risk of sudden cardiac death and ventricular arrhythmias? A meta-analysis of randomized trials. Heart and Lung. 2013;42:251-256.
LaRosa JC. Understanding risk in hypercholesterolemia. Clin Cardiol 26(Suppl 1):3-6, 2003.
Leaf A, Kang JX. Prevention of cardiac sudden death by N-3 fatty acids: a review of the evidence. J Intern Med 240:5-12, 1996.
Leaf A, Albert CM, Josephson M, et al. for the atty Acid Antiarrhythmia Trail Investigators. Prevention of Fatal Arrhythmias in High-Risk Subjects by Fish Oil n-3.
Levey A, at. al. A New Equation to Estimate Glomerular Filtration Rate. Ann Intern Med. 150:604-612; 2009.
Lovaza United States Prescribing Information, GlaxoSmithKline. Research Triangle Park, USA, May 2014.
Manninen V, Tenkanen L, Koskinen P, et al. Joint effects of serum triglyceride and LDL cholesterol and Hdl cholesterol concentrations on coronary heart disease risk in the Helsinki Heart Study. Implications for treatment. Circulation 85:37-45, 1992.
Marchioli R, Barzi F, Bomba E, et al, GISSI-Prevenzione Investigators. Early protection against sudden death by n-3 polyunsaturated fatty acids after myocardial infarction: time-course analysis of the results of the Gruppo Italiano per lo Studio della Soprawivenza nell'Infarto Miocardico (GISSI)-Prevenzione. Circulation. 105(16):1897-1903, 2002.
Martin SS, Blaha MJ, Elshazly MB, et al. Comparison of a novel method vs the Friedewald equation for estimating low-density lipoprotein cholesterol levels from the standard lipid profile. JAMA. 2013;310:2061-8.
Miller M. Current perspectives on the management of hypertriglyceridemia. Am Heart J 140:232-40, 2000.
Miller M, Cannon CP, Murphy SA, et al. Impact of triglyceride levels beyond low-density lipoprotein cholesterol after acute coronary syndrome in the PROVE IT-TIMI 22 trial. J Am Coll Cardiol 51:724-730, 2008.
Mori TA. Omega-3 fatty acids and blood pressure. Cell Mol Biol. 2010; Feb. 25;56(1):83-92.
Morris M, Sacks F, Rosner B. Does fish oil lower blood pressure? A meta-analysis of controlled trials. Circ. 1993;88:523-533.

(56) References Cited

OTHER PUBLICATIONS

Mozaffarian D, Geelen A, Brouwer I, Geleijnse J, Zock P, Katan M. Effect of Fish Oil on Heart Rate in Humans a Meta-Analysis of Randomized Controlled Trials. Circ.2005; 112:1945-1952.

Mozaffarian D, Marchioli R, Macchia A, et al. Fish Oil and Postoperative Atrial Fibrillation the Omega-3 Fatty Acids for Prevention of Post-operative Atrial Fibrillation (OPERA) Randomized Trial. JAMA. Nov. 21, 2012;308(19):2001-11.

Mozaffarian D, Psaty B, Rimm E, Lemaitre R, Burke G, Lyles M, Lefkowitz D, Siscovick D. Fish Intake and Risk of Incident Atrial Fibrillation. Circ.2004; 110:368-373.

Mozaffarian D, Benajmin EJ, Go AS, Arnett DK, Blaha MJ, et al.; on behalf of the American Heart Assxoication Statistics Committee and Stroke Statistics Subcommittee. Heart desease and stroke statistics—2016 update: a report form the American Heart Association [publised online ahead of print Dec. 16, 2015]. Circulation. doi: 10.1161/CIR.000000000000350.

Needleman P, Raz A, Minkes MS, Ferrendelli JA, Sprecher H. Triene prostaglandins: prostacyclin and thromboxane biosynthesis and unique biological properties. Proc Natl Acad Sci USA. 1979;76:944-948.

Nomura S, Shouzu A, Omoto S, et al. Effects of eicosapentaenoic acid on endothelial cell-derived microparticles, angiopoietins and adiponectin in patients with type 2 diabetes. J Atheroscler Throm. 2009;16:83-90.

Omacor Summary of Product Characteristics, Pronova BioPharma Norge AS. Lysaker, Norway, Mar. 2015.

Origin Trial Investigators (The). n-3 fatty acids and cardiovascular outcomes in patients with dysglycemia. N Engl J Med 2012;367:309-318.

Pase M, Grima N, Sarris J. Do long-chain n-3 fatty acids reduce arterial stiffness? A meta-analysis of randomized controlled trials.Br J Nutr.2011; 106:974-980.

Pollin TI, Damcott CM, Shen H, et al. A null mutation in human APOC3 confers a favorable plasma lipid profile and apparent cardioprotection. Science. 2008;322(5908):1702-1705.

Rauch B, Rudolf R, Schneider S, et al. OMEGA, a randomized, placebo-controlled trial to test the effect of highly purified omega-3 fatty acids on top of modern guideline-adjusted therapy after myocardial infarction. Circulation. 2010;122:2152-2159.

Risk and Prevention Study Collaborative Group, Roncaglioni MC, Tombesi M, et al. n-3 fatty acids in patients with multiple cardiovascular risk factors. N Engl J Med. 2013;368(19):1800-8.

Sarwar N, Danesh J, Eiriksdottir G, et al. Triglycerides and the risk of coronary heart disease: 10,158 incident cases among 262,525 participants in 29 Western prospective studies. Circulation 115:450-458, 2007.

Sasaki J, Miwa T, Odawara M. Administration of highly purified eicosapentaenoic acid to stain-treated diabetic patients further improves vascular function. Endocrine J. 2012; 59(4):297-304.

Schunkert H, König IR, Kathiresan S, et al. Large-scale association analysis identifies 13 new susceptibility loci for coronary artery disease. Nat Genet. 2011;43(4):333-8.

Serhan C, Chiang N, Van Dyke T. Resolving inflammation: dual anti-inflammatory and pro-resolution lipid mediators. Nat Rev Immunol. 2008; 8:3449-361.

Stitziel N, Stirrups K, Masca N, et al. Supplement to: Coding variation in ANGPTL4, LPL, and SVEP1 and the risk of coronary disease. N Engl J Med. DOI: 1.1056/NEJMoa1507652; 2016.

Stone NJ, Robinson J, Lichtenstein AH, et al. ACC/AHA Prevention Guideline: 2013 ACC/AHA Guideline on the Treatment of Blood Cholesterol to Reduce Atherosclerotic Cardiovascular Risk in Adults: A Report of the American College of Cardiology/American Heart Association Task Force on Practice Guidelines. Circulation. 2014;129:S46-S48.

Tagawa H, Shimokawa H, Tagawa T, et al. Long-term treatment with eicosapentaenoic acid augments both nitric oxide-mediated and non-nitric oxide-mediated endothelium-dependent forearm vasodilatation in patients with coronary artery disease. J Cardiovasc Pharmacol 33(4):633-40, 1999.

Teramoto T, Sasaki J, Ishibashi S, et al. Diagnosis of atherosclerosis. Executive Summary of the Japan Atherosclerosis Society (JAS) Guidelines for the Diagnosis and Prevention of Atherosclerotic Cardiovascular Diseases in Japan—2012 Version. J Atheroscler Thromb. 2014;21(4):296-8. Electronic publication Dec. 10, 2013.

The TG and HDL Working Group of the Exome Sequencing Project, National Heart, Lung, and Blood Institute. Loss-of-function mutations in APOC3, triglycerides, and coronary disease. N Engl J Med. 2014;371(1):22-31.

Thygesen K., Alpert J., Jaffe A., et al. Third Universal Definition of Myocardial Infarction. *J Am Coll Cardiol.* 2012;60(16):1581-1598.

Varbo A, Benn M, Tybærg-Hansen A, Nordestgaard BG. Reply to letters regarding article, "Elevated remnant cholesterol causes both low-grade inflammation and ischemic heart disease, whereas elevated low-density lipoprotein cholesterol causes ischemic heart disease without inflammation". Circulation. 2014;129:e656.

Wall R, Ross RP, Fitzgerald G, Stanton C. Fatty acids from fish: the anti-inflammatory potential of long-chain omega-3 fatty acids. Nutr Rev. 2010; 68:280-289.

Wang Q, Liang X, Wang L, Lu X, Huang J, Cao J, Li H, Gu D. Effect of omega-3 fatty acids supplementation on endothelial function: A meta-analysis of randomized controlled trials. Atherosc. 2012; 221:563-543.

Wittrup HH, Tybærg-Hansen A, Nordestgaard BG. Lipoprotein lipase mutations, plasma lipids and lipoproteins, and risk of ischemic heart disease: a meta-analysis. Circulation. 1999;99:2901-2907.

Yadav D, Pitchumoni CS. Issues in Hyperlipidemic Pancreatitis. J Clin Gastroenterol 236(1):54-62, 2003.

Ymaagishi K, Nettleton J, Folsom A. Plasma fatty acid compositon and incident heart failure in middle-aged adults: The Atherosclerosis Risk in Communities (ARIC) Study. Am Heart J.2008; 156:965-974.

Yamakawa K, Shimabukuro M, Higa N, Asahi T, Ohba K, Arasaki O, Higa M, Oshiro Y, Yoshida H, Higa T, Saito T, Ueda S, Masuzaki H, Sata M. Eicosapentaenoic Acid Supplementation Changes Fatty Acid Composition and Corrects Endothelial Dysfunction in Hyperlipidemic Patients. Cardiol Res Practice. 2012; epub Article ID 754181.

Yamano T, Kubo T, Shiono Y, et al. Impact of eicosapentaenoic acid treatment on the fibrous cap thickness in patients with coronary atherosclerotic plaque: an optical coherence tomography study. J Atheroscler Thromb. 2015;22:52-61.

Epadel Summary of Product Characteristics (SPC), Mochida Pharmaceutical Co., Ltd. Tokyo, Japan, Oct. 2013.

Bhatt et al, "Cardiovascular Risk Reduction with Icosapent Ethyl for Hypertriglyceridemia," N. Eng. J. Med., Nov. 10, 2018 (epub ahead of print)(12 pages)(downloaded from nejm.org on Nov. 13, 2018 at httos://www.nejm.ord/doi/full/10.1056/NEJMoa1812792).

ASCEND Study Collaborative Group. Effects of n-3 fatty acid supplements in diabetes mellitus. N Engl J Med, 379(16):1540-1550 (publication date Oct. 18, 2018; epublication date Aug. 26, 2018).

Aung T, Halsey J, Kromhout D, et al. Associations of omega-3 fatty acid supplement use with cardiovascular disease risks: Meta-analysis of 10 trials involving 77917 individuals. JAMA Cardiol 3:225-34 (publication date Mar. 1, 2018; epublication date Jan. 31, 2018).

Bhatt DL, Eagle KA, Ohman EM, et al. Comparative determinants of 4-year cardiovascular event rates in stable outpatients at risk of or with atherothrombosis. JAMA 304(12):1350-7 (publication date Sep. 22, 2010; epublication date Aug. 30, 2010).

Bhatt DL, Fox KAA, Hacke W, et al; Charisma Investigators. Clopidogrel and aspirin versus aspirin alone for the prevention of atherothrombotic events. N Engl J Med. 354(16):1706-1717 (publication date Apr. 20, 2006; epublication date Mar. 12, 2006).

Bhatt DL, Hulot JS, Moliterno DJ, Harrington RA. Antiplatelet and anticoagulation therapy for acute coronary syndromes. Circ Res 114(12):1929-43 (publication date Jun. 6, 2014).

Bhatt DL, Steg PG, Brinton EA, et al. Rationale and design of REDUCE-IT: Reduction of Cardiovascular Events with Icosapent Ethyl-Intervention Trial. Clin Cardiol 40:138-48 (publication date Mar. 2017; epublication date Mar. 15, 2017).

(56) References Cited

OTHER PUBLICATIONS

Bhatt DL, Steg PG, Ohman EM, et al; REACH Registry Investigators. International prevalence, recognition and treatment of cardiovascular risk factors in outpatients with atherothrombosis. *JAMA*. 295(2):180-189 (publication date Jan. 11, 2006).

Cannon CP, Blazing MA, Giugliano RP, et al; IMPROVE-IT Investigators. Ezetimibe added to statin therapy after acute coronary syndromes. *N Engl J Med*. 372:2387-2397. 2015.

Cannon CP, Braunwald E, McCabe CH, et al. Intensive versus moderate lipid lowering with statins after acute coronary syndromes. N Engl J Med 350(15):1495-1504 (publication date Apr. 8, 2004; epublication date Mar. 8, 2004).

Cavender MA, Steg PG, Smith SC, et al; REACH Registry Inverstigators. Impact of diabetes mellitus on hospitalization for heart failure, cardiovascular events, and death: outcomes at 4 years from the reduction of atherothrombosis for continued health (REACH) registry. *Circulation*. 132(10):923-931 (publication date Sep. 8, 2015; epublication date Jul. 7, 2015).

Doi M, Nosaka K, Miyoshi T, et al. Early eicosapentaenoic acid treatment after percutaneous coronary intervention reduced acute inflammatory responses and ventricular arrhythmias in patients with acute myocardial infarction: A randomized controlled study. Int J Cardiol., 176(3):577-82 (publication date Oct. 20, 2014; epublication date Aug. 19, 2014).

Ganda OP, Bhatt DL, Mason RP, Miller M, Boden WE. Unmet need for adjunctive dyslipidemia therapy in hypertriglyceridemia management. J Am Coll Cardiol 72(3):330-43 (publication date Jul. 17, 2018.

Hong KN, Fuster V, Rosenson RS, Rosendorff C, Bhatt DL. How low to go with glucose, cholesterol, and blood pressure in primary prevention of CVD. J Am Coll Cardiol 70(17):2171-85 (publication date Oct. 24, 2017; epublication date Oct. 16, 2017).

Klempfner R, Erez A, Sagit BZ, et al. Elevated triglyceride level is independently associated with increased all-cause mortality in patients with established coronary heart disease: Twenty-two-year follow-up of the Bezafibrate Infarction Prevention Study and Registry. Circ Cardiovasc Qual Outcomes 9(2):100-8 (publication date Mar. 8, 2016.

Law TK, Yan AT, Gupta A, et al. Primary prevention of cardiovascular disease: global cardiovascular risk assessment and management in clinical practice. *Eur Heart J Qual Care Clin Outcomes*. 1(1):31-36 (publication date Jul. 2, 2015; epublication date Jul. 1, 2015.

Libby P. Triglycerides on the rise: should we swap seats on the seesaw? *Eur Heart J*. 36(13):774-776 (publication date Apr. 1, 2015; epublication date Dec. 29, 2014.

Murphy SA, Cannon CP, Blazing MA, et al. Reduction in total cardiovascular events with ezetimibe/simvastatin post-acute coronary syndrome. *J Am Coll Cardiol*. 67(4):353-361 (publication date Feb. 2, 2016; epublication date Jan. 25, 2016.

Nambi V, Bhatt DL. Primary prevention of atherosclerosis: Time to take a selfie? J Am Coll Cardiol 2017;70(24):2992-4 (publication date Dec. 19, 2017; epublication date Dec. 11, 2017.

Nelson JR, Wani O, May HT, Budoff M. Potential benefits of eicosapentaenoic acid on atherosclerotic plaques. Vascul Pharmacol. 91:1-9 (publication date Apr. 2017; epublication date Mar. 2, 2017).

Nichols GA, Philip S, Reynolds K, Granowitz CB, Fazio S. Increased cardiovascular risk in hypertriglyceridemic patients with statin-controlled LDL cholesterol. J Clin Endocrinol Metab 103(8):3019-27 (publication date Aug. 1, 2018; epublication date May 29, 2018).

Nichols GA, Philip S, Reynolds K, Granowitz CB, Fazio S. Increased residual cardiovascular risk in patients with diabetes and high vs. normal triglycerides despite statin-controlled LDL Cholesterol. Diabetes Obes Metab (publication date Sep. 17, 2018; epublication date Sep. 17, 2018).

Ridker PM, Everett BM, Thuren T, et al. Antiinflammatory Therapy with canakinumab for atherosclerotic disease. N Engl J Med 377(12):1119-31 (publication date Sep. 21, 2017; epublication date Aug. 27, 2017).

Roe MT, Armstrong PW, Fox KAA, et al; TRILOGY ACS Investigators. Prasugrel versus clopidogrel for acute coronary syndromes without revascularization. *N Engl J Med*. 367(14):1297-1309 (publication date Oct. 4, 2012; epublication Aug. 25, 2012).

Schwartz GG, Bessac L, Berdan LG, et al. Effect of alirocumab, a monoclonal antibody to PCSK9, on long-term cardiovascular outcomes following acute coronary syndromes: rationale and design of the Odyssey outcomes trial. Am Heart J 168(5):682-9 (publication date Nov. 2014, epublication date Aug 7, 2017).

Sherratt SCR, Mason RP. Eicosapentaenoic acid and docosahexaenoic acid have distinct membrane locations and lipid interactions as determined by X-ray diffraction. Chem Phys Lipids 212:73-9 (publication date May 2018, epublication date Jan. 31, 2018).

Steg PG, Bhatt DL, Wilson PWF, et al; REACH Registry Investigators. One-year cardiovascular event rates in outpatients with atherothrombosis. JAMA. 297(11):1197-1206 (publication date May 21, 2007).

Toth PP, Granowitz C, Hull M, Liassou D, Anderson A, Philip S. High Triglycerides are associated with increased cardiovascular events, medical costs, and resource use: A real-world administrative claims analysis of statin-treated patients with high residual cardiovascular risk. Journal of the American Heart Association, 7(15):e008740 (publication date Jul. 25, 2018; epublication Aug. 7, 2018).

Vaduganathan M, Venkataramani AS, Bhatt DL. Moving toward global primordial prevention in cardiovascular disease: The heart of the matter. J Am Coll Cardiol 2015;66(14):1535-7.

Verma S, Leiter LA, Bhatt DL. CANTOS ushers in a new calculus of inflammasome targeting for vascular protection—and maybe more. Cell Metab 26(5):703-5 (publication date Nov. 7, 2017, epublication date Oct. 19, 2017).

Watanabe T, Ando K, Daidoji H, et al. A randomized controlled trial of eicosapentaenoic acid in patients with coronary heart disease on statins. J Cardiol 70(6):537-44 (publication date Dec. 2017; epublication date Aug. 31, 2017).

Wei LJ, Lin DY, Weissfeld L. Regression analysis of multivariate incomplete failure time data by modeling marginal distributions. *J Am Stat Assoc*. 84(408):1065-1073 (publication date Dec. 1989).

METHODS OF REDUCING THE RISK OF A CARDIOVASCULAR EVENT IN A SUBJECT ON STATIN THERAPY

PRIORITY CLAIM

This application is a continuation of U.S. patent application Ser. No. 16/005,852 filed Jun. 12, 2018, which is a continuation of U.S. patent application Ser. No. 15/886,422 filed Feb. 1, 2018, which is a continuation application of U.S. patent application Ser. No. 15/607,084 filed May 26, 2017 (now U.S. Pat. No. 9,918,955), which is a continuation of U.S. patent application Ser. No. 15/427,238 filed Feb. 8, 2017 (now U.S. Pat. No. 9,693,986), which is a continuation application of U.S. patent application Ser. No. 15/333,991 filed Oct. 25, 2016 (now U.S. Pat. No. 9,610,272), which is a continuation of U.S. patent application Ser. No. 14/411,815, filed Dec. 29, 2014 (now U.S. Pat. No. 9,603,826), which is a 371 national stage application of PCT/US2013/048559 filed Jun. 28, 2013, and which claims priority to U.S. provisional patent application Ser. No. 61/666,447, filed Jun. 29, 2012, the entire contents of which are incorporated herein by reference.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke.

Lovaza®, a lipid regulating agent, is indicated as an adjunct to diet to reduce triglyceride levels in adult patients with very high triglyceride levels. Unfortunately, Lovaza® can significantly increase LDL-C and/or non-HDL-C levels in some patients. A need exists for improved treatments for cardiovascular diseases and disorders.

SUMMARY

In various embodiments, the present invention provides methods of reducing the risk of a cardiovascular event in a subject on statin therapy. In one embodiment, the method comprises administering to the subject a pharmaceutical composition comprising about 1 g to about 4 g of eicosapentaenoic acid ethyl ester or a derivative thereof. In another embodiment, the subject has a fasting baseline triglyceride level of about 135 mg/dL to about 500 mg/dL. In another embodiment, the composition contains not more than 10%, by weight, docosahexaenoic acid or derivative thereof, substantially no docosahexaenoic acid or derivative thereof, or no docosahexaenoic acid or derivative thereof. In another embodiment, eicosapentaenoic acid ethyl ester comprises at least 96%, by weight, of all fatty acids present in the composition; the composition contains not more than 4%, by weight, of total fatty acids other than eicosapentaenoic acid ethyl ester; and/or the composition contains about 0.1% to about 0.6% of at least one fatty acid other than eicosapentaenoic acid ethyl ester and docosahexaenoic acid.

In another embodiment, the invention provides a method of treating hypertriglyceridemia comprising administering a composition as described herein to a subject in need thereof one to about four times per day.

These and other embodiments of the present invention will be disclosed in further detail herein below.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Compositions

In one embodiment, a composition of the invention is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, a composition for use in methods of the invention comprises eicosapentaenoic acid, or a pharmaceutically acceptable ester, derivative, conjugate or salt thereof, or mixtures of any of the foregoing, collectively referred to herein as "EPA." The term "pharmaceutically acceptable" in the present context means that the substance in question does not produce unacceptable toxicity to the subject or interaction with other components of the composition.

In another embodiment, the EPA comprises an eicosapentaenoic acid ester. In another embodiment, the EPA comprises a $C_1$-$C_5$ alkyl ester of eicosapentaenoic acid. In another embodiment, the EPA comprises eicosapentaenoic acid ethyl ester, eicosapentaenoic acid methyl ester, eicosapentaenoic acid propyl ester, or eicosapentaenoic acid butyl ester.

In another embodiment, the EPA is in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

In another embodiment, EPA is present in a composition useful in accordance with methods of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, or about 5000 mg.

In another embodiment, a composition useful in accordance with the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, docosahexaenoic acid (DHA), if any. In another embodiment, a composition of the invention contains substantially no docosahexaenoic acid. In still another embodiment, a composition useful in the present invention contains no docosahexaenoic acid and/or derivative thereof.

In another embodiment, EPA comprises at least 70%, at least 80%, at least 90%, at least 95%, at least 96%, at least 97%, at least 98%, at least 99%, or 100%, by weight, of all fatty acids present in a composition that is useful in methods of the present invention.

In some embodiments, the composition comprises at least 96% by weight of eicosapentaenoic acid ethyl ester and less than about 2% by weight of a preservative. In some embodiments, the preservative is a tocopherol such as all-racemic α-tocopherol.

In another embodiment, a composition useful in accordance with methods of the invention contains less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA. Illustrative examples of a "fatty acid other than EPA" include linolenic acid (LA), arachidonic acid (AA), docosahexaenoic acid (DHA), alpha-linolenic acid (ALA), stearadonic acid (STA), eicosatrienoic acid (ETA) and/or docosapentaenoic acid (DPA). In another embodiment, a composition useful in accordance with methods of the invention contains about 0.1% to about 4%, about 0.5% to about 3%, or about 1% to about 2%, by weight, of total fatty acids other than EPA and/or DHA.

In another embodiment, a composition useful in accordance with the invention has one or more of the following features: (a) eicosapentaenoic acid ethyl ester represents at least about 96%, at least about 97%, or at least about 98%, by weight, of all fatty acids present in the composition; (b) the composition contains not more than about 4%, not more than about 3%, or not more than about 2%, by weight, of total fatty acids other than eicosapentaenoic acid ethyl ester; (c) the composition contains not more than about 0.6%, not more than about 0.5%, or not more than about 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (e) the composition contains not more than about 20 ppm, not more than about 15 ppm or not more than about 10 ppm heavy metals, (0 the composition contains not more than about 5 ppm, not more than about 4 ppm, not more than about 3 ppm, or not more than about 2 ppm arsenic, and/or (g) the composition has a peroxide value of not more than about 5 meq/kg, not more than about 4 meq/kg, not more than about 3 meq/kg, or not more than about 2 meq/kg.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, compositions of the invention, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

Therapeutic Methods

In one embodiment, the invention provides a method for treatment and/or prevention of cardiovascular-related disease and disorders. The term "cardiovascular-related disease and disorders" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In various embodiments, the present invention provides methods of reducing a risk of a cardiovascular event in a subject on statin therapy. In some embodiments, the method comprises (a) identifying a subject on statin therapy and having a fasting baseline triglyceride level of about 135 mg/dL to about 500 mg/dL, wherein said subject has established cardiovascular disease or has a high risk of developing cardiovascular disease; and (b) administering to the subject a pharmaceutical composition comprising about 1 g to about 4 g of eicosapentaenoic acid ethyl ester per day, wherein the composition contains substantially no docosahexaenoic acid.

In some embodiments, the subject has a fasting baseline triglyceride level of about 135 mg/dL to about 500 mg/dL, for example 135 mg/dL to 500 mg/dL, 150 mg/dL to 500 mg/dL, or 200 mg/dL to <500 mg/dL. In some embodiments, the subject or subject group has a baseline triglyceride level (or median baseline triglyceride level in the case of a subject group), fed or fasting, of about 135 mg/dL, about 140 mg/dL, about 145 mg/dL, about 150 mg/dL, about 155 mg/dL, about 160 mg/dL, about 165 mg/dL, about 170 mg/dL, about 175 mg/dL, about 180 mg/dL, about 185 mg/dL, about 190 mg/dL, about 195 mg/dL, about 200 mg/dL, about 205 mg/dL, about 210 mg/dL, about 215 mg/dL, about 220 mg/dL, about 225 mg/dL, about 230 mg/dL, about 235 mg/dL, about 240 mg/dL, about 245 mg/dL, about 250 mg/dL, about 255 mg/dL, about 260 mg/dL, about 265 mg/dL, about 270 mg/dL, about 275 mg/dL, about 280 mg/dL, about 285 mg/dL, about 290 mg/dL, about 295 mg/dL, about 300 mg/dL, about 305 mg/dL, about 310 mg/dL, about 315 mg/dL, about 320 mg/dL, about 325 mg/dL, about 330 mg/dL, about 335 mg/dL, about 340 mg/dL, about 345 mg/dL, about 350 mg/dL, about 355 mg/dL, about 360 mg/dL, about 365 mg/dL, about 370 mg/dL, about 375 mg/dL, about 380 mg/dL, about 385 mg/dL, about 390 mg/dL, about 395 mg/dL, about 400 mg/dL, about 405 mg/dL, about 410 mg/dL, about 415 mg/dL, about 420 mg/dL, about 425 mg/dL, about 430 mg/dL, about 435 mg/dL, about 440 mg/dL, about 445 mg/dL, about 450 mg/dL, about 455 mg/dL, about 460 mg/dL, about 465 mg/dL, about 470 mg/dL, about 475 mg/dL, about 480 mg/dL, about 485 mg/dL, about 490 mg/dL, about 495 mg/dL, or about 500 mg/dL.

In some embodiments, the subject or subject group is also on stable therapy with a statin (with or without ezetimibe). In some embodiments, the subject or subject group also has established cardiovascular disease, or is at high risk for establishing cardiovascular disease. In some embodiments, the subject's statin therapy includes administration of one or more statins. For example and without limitation, the subject's statin therapy may include one or more of: atorvastatin, fluvastatin, lovastatin, pitavastatin, pravastatin, rosuvastatin, and simvastatin. In some embodiments, the subject is additionally administered one or more of: amlodipine, ezetimibe, niacin, and sitagliptin. In some embodiments, the subject's statin therapy includes administration of a statin and ezetimibe. In some embodiments, the subject's statin therapy includes administration of a statin without ezetimibe.

In some embodiments, the subject's statin therapy does not include administration of 200 mg or more per day of niacin and/or fibrates. In some embodiments, the subject is not on concomitant omega-3 fatty acid therapy (e.g., is not being administered or co-administered a prescription and/or over-the-counter composition comprising an omega-3 fatty acid active agent). In some embodiments, the subject is not administered or does not ingest a dietary supplement comprising an omega-3 fatty acid.

In some embodiments, the subject has established cardiovascular disease ("CV disease" or "CVD"). The status of a subject as having CV disease can be determined by any suitable method known to those skilled in the art. In some embodiments, a subject is identified as having established CV disease by the presence of any one of: documented coronary artery disease, documented cerebrovascular disease, documented carotid disease, documented peripheral arterial disease, or combinations thereof. In some embodiments, a subject is identified as having CV disease if the subject is at least 45 years old and: (a) has one or more stenosis of greater than 50% in two major epicardial coronary arteries; (b) has had a documented prior MI; (c) has been hospitalized for high-risk NSTE ACS with objective evidence of ischemia (e.g., ST-segment deviation and/or biomarker positivity); (d) has a documented prior ischemic stroke; (e) has symptomatic artery disease with at least 50% carotid arterial stenosis; (0 has asymptomatic carotid artery disease with at least 70% carotid arterial stenosis per angiography or duplex ultrasound; (g) has an ankle-brachial index ("ABI") of less than 0.9 with symptoms of intermittent claudication; and/or (h) has a history of aorto-iliac or peripheral arterial intervention (catheter-based or surgical).

In some embodiments, the subject or subject group being treated in accordance with methods of the invention has a high risk for developing CV disease. For example and without limitation, a subject or subject group has a high risk for developing CV disease if the subject or subject in a subject group is age 50 or older, has diabetes mellitus (Type 1 or Type 2), and at least one of: (a) is a male age 55 or older or a female age 65 or older; (b) is a cigarette smoker or was a cigarette smoker who stopped less than 3 months prior; (c) has hypertension (e.g., a blood pressure of 140 mmHg systolic or higher, or greater than 90 mmHg diastolic); (d) has an HDL-C level of ≤40 mg/dL for men or ≤50 mg/dL for women; (e) has an hs-CRP level of >3.0 mg/L; (0 has renal dysfunction (e.g., a creatinine clearance ("CrCL") of greater than 30 mL/min and less than 60 mL/min); (g) has retinopathy (e.g., defined as any of: non-proliferative retinopathy, preproliferative retinopathy, proliferative retinopathy, maculopathy, advanced diabetic eye disease, or history of photocoagulation); (h) has microalbuminuria (e.g., a positive micral or other strip test, an albumin/creatinine ratio of ≥2.5 mg/mmol, or an albumin excretion rate on timed collection of ≥20 mg/min all on at least two successive occasions); (i) has macroalbuminuria (e.g., albumix or other dip stick evidence of gross proteinuria, an albumin/creatinine ratio of ≥25 mg/mmol, or an albumin excretion rate on timed collection of ≥200 mg/min all on at least two successive occasions); and/or (j) has an ankle-brachial index of <0.9 without symptoms of intermittent claudication.

In some embodiments, the subject's baseline lipid profile is measured or determined prior to administering the pharmaceutical composition to the subject. Lipid profile characteristics can be determined by any suitable method known to those skilled in the art including, for example, by testing a fasting or non-fasting blood sample obtained from the subject using standard blood lipid profile assays. In some embodiments, the subject has one or more of: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 to about 30 mg/dL; and/or a baseline LDL-C value of about 40 to about 100 mg/dL.

In some embodiments, the cardiovascular event for which risk is reduced is one or more of: cardiovascular death; nonfatal myocardial infarction; nonfatal stroke; coronary revascularization; unstable angina (e.g., unstable angina determined to be caused by myocardial ischemia by, for example, invasive or non-invasive testing, and requiring hospitalization); cardiac arrest; peripheral cardiovascular disease requiring intervention, angioplasty, bypass surgery or aneurysm repair; death; and onset of new congestive heart failure.

In some embodiments, the subject is administered about 1 g to about 4 g of the pharmaceutical composition per day for about 4 months, about 1 year, about 2 years, about 3 years, about 4 years, about 5 years, or more than about 5 years. Thereafter, in some embodiments the subject exhibits one or more of (a) reduced triglyceride levels compared to baseline;
(b) reduced Apo B levels compared to baseline;
(c) increased HDL-C levels compared to baseline;
(d) no increase in LDL-C levels compared to baseline;
(e) a reduction in LDL-C levels compared to baseline;
(f) a reduction in non-HDL-C levels compared to baseline;
(g) a reduction in VLDL levels compared to baseline;
(h) a reduction in total cholesterol levels compared to baseline;
(i) a reduction in high sensitivity C-reactive protein (hs-CRP) levels compared to baseline; and/or
(j) a reduction in high sensitivity troponin (hsTnT) levels compared to baseline.

In some embodiments, the subject exhibits one or more of: (a) a reduction in triglyceride level of at least about 5%, at least about 10%, at least about 15%, at least about 20%, at least about 25%, at least about 30%, at least about 35%, at least about 40%, at least about 45%, at least about 50%, or at least about 55% as compared to baseline;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, or at least about 50% as compared to baseline;

(c) an increase in HDL-C levels of at least about 5%, at least about 10%, at least about 15%, at least about 20%, at least about 25%, at least about 30%, at least about 35%, at least about 40%, at least about 45%, or at least about 50% as compared to baseline; and/or (d) a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, or at least about 55% as compared to baseline.

In one embodiment, the subject or subject group being treated has a baseline EPA blood level on a (mol %) basis of less than 2.6, less than 2.5, less than 2.4, less than 2.3, less than 2.2, less than 2.1, less than 2, less than 1.9, less than 1.8, less than 1.7, less than 1.6, less than 1.5, less than 1.4, less than 1.3, less than 1.2, less than 1.1 or less than 1.

In another embodiment, the subject or subject group being treated has a baseline triglyceride level (or median baseline triglyceride level in the case of a subject group), fed or fasting, of about 135 mg/dL to about In some embodiments, the subject or subject group being treated in accordance with methods of the invention is on stable therapy with a statin (with or without ezetimibe). As used herein, the phrase "on stable therapy with a statin" means that the subject or subject group has been on the same daily dose of the same statin for at least 28 days and, if applicable, the same daily dose of ezetimibe for at least 28 days. In some embodiments, the subject or subject group on stable statin therapy has an LDL-C level of about 40 mg/dL to about 100 mg/dL.

In some embodiments, safety laboratory tests of subject blood samples include one or more of: hematology with complete blood count ("CBC"), including RBC, hemoglobin (Hgb), hematocrit (Hct), white cell blood count (WBC), white cell differential, and platelet count; and biochemistry panel including total protein, albumin, alkaline phosphatase, alanine aminotransferase (ALT/SGPT), aspartate aminotransferase (AST/SGOT), total bilirubin, glucose, calcium, electrolytes, (sodium, potassium, chloride), blood urea nitrogen (BUN), serum creatinine, uric acid, creatine kinase, and $HbA_{1c}$.

In some embodiments, a fasting lipid panel associated with a subject includes TG, TC, LDL-C, HDL-C, non-HDL-C, and VLDL-C. In some embodiments, LDL-C is calculated using the Friedewald equation, or is measured by preparative ultracentrifugation (Beta Quant) if the subject's triglyceride level is greater than 400 mg/dL. In some embodiments, LDL-C is measured by ultracentrifugation (Beta Quant) at randomization and again after about one year after randomization.

In some embodiments, a biomarker assay associated with blood obtained from a subject includes hs-CRP, Apo B and hsTnT.

In some embodiments, a medical history associated with a subject includes family history, details regarding all illnesses and allergies including, for example, date(s) of onset, current status of condition(s), and smoking and alcohol use.

In some embodiments, demographic information associated with a subject includes day, month and year of birth, race, and gender.

In some embodiments, vital signs associated with a subject include systolic and diastolic blood pressure, heart rate, respiratory rate, and body temperature (e.g., oral body temperature).

In some embodiments, a physical examination of a subject includes assessments of the subject's general appearance, skin, head, neck, heart, lung, abdomen, extremities, and neuromusculature.

In some embodiments, the subject's height and weight are measured. In some embodiments, the subject's weight is recorded with the subject wearing indoor clothing, with shoes removed, and with the subject's bladder empty.

In some embodiments, a waist measurement associated with the subject is measured. In some embodiments, the waist measurement is determined with a tape measure at the top of the subject's hip bone.

In some embodiments, an electrocardiogram associated with the subject is obtained. In some embodiments, an ECG is obtained every year during the treatment/follow-up portion of the study. In some embodiments, the ECG is a 12-lead ECG. In some embodiments, the ECG is analyzed for detection of silent MI.

In some embodiments, subjects randomly assigned to the treatment group receive 4 g per day of a composition comprising at least 96% by weight of eicosapentaenoic acid ethyl ester. In some embodiments, the composition is encapsulated in a gelatin capsule. In some embodiments, subjects in this treatment group continue to take 4 g per day of the composition for about 1 year, about 2 years, about 3 years, about 4 years, about 4.75 years, about 5 years, about 6 years, about 7 years, about 8 years, about 9 years, about 10 years, or more than about 10 years. In some embodiments, a median treatment duration is planned to be about 4 years.

In some embodiments, the present invention provides a method of reducing a risk of cardiovascular events in a subject. In some embodiments, the method comprises administering to the subject a composition comprising at least 96% by weight of eicosapentaenoic acid ethyl ester. In some embodiments, the subject is administered about 1 g to about 4 g of the composition per day.

In some embodiments, the reduced risk of CV events is indicated or determined by comparing an amount of time (e.g., an average amount of time) associated with a subject or subject group from first dosing to a first CV event selected from the group consisting of: CV death, nonfatal MI, nonfatal stroke, coronary revascularization, and hospitalization (e.g., emergent hospitalization) for unstable angina determined to be caused by myocardial ischemia (e.g., by invasive or non-invasive testing), to an amount of time (e.g., an average amount of time) associated with a placebo or untreated subject or group of subjects from first dosing with a placebo to a first CV event selected from the group consisting of: CV death, nonfatal MI, nonfatal stroke, coronary revascularization, and hospitalization (e.g., emergent hospitalization) for unstable angina determined to be caused by myocardial ischemia (e.g., by invasive or non-invasive testing), wherein said placebo does not include eicosapentaenoic acid ethyl ester. In some embodiments, the amount of time associated with the subject or group of subjects are compared to the amount of time associated with the placebo or untreated subject or group of subjects are compared using a log-rank test. In some embodiments, the log-rank test includes one or more stratification factors such as CV Risk Category, use of ezetimibe, and/or geographical region.

In some embodiments, the present invention provides a method of reducing risk of CV death in a subject on stable statin therapy and having CV disease or at high risk for developing CV disease, comprising administering to the subject a composition as disclosed herein.

In another embodiment, the present invention provides a method of reducing risk of recurrent nonfatal myocardial infarction (including silent MI) in a subject on stable statin therapy and having CV disease or at high risk for developing CV disease, comprising administering to the patient one or more compositions as disclosed herein.

In some embodiments, the present invention provides a method of reducing risk of nonfatal stroke in a subject on stable statin therapy and having CV disease or at high risk for developing CV disease, comprising administering to the subject a composition as disclosed herein.

In some embodiments, the present invention provides a method of reducing risk of coronary revascularization in a subject on stable statin therapy and having CV disease or at high risk for developing CV disease, comprising administering to the subject a composition as disclosed herein.

In some embodiments, the present invention provides a method of reducing risk of developing unstable angina caused by myocardial ischemia in a subject on stable statin therapy and having CV disease or at high risk for developing CV disease, comprising administering to the subject a composition as disclosed herein.

In another embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In some embodiments, the risk of a cardiovascular event in a subject is reduced compared to a control population. In some embodiments, a plurality of control subjects to a control population, wherein each control subject is on stable statin therapy, has a fasting baseline triglyceride level of about 135 mg/dL to about 500 mg/dL, and has established cardiovascular disease or a high risk of developing cardiovascular disease, and wherein the control subjects are not administered the pharmaceutical composition comprising about 1 g to about 4 g of eicosapentaenoic acid ethyl ester per day.

In some embodiments, a first time interval beginning at (a) an initial administration of a composition as disclosed herein to the subject to (b) a first cardiovascular event of the subject is greater than or substantially greater than a first control time interval beginning at (a') initial administration of a placebo to the control subjects to (b') a first cardiovascular event in the control subjects. In some embodiments, the first cardiovascular event of the subject is a major cardiovascular event selected from the group consisting of: cardiovascular death, nonfatal myocardial infarction, nonfatal stroke, coronary revascularization, and unstable angina caused by myocardial ischemia. In some embodiments, the first cardiovascular event of the control subjects is a major cardiovascular event selected from the group consisting of: cardiovascular death, nonfatal myocardial infarction, nonfatal stroke, coronary revascularization, and unstable angina caused by myocardial ischemia. In some embodiments, the first cardiovascular event of the subject and the first cardiovascular event of the control subjects is any of: death (from any cause), nonfatal myocardial infarction, or nonfatal stroke. In some embodiments, the first cardiovascular event of the subject and the first cardiovascular event of the control subjects is any of: death from a cardiovascular cause, nonfatal myocardial infarction, coronary revascularization, unstable angina, peripheral cardiovascular disease, or cardiac arrhythmia requiring hospitalization. In some embodiments, the first cardiovascular event of the subject and the first cardiovascular event of the control subjects is any of: death from a cardiovascular cause, nonfatal myocardial infarction, and coronary revascularization, unstable angina. In some embodiments, the first cardiovascular event of the subject and the first cardiovascular event of the control subjects is any of: death from a cardiovascular cause and nonfatal myocardial infarction. In some embodiments, the first cardiovascular event of the subject and the first cardiovascular event of the control subjects is death (from any cause). In some embodiments, the first cardiovascular event of the subject and the first cardiovascular event of the control subjects is any of: fatal myocardial infarction and nonfatal myocardial infarction (optionally including silent MI). In some embodiments, the first cardiovascular event of the subject and the first cardiovascular event of the control subjects is coronary revascularization. In some embodiments, the first cardiovascular event of the subject and the first cardiovascular event of the control subjects is hospitalization (e.g. emergent hospitalization) for unstable angina (optionally unstable angina caused by myocardial ischemia). In some embodiments, the first cardiovascular event of the subject and the first cardiovascular event of the control subjects is any one of: fatal stroke or nonfatal stroke. In some embodiments, the first cardiovascular event of the subject and the first cardiovascular event of the control subjects is any one of: new coronary heart failure, new coronary heart failure leading to hospitalization, transient ischemic attack, amputation for coronary vascular disease, and carotid revascularization. In some embodiments, the first cardiovascular event of the subject and the first cardiovascular event of the control subjects is any one of: elective coronary revascularization and emergent coronary revascularization. In some embodiments, the first cardiovascular event of the subject and the first cardiovascular event of the control subjects is an onset of diabetes. In some embodiments, the first cardiovascular event of the subject and the first cardiovascular event of the control subjects is cardiac arrhythmia requiring hospitalization. In some embodiments, the first cardiovascular event of the subject and the first cardiovascular event of the control subjects is cardiac arrest.

In some embodiments, a second time interval beginning at (a) an initial administration of the pharmaceutical composition to the subject to (c) a second cardiovascular event of the subject is greater than or substantially greater than a second control time interval beginning at (a') initial administration of a placebo to the control subjects to (c') a second cardiovascular event in the control subjects. In some embodiments, the second cardiovascular event of the subject and the second cardiovascular event of the control subjects is a major cardiovascular event selected from the group consisting of: cardiovascular death, nonfatal myocardial infarction, nonfatal stroke, coronary revascularization, and unstable angina caused by myocardial ischemia.

In some embodiments, the subject has diabetes mellitus and the control subjects each have diabetes mellitus. In some embodiments, the subject has metabolic syndrome and the control subjects each have metabolic syndrome.

In some embodiments, the subject exhibits one or more of (a) reduced triglyceride levels compared to the control population; (b) reduced Apo B levels compared to the control population; (c) increased HDL-C levels compared to the control population; (d) no increase in LDL-C levels compared to the control population; (e) a reduction in LDL-C levels compared to the control population; (f) a reduction in non-HDL-C levels compared to the control population; (g) a reduction in VLDL levels compared to the control population; (h) a reduction in total cholesterol levels compared to the control population; (i) a reduction in high sensitivity C-reactive protein (hs-CRP) levels compared to the control population; and/or (j) a reduction in high sensitivity troponin (hsTnT) levels compared to the control population.

In some embodiments, the subject's weight after administration of the composition is less than a baseline weight determined before administration of the composition. In some embodiments, the subject's waist circumference after administration of the composition is less than a baseline waist circumference determined before administration of the composition.

In methods of the present invention in which a time interval is determined or assessed, the time interval may be for example an average, a median, or a mean time interval. For example, in embodiments wherein a first control time interval is associated with a plurality of control subjects, the first control time interval is an average, a median, or a mean of a plurality of first control time intervals associated with each control subject. Similarly, in embodiments wherein a second control time interval is associated with a plurality of control subjects, the second control time interval is an average, a median, or a mean of a plurality of second control time intervals associated with each control subject.

In some embodiments, the reduced risk of cardiovascular events is expressed as a difference in incident rates between a study group and a control population. In some embodiments, the subjects in the study group experience a first major cardiovascular event after an initial administration of a composition as disclosed herein at a first incidence rate which is less than a second incidence rate, wherein the second incidence rate is associated with the rate of cardiovascular events in the subjects in the control population. In some embodiments, the first major cardiovascular event is any one of: cardiovascular death, nonfatal myocardial infarction, nonfatal stroke, coronary revascularization, and hospitalization for unstable angina (optionally determined to be caused by myocardial ischemia). In some embodiments, the first and second incidence rates are determined for a time period beginning on the date of the initial administration and ending about 4 months, about 1 year, about 2 years, about 3 years, about 4 years, or about 5 years after the date of initial administration.

In another embodiment, the invention provides use of any composition described herein for treating hypertriglyceridemia in a subject in need thereof, comprising: providing a subject having a fasting baseline triglyceride level of about 135 mg/dL to about 500 mg/dL and administering to the subject a pharmaceutical composition as described herein. In one embodiment, the composition comprises about 1 g to about 4 g of eicosapentaenoic acid ethyl ester, wherein the composition contains substantially no docosahexaenoic acid.

EXAMPLES

A phase 3, multi-center, placebo-controlled randomized, double-blind, 12-week study with an open-label extension is performed to evaluate the efficacy and safety of AMR101 in patients with fasting triglyceride levels ≥150 mg/dL and <500 mg/dL. The primary objective is, in patients at LDL-C goal while on statin therapy, with established cardiovascular disease (CVD) or at high risk for CVD, and hypertriglyceridemia (fasting triglycerides, TG, ≥200 mg/dL and <500 mg/dL, determine the efficacy of AMR101 4 g daily, compared to placebo, in preventing the occurrence of a first major cardiovascular event of the composite endpoint that includes:

cardiovascular ("CV") death;
nonfatal myocardial infarction ("MI");
nonfatal stroke;
coronary revascularization; and
unstable angina determined to be caused by myocardial ischemia by invasive/non-invasive testing and requiring emertgent hospitalization.

The secondary objectives of this study are the following:

To evaluate the effect of therapy on the composite of death from CV causes, nonfatal MI, coronary revascularization, unstable angina determined to be caused by myocardial ischemia by invasive/non-invasive testing and requiring emergent hospitalization, nonfatal stroke, or peripheral CV disease requiring intervention, angioplasty, bypass surgery, and aneurysm repair;

To evaluate the effect of therapy on combinations of each of the clinical events listed in secondary objective #1, supra, in addition to cardiac arrhythmia requiring hospitalization, cardiac arrest, peripheral CV disease requiring intervention, angioplasty, bypass surgery, aneurysm repair, and total mortality;

To evaluate the effect of therapy on the occurrence of a second, third, fourth and fifth major cardiovascular event (e.g., occurrence of CV death, nonfatal MI, nonfatal stroke, coronary revascularization, and unstable angina determined to be caused by myocardial ischemia by invasive/non-invasive testing and requiring emergent hospitalization after a first occurrence of any of same);

To evaluate the effect of therapy on the first occurrence of a major cardiovascular event in subgroups of patients including (a) those with diabetes mellitus, and (b) those with metabolic syndrome (e.g., as defined by the NCEP ATP III or future criteria as may evolve therefrom);

To evaluate the effect of therapy on new congestive heart failure ("CHF"), on new CHF as a primary cause of hospitalization, on transient ischemic attack, on amputation for CV disease, and on carotid revascularization;

To evaluate the effect of therapy on occurrence of elective coronary revascularization and emergent coronary revascularization;

To evaluate the effects of therapy on lipids, lipoproteins and inflammatory markers including triglycerides, total cholesterol, low-density lipoprotein cholesterol ("LDL-C"), high-density lipoprotein cholesterol ("HDL-C"), non-HDL-C, very low-density lipoprotein cholesterol ("VLDL-C"), apoliporpotein B ("apo B"), high-sensitivity C-reactive protein ("hs-CRP"), and high-sensitivity troponin ("hsTnT") as follows:

Evaluation of the effect of therapy on each marker;
Evaluation of the effect of the baseline value of each marker on therapy effects; and
Evaluation of the effect of therapy for preventing clinical events as defined above among all patients in the study and in sub-groups such as patients with diabetes mellitus and patients with substantial on-treatment changes of any of the markers;

To evaluate the effect of therapy on new onset diabetes; and

To explore the effect of therapy on weight and waist circumference.

Study Population

The population for this study is men and women ≥45 years of age with established CVD, or men and women ≥50 years of age with diabetes in combination with one additional risk factor for CVD. In addition, all patients will have atherogenic dyslipidemia defined as on treatment for hypercholesterolemia (but at treatment goal for LDL-C, by treatment with a statin) and hypertriglyceridemia. More details are listed in the inclusion criteria.

The patients will need to provide consent to participate in the study and be willing and able to comply with the protocol and the study procedures.

Study Periods

This study consists of the following study periods:

Screening Period: During the screening period, patients will be evaluated for inclusion/exclusion criteria.

At the first visit to the Research Unit (Visit 1), study procedures will be performed for evaluation of patient's eligibility in the study. At this screening visit, patients will sign an informed consent form before any study procedure is performed; the informed consent form will cover the treatment/follow-up period. Based on the evaluation from Visit 1, the following situations may occur:

Patients who are eligible for participation based on the study procedures on Visit 1 will return to the Research Unit for Visit 2 (randomization visit) to start the treatment/follow-up period. This case includes, for example, patients at Visit 1 who are on a stable dose of a statin, are planning to stay on the same statin and the same dose of the statin, and who not need to wash out any non-statin lipid-altering medications.

Patients who are not eligible for participation based on the study procedures on Visit 1 and are unlikely to become eligible in the next 28 days (for example: unlikely to stabilize statin dose, unable to wash out non-statin lipid-altering medications, etc.): these patients will be screen failed after Visit 1.

Patients not eligible for participation in the study based on the study procedures on Visit 1 may possibly become eligible in the next 28 days: these patients may return at the discretion of the investigator for a second optional screening visit (Visit 1.1) at which time the procedures needed for re-evaluation of the previously failed inclusion/exclusion criteria will be repeated. This case includes, for example, patients who are started on a statin at Visit 1, whose statin dose is changed at Visit 1, and/or needed to wash out non-statin lipid-altering medications. The following applies for these patients:

Patients with a change in the statin or statin dose on Visit 1 will need to be on a stable statin dose for at least 28 days before the lipid qualifying measurements at Visit 1.1. Other concomitant medications (antidiabetic therapy, for example) can be optimized or stabilized during this period.

Patients starting a washout at Visit 1 will have a washout period of at least 28 days (only 7 days for bile acid sequestrants) before the lipid qualifying measurements at Visit 1.1.

Patients at Visit 1 who are on a stable dose of a statin, are planning to stay on the same statin at the same dose, and who do not need any medication washout, but were asked to return for Visit 1.1 to repeat one or more of the other study procedures not related to concomitant medications Patients who become eligible for participation based on the additional study procedures at Visit 1.1 will return to the Research Unit for Visit 2 (randomization visit) to start the treatment/follow-up period.

At the end of the screening period, patients will need to meet all inclusion/exclusion criteria before they can be randomized. Patients who are not eligible for participation after the screening period (based on study procedures at Visit 1 and/or Visit 1.1) may return at a later date for rescreening. These patients will need to re-start with all procedures starting with Visit 1. This includes patients who need more time to stabilize one or more conditions or therapies (for example: statin, antidiabetic, antihypertensive, thyroid hormone, HIV-protease inhibitor therapy).

Treatment/Follow-Up Period: Within 42 days after the first screening visit (Visit 1) or within 60 days after the first screening visit (Visit 1) for those patients that have a second screening visit (Visit 1.1), eligible patients will enter the treatment/follow-up period. During this period, the patients will receive study drug during the planned visits at the Research Site and take the study drug while away from the Research Site.

During the visits, study procedures will be performed for evaluation of efficacy and safety. A detailed schedule of procedures is provided in Table 1.

Study Duration

The estimated study duration includes a planned 18-month enrollment period followed by a follow-up period of approximately 3.5 years in expected duration (approximately 5 years in total). Patients will be randomized at different times during the enrollment period but will all end the study at the same date (study end date). It is planned that all randomized patients will receive study medication and be followed-up until the study end date. This is an event-driven trial and patients will continue in the trial if the trial runs longer than expected, or will terminate earlier if the trial runs shorter than expected.

The total duration of the trial is based on a median 4-year follow-up period across patients. The first patient randomized would be followed for 4.75 years (the longest individual follow-up duration), and the last patient randomized would be followed for 3.25 year (the shortest individual follow-up duration).

Study Groups

At Visit 2 (Day 0), eligible study patients will be randomly assigned to the following treatment groups:

Group 1: AMR101 4 g daily (four 1000 mg capsules daily)

Group 2: placebo (four capsules daily)

The four AMR101 or placebo capsules daily will be taken as two capsules in the morning and two capsules in the evening (twice-per-day dosing regimen).

Number of Patients

This is an event-driven trial: It is expected that a minimum of 1612 primary efficacy endpoint events will be required during the study. A total of approximately 7990 patients will be entered into the study to either receive AMR101 or placebo (approximately 3995 patients per treatment group) in order to observe an estimated 1612 events that make up the primary composite endpoint for efficacy.

Number of Study Sites

Participants will be enrolled at multiple Research Sites in multiple countries.

Randomization

On Day 0, eligible patients will be randomized to one of 2 study groups using a computer-generated randomization schema. Randomized treatment assignment to either AMR101 or placebo in a 1:1 ratio will be provided using the internet (IWR).

Blinding

This is a double-blind study. Patients, investigators, pharmacists and other supporting staff at the Research Sites, personnel and designees of the Sponsor, study administrators and personnel at the organization(s) and vendors supporting the study will be unaware of the randomization code (i.e., they will not know which study participants are receiving the experimental drug and which are receiving the placebo drug). The study medication AMR101 and placebo capsules will be similar in size and appearance to maintain blinding.

During the double-blind treatment/follow-up period, everyone (patients, investigators, pharmacists and other supporting staff at the Research Sites, personnel and designees of the Sponsor, study administrators and personnel at the organization(s) and vendors managing/supporting the study), with the exception of the laboratory personnel performing the analysis, will be blinded to individual results of the efficacy laboratory measurements (including lipid values). Individual results from the lipid profile may be unblinded in the event of an emergency for a patient.

Stratification

Participants will be assigned to treatment groups stratified by CV risk category, use of ezetimibe and by geographical region (Westernized, Eastern European, and Asia Pacific countries). There are two CV risk categories:

CV Risk Category 1: patients with established CVD defined in the inclusion criteria. Patients with diabetes and established CVD are included in this category.

CV Risk Category 2: patients with diabetes and at least one additional risk factor for CVD, but no established CVD.

Stratification will be recorded in the IWR at the time of enrollment. Approximately 70% of randomized patients will be in the CV Risk Category 1 and approximately 30% of randomized patients will be in the CV Risk Category 2. Enrollment with patients of a CV risk category will be stopped when the planned number of patients in that risk category is reached.

Study Population

Inclusion Criteria

Patients meeting the following criteria will be eligible to participate in the study:

Fasting TG levels of ≥200 mg/dL (2.26 mmol/L) and <500 mg/dL (5.64 mmol/L).

LDL-C>40 mg/dL (1.04 mmol/L) and ≤100 mg/dL (2.60 mmol/L) and on stable therapy with a statin (with or without ezetimibe) for at least 4 weeks prior to the LDL-C/TG baseline qualifying measurements for randomization Stable therapy is defined as the same daily dose of the same statin for at least 28 days before the lipid qualification measurements (TG and LDL-C) and, if applicable, the same daily dose of ezetimibe for at least 28 days before the lipid qualification measurements (TG and LDL-C). Patients who have their statin therapy or use of ezetimibe initiated at Visit 1, or have their statin, statin dose and/or ezetimibe dose changed at Visit 1, will need to go through a stabilization period of at least 28 days since initiation/change and have their qualifying lipid measurements measured (TG and LDL-C) after the washout period (at Visit 1.1).

Statins may be administered with or without ezetimibe.

If patients qualify at the first qualification visit (Visit 1) for TG and LDL-C, and meet all other inclusion/exclusion criteria, they may be randomized at Visit 2. If patients don't qualify at the first qualifying visit (Visit 1), a second re-qualifying visit (Visit 1.1) is allowed. For some patients, because they need to stabilize medications and/or need to washout medications, the second re-qualifying visit (Visit 1.1) will be needed after the stabilization/washout period.

Either having established CVD (in CV Risk Category 1) or at high risk for CVD (in CV Risk Category 2). The CV risk categories are defined as follows:

CV Risk Category 1: defined as men and women ≥45 years of age with one or more of the following:

Documented coronary artery disease (CAD; one or more of the following primary criteria must be satisfied):

Documented multivessel CAD (>50% stenosis in at least two major epicardial coronary arteries—with or without antecedent revascularization)

Documented prior MI

Hospitalization for high-risk NSTE-ACS (with objective evidence of ischemia: ST-segment deviation or biomarker positivity)

Documented cerebrovascular or carotid disease (one of the following primary criteria must be satisfied):

Documented prior ischemic stroke

Symptomatic carotid artery disease with ≥50% carotid arterial stenosis

Asymptomatic carotid artery disease with ≥70% carotid arterial stenosis per angiography or duplex ultrasound History of carotid revascularization (catheter-based or surgical)

Documented peripheral arterial disease (PAD; one or more of the following primary criteria must be satisfied):

ABI<0.9 with symptoms of intermittent claudication

History of aorto-iliac or peripheral arterial intervention (catheter-based or surgical)

OR

CV Risk Category 2: defined as patients with:

Diabetes mellitus (Type 1 or Type 2) requiring treatment with medication AND

Men and women ≥50 years of age AND

One of the following at Visit 1 (additional risk factor for CVD):

Men ≥55 years of age or women ≥65 years of age;

Cigarette smoker or stopped smoking within 3 months before Visit 1;

Hypertension (blood pressure ≥140 mmHg systolic OR≥90 mmHg diastolic) or on antihypertensive medication;

HDL-C≤40 mg/dL for men or ≤50 mg/dL for women;

Hs-CRP>3.00 mg/L (0.3 mg/dL);

Renal dysfunction: CrCL>30 and <60 mL/min (>0.50 and <1.00 mL/sec);

Retinopathy, defined as any of the following: non-proliferative retinopathy, preproliferative retinopathy, proliferative retinopathy, maculopathy, advanced diabetic eye disease or a history of photocoagulation;

Micro- or macroalbuminuria. Microalbuminuria is defined as either a positive micral or other strip test (may be obtained from medical records), an albumin creatinine ratio ≥2.5 mg/mmol or an albumin excretion rate on timed collection ≥20 mg/min all on at least two successive occasions; macroalbuminuria, defined as albustix or other dipstick evidence of gross proteinuria, an albumin:creatinine ratio ≥25 mg/mmol or an albumin excretion rate on timed collection ≥200 mg/min all on at least two successive occasions;

ABI<0.9 without symptoms of intermittent claudication (patients with ABI<0.9 with symptoms of intermittent claudication are counted under CV Risk Category 1).

Patients with diabetes with CVD as defined above are eligible based on the CVD requirements and will be counted under CV Risk Category 1. Only patients with diabetes and no documented CVD as defined above need at least one additional risk factor as listed, and will be counted under CV Risk Category 2.

Women may be enrolled if all 3 of the following criteria are met:

They are not pregnant;

They are not breastfeeding;

They do not plan on becoming pregnant during the study.

Women of child-bearing potential must have a negative urine pregnancy test before randomization.

Women are not considered to be of childbearing potential if they meet one of the following criteria as documented by the investigator:

They have had a hysterectomy, tubal ligation or bilateral oophorectomy prior to signing the informed consent form;

They are post-menopausal, defined as ≥1 year since their last menstrual period or have a follicle-stimulating hormone (FSH) level in a menopausal range.

Women of childbearing potential must agree to use an acceptable method of avoiding pregnancy from screening to the end of the study, unless their sexual partner(s) is/are surgically sterile or the woman is abstinent.

Understanding of the study procedures, willing to adhere to the study schedules, and agreement to participate in the study by giving informed consent prior to screening.

Agree to follow a physician recommended diet and to maintain it through the duration of the study.

Exclusion Criteria

Patients are excluded from participation in the study if any of the following criteria apply:

Severe (class IV) heart failure.

Any life-threatening disease expected to result in death within the next 2 years (other than CVD).

Active severe liver disease (evaluated at Visit 1): cirrhosis, active hepatitis, ALT or AST>3×ULN, or biliary obstruction with hyperbilirubinemia (total bilirubin >2×ULN).

Hemoglobin A1c>10.0% (or 86 mmol/mol IFCC units) at screening (Visit 1). If patients fail this criterion (HbA1c>10.0% or 86 mmol/mol IFCC units) at Visit 1, they may have their antidiabetic therapy optimized and be retested at Visit 1.1.

Poorly controlled hypertension: blood pressure ≥200 systolic mmHg OR ≥100 mmHg diastolic (despite antihypertensive therapy).

Planned coronary intervention (such as stent placement or heart bypass) or any non-cardiac major surgical procedure. Patients can be (re)evaluated for participation in the trial (starting with Visit 1.1) after their recovery from the intervention/surgery.

Known familial lipoprotein lipase deficiency (Fredrickson Type I), apolipoprotein C-II deficiency, or familial dysbetalipoproteinemia (Fredrickson Type III)].

Participation in another clinical trial involving an investigational agent within 90 days prior to screening (Visit 1). Patients cannot participate in any other investigational medication or medical device trial while participating in this study (participation in a registry or observational study without an additional therapeutic intervention is allowed).

Intolerance or hypersensitivity to statin therapy.

Known hypersensitivity to any ingredients of the study product or placebo; known hypersensitivity to fish and or shellfish.

History of acute or chronic pancreatitis.

Malabsorption syndrome and/or chronic diarrhea (Note: patients who have undergone gastric/intestinal bypass surgery are considered to have malabsorption, hence are excluded; patients who have undergone gastric banding are allowed to enter the trial).

Non-study drug related, non-statin, lipid-altering medications, supplements or foods:

Patients are excluded if they used niacin >200 mg/day or fibrates during the screening period (after Visit 1) and/or plan to use during the study; patients who are taking niacin >200 mg/day or fibrates during the last 28 days before Visit 1 need to go through washout of at least 28 days after their last use and have their qualifying lipids measured (TG and LDL-C) after the washout period (Visit 1.1);

Patients are excluded if they take any omega-3 fatty acid medications (prescription medicines containing EPA and/or DHA) during the screening period (after Visit 1) and/or plan to use during the treatment/follow-up period of the study. To be eligible for participation in the study, patients who are taking omega-3 fatty acid medications during the last 28 days before Visit 1 (except patients in The Netherlands), need to go through a washout period of at least 28 days after their last use and have their qualifying lipids measured (TG and LDL-C) after the washout period (at Visit 1.1);

For patients in The Netherlands only: patients being treated with omega-3 fatty acid medications containing EPA and/or DHA are excluded; no washout is allowed.

Patients are excluded if they use dietary supplements containing omega-3 fatty acids (e.g., flaxseed, fish, krill, or algal oils) during the screening period (after Visit 1) and/or plan to use during the treatment/follow-up period of the study. To be eligible for participation in the study, patients who are taking >300 mg/day omega-3 fatty acids (combined amount of EPA and DHA) within 28 days before Visit 1 (except patients in The Netherlands), need to go through a washout period of at least 28 days since their last use and have their qualifying lipid measurements measured (TG and LDL-C) after the washout period (at Visit 1.1);

For patients in The Netherlands only: patients being treated with dietary supplements containing omega-3 fatty acids of ≥300 mg/day EPA and/or DHA are excluded; no washout is allowed.

Patients are excluded if they use bile acid sequestrants during the screening period (after Visit 1) and/or plan to use during the treatment/follow-up period of the study. To be eligible for participation in the study, patients who are taking bile acid sequestrants within 7 days before Visit 1, need to go through a washout period of at least 7 days since their last use and have their qualifying lipid measurements measured (TG and LDL-C) after the washout period (at Visit 1.1);

Other medications (not indicated for lipid alteration):

Treatment with tamoxifen, estrogens, progestins, thyroid hormone therapy, systemic corticosteroids (local, topical, inhalation, or nasal corticosteroids are allowed), HIV-protease inhibitors that have not been stable for >28 days prior to the qualifying lipid measurements (TG and LDL-C) during screening. To be eligible for participation in the study, patients who are not taking a stable dose of these medications within 28 days before Visit 1, need to go through a stabilization period of at least 28 days since their last dose change and have their qualifying lipid measurements measured (TG and LDL-C) after the washout period (at Visit 1.1).

Patients are excluded if they use cyclophosphamide or systemic retinoids during the screening period (after Visit 1) and/or plan to use during the treatment/follow-up period of the study. To be eligible for participation in the study, patients who are taking these medications within 28 days before Visit 1, need to go through a washout period of at least 28 days since their last use and have their qualifying lipid measurements measured (TG and LDL-C) after the washout period (at Visit 1.1).

Known to have AIDS (patients who are HIV positive without AIDS are allowed).

Requirement for peritoneal dialysis or hemodialysis for renal insufficiency or if creatinine clearance (CrCL)<30 mL/min (0.50 mL/sec).

Unexplained creatine kinase concentration >5×ULN or creatine kinase elevation due to known muscle disease (e.g., polymyositis, mitochondrial dysfunction) at Visit 1.

Any condition or therapy which, in the opinion of the investigator, might pose a risk to the patient or make participation in the study not in the patient's best interest.

Drug or alcohol abuse within the past 6 months, and unable/unwilling to abstain from drug abuse and excessive alcohol consumption during the study or drinking 5 units or more for men or 4 units or more for women in any one hour (episodic excessive drinking or binge drinking). Excessive alcohol consumption is on average >2 units of alcohol per day. A unit of alcohol is defined as a 12-ounce (350 mL) beer, 5-ounce (150 mL) wine, or 1.5-ounce (45 mL) of 80-proof alcohol for drinks.

Mental/psychological impairment or any other reason to expect patient difficulty in complying with the requirements of the study or understanding the goal and potential risks of participating in the study (evaluated at Visit 1).

Study Procedures
Assessment Schedule
  Screening Period
  Screening Visit (Visit 1)

Patients will come to the Research Site for Visit 1. They will be instructed to fast for at least 10 hours before their visit.

If patients qualify for randomization based on the procedures at Visit 1, they need to be randomized within 60 days after Visit 1. The following procedures will be performed at the screening visit:
  Obtain signed informed consent
  Assign the patient a patient number
  Obtain medical, surgical and family history
  Record demographics
  Obtain height, weight, and body mass index
  Obtain vital signs (systolic and diastolic blood pressure, heart rate, respiratory rate, and body temperature)
  Obtain a 12-lead electrocardiogram
  Evaluate inclusion/exclusion criteria
  This includes procedures and (fasting) blood samples (for example, hs-CRP, calculated creatinine clearance) as needed to determine the CV risk category (see inclusion criteria)
  Obtain fasting blood samples for chemistry and hematology testing
  Obtain a fasting blood sample for the lipid profile (TG, TC, HDL-C, LDL-C, non-HDL-C, VLDL-C)
  Perform a urine pregnancy test on women of childbearing potential
  Record concomitant medication(s)
  Instruct patient to fast for at least 10 hours prior to the next visit
  Screening Visit (Visit 1.1)

Some patients will skip Visit 1.1: Patients who qualify for study participation after Visit 1 because they meet all inclusion criterion and none of the exclusion criteria, may return to the Research Site for Visit 2 to be randomized and to start the treatment/follow-up period of the study. For these patients, Visit 2 will occur soon after Visit 1.

Patients, who do not qualify at Visit 1, may return to the Research Site for a second qualifying visit (Visit 1.1) at the discretion of the investigator. At Visit 1.1, procedures that caused failure of eligibility at Visit 1 will be repeated. Patients will be eligible for randomization after Visit 1.1 if they meet all inclusion criteria and if they no longer fail the exclusion criteria. If patients are evaluated at Visit 1.1 and qualify for randomization based on the repeated procedures at Visit 1.1, they need to be randomized within 60 days after Visit 1.

For some patients, Visit 1.1 will be mandatory at least 28 days after Visit 1 in order to check eligibility. These are patients who at Visit 1 started treatment with a statin, changed their statin, changed the daily dose of their statin, started to washout prohibited medications or started a stabilization period with certain medications (see inclusion/exclusion criteria for details). Any of these changes at Visit 1 may affect the qualifying lipid levels and therefore, patients will need to have Visit 1.1 to determine whether they qualify based on lipid level requirements (TG and LDL-C) determined at Visit 1. Other procedures that caused failure of eligibility at Visit 1 will also be repeated at Visit 1.1.

The following procedures will be performed at the screening visit:

Obtain vital signs (systolic and diastolic blood pressure, heart rate, respiratory rate, and body temperature)

Evaluate inclusion/exclusion criteria; only those evaluations will be repeated that deemed the patient not eligible on Visit 1.

Obtain fasting blood samples for chemistry and hematology testing. Only those samples will be obtained that deemed the patient not eligible on Visit 1.

Obtain a fasting blood sample for the lipid profile (TG, TC, HDL-C, LDL-C, non-HDL-C, VLDL-C) if the patient was deemed not eligible on Visit 1. This includes patients who at Visit 1 started treatment with a statin, changed their statin, changed the daily dose of their statin, started to washout prohibited medications or started a stabilization period with certain medications (see inclusion/exclusion criteria for details). These patients will have a fasting blood sample collected at Visit 1.1 for the qualifying lipid values (TG and LDL-C), and the TG and LDL-C inclusion criteria will be evaluated.

Record concomitant medication(s)

Treatment/Follow-Up Period

Every attempt should be made to complete the follow-up visits during the defined window periods.

Randomization visit (Visit 2; Day 0)

Qualified patients will return to the Research Site for Visit 2.

The following procedures will be performed at Visit 2:
Perform physical examination
Obtain weight
Obtain vital signs (systolic and diastolic blood pressure, heart rate, respiratory rate, and body temperature)
Measure waist circumference (one of the factors to diagnose metabolic syndrome)
Obtain a 12-lead electrocardiogram
Evaluate inclusion/exclusion criteria
Obtain fasting blood samples for:
Chemistry and hematology testing
Lipid profile (baseline)
Biomarker assays (baseline)
Genetic testing (optional blood sample)
Archiving (in countries and at sites approved by IRB/IEC and dependent on country regulations)

Perform a urine pregnancy test on women of childbearing potential (must be negative for randomization)
Dispense study drug and record randomization number
Instruct patient on how to take study drug
Administer study drug—Note: Study drug should be taken orally with food following the collection of all fasting blood samples
Assess for and record adverse events
Record concomitant medication(s)
Instruct patient:
To bring all study supplies with them to the next visit
Not to take study drug on the morning of their next visit
To fast for ≥10 hours prior to the next visit
Visit 3 (Day 120; ~4 Months)
Patients will return to the Research Site for Visit 3 on Day 120±10 days.
The following procedures will be performed:
Perform physical examination
Obtain weight
Obtain vital signs (systolic and diastolic blood pressure, heart rate, respiratory rate, and body temperature)
Obtain fasting blood samples for:
Chemistry and hematology testing
Lipid profile
Review study drug compliance by unused capsule count; discuss with and counsel patients about compliance if needed
Administer study drug—Note: Study drug should be taken orally with food following the collection of all fasting blood samples
Assess and record efficacy events
Assess for and record adverse events
Record concomitant medication(s)
Instruct patient:
To bring all study supplies with them to the next visit
Not to take study drug on the morning of their next visit
To fast for ≥10 hours prior to the next visit
Visits 4, 5, 6 and 7
At Visit 4: Day 360±10; Visit 5: Day 720±10; Visit 6: Day 1080±10; and Visit 7: Day 1440±10, the following procedures will be performed:
Perform physical examination
Obtain weight
Obtain vital signs (systolic and diastolic blood pressure, heart rate, respiratory rate, and body temperature)
Measure waist circumference (collected at Visit 5 only)
Obtain a 12-lead electrocardiogram
Obtain fasting blood samples for:
Chemistry and hematology testing
Lipid profile
Biomarker assays (collected at Visit 5 only)
Archiving (in countries and at sites approved by IRB/IEC and dependent on country regulations)
Review study drug compliance by unused capsule count; discuss with and counsel patients about compliance if needed
Administer study drug—Note: Study drug should be taken orally with food following the collection of all fasting blood samples
Assess and record efficacy events
Assess for and record adverse events
Record concomitant medication(s)
Instruct patient:
To bring all study supplies with them to the next visit
Not to take study drug on the morning of their next visit
To fast for ≥10 hours prior to the next visit Additional Visits The end date of the study is expected for Day 1800 but the actual end date will be dependent on the determination of the study end date by the DMC. The study end date is determined to be when approximately 1612 primary efficacy events have occurred. If the actual study end date is later than the expected end date, additional visits will be planned between Visit 7 and the Last Visit with a maximum of 360±10 days between visits. If the actual study end date is sooner than the expected end date, fewer visits will occur, and the last visit (See Section 6.1.2.5) will occur sooner.

On additional visits the same procedures will be performed as listed in Section 6.1.2.3. Irrespective of the number of additional visits, after the DMC has established the end of the study date, there will be a last visit with procedures as listed in Section 6.1.2.5.

Last Visit—End of Study

All patients will complete the study at the same time (within a 30-day window after the study end date), irrespective of the date that they were randomized. The end date of the study is planned for Day 1800 but the actual end date will be dependent on the determination of the study end date when approximately 1612 primary efficacy events have occurred (event-driven trial). For each patient, the last visit may occur within 30 day after the actual study end date. However, for the efficacy endpoints based on CV events, only events occurring up to and including the scheduled actual study end date will be included in the efficacy analyses.

A final follow-up visit is required for all patients. In the rare cases that a final follow-up visit cannot occur within the 30-day timeframe following the study end date, any attempt to contact the patient must be recorded on a special contact form, until/unless appropriate information is obtained.

At the Last Visit, the following procedures will be performed:

Perform physical examination
Obtain weight
Obtain vital signs (systolic and diastolic blood pressure, heart rate, respiratory rate, and body temperature)
Measure waist circumference
Obtain a 12-lead electrocardiogram
Obtain fasting blood samples for:
Chemistry and hematology testing
Lipid profile
Biomarker assays
Archiving (in countries and at sites approved by IRB/IEC and dependent on country regulations)
Determine study drug compliance by unused capsule count
Assess and record efficacy events
Assess for and record adverse events
Record concomitant medication(s)
Telephone Follow-up Contact Site personnel will contact each patient by telephone on the following study days:

Day 60±3 days
Day 180±5 days
Day 270±5 days
Day 450±5 days
Day 540±5 days
Day 630±5 days
Day 810±5 days
Day 900±5 days
Day 990±5 days
Day 1170±5 days
Day 1260±5 days
Day 1350±5 days
Day 1530±5 days
Day 1620±5 days
Day 1710±5 days If the treatment/follow-up period of the study is extended beyond the expected end date (Day 1800), additional follow-up phone calls will be made every 3 months in-between additional visits ±5 days. If the treatment/follow period of the study is shorter than the expected end date, less follow-up phone calls will be needed.

Every attempt will be made to talk to each patient within this time frame.

The following information will be collected from the patient:

Possible efficacy endpoints related to CV events. Patients will be asked to return to the Research Site to assess for any endpoints or events identified.
Adverse events
Concomitant medications
Current address and contact information (update if changed or will be changing)
Patients will be reminded about the following items:
To take the study medication according to the dosing schedule assigned, with food
When to return to the Research Center for the next visit
To bring the unused study medication to the next visit
To not take study drug on the morning of their next visit
To fast for at least 10 hours prior to the next visit Laboratory Procedures Clinical Laboratory Procedures All clinical laboratory determinations for screening and safety will be performed by a certified clinical laboratory under the supervision of the Sponsor or its designee.

Whenever possible and appropriate, samples for the clinical laboratory procedures will be collected after fasting for at least 10 hours. For the purposes of this study, fasting is defined as nothing by mouth except water (and any essential medications).

The investigator must review and sign all laboratory test reports. At screening, patients who have laboratory values that are outside the exclusionary limits specified in the exclusion criteria may not be enrolled in the study (patients can be considered for the study if values are classified as not clinically significant by the investigator). After randomization, the investigator will be notified if laboratory values are outside of their normal range. In this case, the investigator will be required to conduct clinically appropriate follow-up procedures.

Safety Laboratory Tests

The safety laboratory tests include:

Hematology with complete blood count (CBC), including RBC, hemoglobin (Hgb), hematocrit (Hct), white cell blood count (WBC), white cell differential, and platelet count Biochemistry panel including total protein, albumin, alkaline phosphatase, alanine aminotransferase (ALT/SGPT), aspartate aminotransferase (AST/SGOT), total bilirubin, glucose, calcium, electrolytes (sodium, potassium, chloride), blood urea nitrogen (BUN), serum creatinine, uric acid, creatine kinase, and HbA1c.

Fasting Lipid Profile

The fasting lipid panel includes: TG, TC, LDL-C, HDL-C, non-HDL-C, and VLDL-C.

At all visits, LDL-C will be calculated using the Friedewald equation. At Visit 1 and Visit 1.1 Direct LDL-C will be used if at the same visit TG>400 mg/dL (4.52 mmol/L). These LDL-C values will be used for the evaluation of the LDL-C inclusion criterion (LDL-C qualifying measurements for randomization) and for the assessment of changes in the statin therapy when LDL-C is not at goal. At all remaining visits (except Visit 2 and Visit 4) LDL-C will be measured by Direct LDL Cholesterol or by Preparative Ultracentrifugation if at the same visit TG>400 mg/dL (4.52 mmol/L). In addition, irrespective of the TG levels, at Visit 2 (0 Months of Follow-up, baseline) and at Visit 4 (12 Months of Follow-up), LDL-C will be measured by Preparative Ultracentrifugation. These Preparative Ultracentrifugation LDL-C measurements will be used in the statistical analysis including the calculation of the percent change from baseline (1 year versus baseline).

Genetic Testing

A fasting blood sample will be stored for future genetic testing at the discretion of the sponsor. The specifics of this test will be determined at a later date. This sample is optional as local regulations may prohibit genetic samples to be collected or shipped outside the country, or patients may not consent.

Research on genetic testing will look for links between genes and certain diseases, including their treatment(s) such as medicines and medical care. The blood samples will be collected in the study center with the regular protocol-required labs. Each patient tube with sample for genetic testing will be labeled with patient number only. The site will maintain a Subject Code Identification List for cross-reference. The patient number does not contain any identifiable information (i.e. Patient initials, date of birth, etc). Un-analyzed samples will be stored frozen by the sponsor for a period of up to 2 years following the end of the study, at which time they will be destroyed. If samples are tested, results will not be reported to the patient, parents, relatives, or attending physician and will not be recorded in the patient's medical records. There will be no follow-up contact with the sites or patients regarding this sample. The subject can withdraw their consent for genetic testing at any time up to analysis, even after the sample has been obtained. The subject can notify the site in writing that they withdraw their consent for the genetic testing portion of the study, and it will be documented by the site in the subject chart, as well as captured in the CRF. The lab will be notified to pull the sample and destroy it.

Biomarkers Assays

The biomarker assays include: hs-CRP, Apo B and hsTnT.

Additional laboratory tests

Additional laboratory tests include:

A urine pregnancy test will be administered to women of childbearing potential at certain visits as listed in schedule of procedures (Table 1). The urine pregnancy tests will be performed at the Research Site utilizing marketed test kits, or at a certified clinical laboratory.

A fasting blood sample (12 mL) for archiving. This sample will be collected only at sites in countries where allowed by local regulations and at sites for which approved by the IRB or IEC. The plasma from the archiving sample will be stored frozen in 2 separate equal aliquots, and will be used at the Sponsor's discretion to perform repeat analyses described in the protocol or to perform other tests related to cardiovascular health.

Blinding of Laboratory Results

All efficacy laboratory results during the double-blind period of the trial will be blinded (values not provided) to patients, investigators, pharmacists and other supporting staff at the Research Sites, personnel and designees of the Sponsor, study administrators and personnel at the organization(s) and vendors managing and/or supporting the study, with the exception of the laboratory personnel conducting the assays. To ensure patient safety, hsTnT values will be reported to the site.

Flagging of Critical Lab Values

Critical lab values are values that may warrant medical intervention to avoid possible harm to a patient. Critical lab values will be defined in the Laboratory Manual for the study, and the Research Site will be notified of the occurrence of a critical lab value (critical high or critical low) by a special annotation (flag) in the laboratory reports provided to the Research Sites. Although laboratory values that are part of the efficacy endpoints during the double-blind period of the study will not be provided to the Research Site (see Section 6.3.1.6), the sites will be notified when the TG value of a patient sample is >1000 mg/dL (11.29 mmol/L) (critical high TG value) or if the LDL-C values of a patient sample is >130 mg/dL (3.37 mmol/L) (critical high LDL-C value). These critical high values will need to be confirmed by a repeat measurement (new fasting blood sample) within 7 days. TG value of >2000 mg/dL (22.58 mmol/L) will also be flagged, so that appropriate medical action can be taken by the investigator as soon as possible.

If TG values are confirmed critically high, patients may be discontinued from study drug with the option to remain on study. The investigator should use the best clinical judgment for each patient which could include the use of approved TG-lowering medications after patients have been discontinued from study drug.

If LDL-C values are confirmed critically high, the investigator may need to take appropriate medical action which could include: reinforce/intensify therapeutic lifestyle changes (including diet and physical activity), increase the dose of the present statin therapy, add ezetimibe, or prescribe a more potent statin to lower LDL-C. The investigator should use the best clinical judgment for each patient.

Medical Procedures

Medical, Surgical and Family History

Medical history, including family history and details regarding all illnesses and allergies, date(s) of onset, status of current condition, and smoking and alcohol use will be collected on all patients.

Demographics

Demographic information including day, month, and year of birth, race, and gender will be collected for all patients.

Vital Signs

Vital signs include systolic and diastolic blood pressure, heart rate, respiratory rate, and body temperature. Blood pressure will be measured using a standardized process:

Patient should sit for ≥5 minutes with feet flat on the floor and measurement arm supported so that the midpoint of the manometer cuff is at heart level.

Use a mercury sphygmomanometer or automatic blood pressure device with an appropriately sized cuff with the bladder centered over the brachial artery.

Blood pressure should be recorded to the nearest 2 mmHg mark on the manometer or to the nearest whole number on an automatic device. A blood pressure reading should be repeated 1 to 2 minutes later, and the second reading should also be recorded to the nearest 2 mmHg mark.

Physical Examination

A physical examination must include source documentation of general appearance, skin, and specific head and neck, heart, lung, abdomen, extremities, and neuromuscular assessments.

Height, Weight and Body Mass Index

Height and weight will be measured. Measurement of weight should be performed with the patient dressed in indoor clothing, with shoes removed, and bladder empty.

Waist Circumference

Waist circumference will be measured with a tape measure, as follows: Start at the top of the hip bone then bring the tape measure all the way around—level with the navel. Make sure the tape measure is snug, but without compressing the skin, and that it is parallel with the floor.

Patients should not hold their breath while measuring waist circumference.

Electrocardiogram (ECG)

ECGs (standard 12-lead) will be obtained annually. Site personnel should make every attempt to perform a patient's ECG using the same equipment at each visit. ECGs will be reviewed by the site for the detection of silent MI. Silent MIs will be sent for event adjudication.

Treatment and Restrictions

Treatment

Treatment Regimen, Dosage, and Duration

Eligible study patients will be randomly assigned on Day 0 to one of the 2 treatment groups. Patients in each group will receive either 4 g/day AMR101 or placebo for up to 4.75 years (4 years planned median treatment duration) according to Table 2.

The daily dose of study drug is 4 capsules per day taken as two capsules take on two occasions per day (2 capsules given twice daily).

TABLE 2

Dosing Schedule during the Treatment Period

| Treatment Group | Daily Dose | Number of Capsules per Day |
| --- | --- | --- |
| 1 | 4 g | 4 capsules of 1000 mg AMR101 |
| 2 | Placebo | 4 capsules of matching placebo |

Patients will be instructed to take study drug with food (i.e., with or at the end of their morning and evening meals). On days that patients are scheduled for study visits, the daily dose of study drug will be administered by site personnel with food provided by the site following collection of all fasting blood samples. For the purposes of this study, fasting is defined as nothing by mouth except water (and any essential medications) for at least 10 hours.

Treatment Assignment

Identification Number

A unique patient identification number (patient number) will be established for each patient at each site. The patient number will be used to identify the patient throughout the study and will be entered on all documentation. If a patient is not eligible to receive treatment, or if a patient discontinues from the study, the patient number cannot be reassigned to another patient. The patient number will be used to assign patients to one of the 2 treatment groups according to the randomization schedule.

Drug Randomization

Only qualified patients who meet all of the inclusion criteria and none of the exclusion criteria will be randomized and will receive study medication starting at Visit 2 (Day 0). Eligible patients will be randomly assigned to one of the 2 treatment groups. Randomization will be stratified by CV risk category, use of ezetimibe and by geographical region (Westernized, Eastern European, and Asia Pacific countries) (See Section 3.10). Approximately 70% of randomized patients will be in the CV Risk Category 1, including patients with established CVD, and approximately 30% of randomized patients will be in the CV Risk Category 2, including patients with diabetes and at least one additional risk factor but no established CVD. Enrollment with patients of a CV risk category will be stopped when the planned number of patients in that risk category is reached.

Emergency Unblinding

In an emergency, when knowledge of the patient's treatment assignment is essential for the clinical management or welfare of the patient, the investigator may request the patient's treatment assignment for unblinding. Prior to unblinding the patient's individual treatment assignment, the investigator should assess the relationship of an adverse event to the administration of the study drug (Yes or No). If the blind is broken for any reason, the investigator must record the date and reason for breaking the blind on the appropriate Case Report Form (CRF) and source documents.

Compliance Control

It is recommended that, unless clear contraindications arise, patients be strongly encouraged to adhere to their treatment regimen with the study drug for the duration of the trial. Any interruptions of therapy should, if possible, be brief (e.g., <4 weeks) and only for clinically indicated reasons, such as adverse events. Discontinuations will be discouraged as much as possible. Any discontinuations should be based on compelling clinical reasons.

For every patient, an assessment of compliance to the study drug treatment regimen must be obtained at each scheduled visit. Study medication will be dispensed in amounts exceeding the amount required for the study. Patients will be instructed to return all unused study medication at the next visit. Compliance to the study drug regimen will be evaluated at each visit by counting unused capsules. Discrepancies will be evaluated and discussed with each patient to assess compliance. If compliance is unsatisfactory, the patient will be counseled about the importance of compliance to the dosing regimen. At the end of the study, the final study medication compliance will be determined by unused capsule count.

Study Restrictions

Concomitant Medications During Treatment/Follow-Up Period

Any medications administered during the study period must be documented on the Concomitant Medication CRF. Patients must not have taken any investigational agent within 90 days prior to screening. Patients cannot participate in any other investigational medication trial while participating in this study.

The following non-study drug related, non-statin, lipid-altering medications and supplements, and foods are prohibited during the study (from Visit 1 until after the Last Visit-End of Study), except for compelling medical reasons in ODIS patients:

niacin >200 mg/day;
fibrates;
prescription omega-3 fatty acid medications;
dietary supplements containing omega-3 fatty acids (e.g., flaxseed, fish, krill, or algal oils);
bile acid sequestrants;
cyclophosphamide;
systemic retinoids If any of these products would be used during the treatment/follow-up period of the study, it should be for compelling medical reasons in ODIS patients, and it should be documented in the Concomitant Medication CRF. If the ODIS patient agrees to restart study medication, the use of excluded medication must be discontinued.

Foods enriched with omega-3 fatty acids are strongly discouraged after Visit 1 for the duration of the study (does not apply to The Netherlands or Canada only. Therefore, all centers in The Netherlands and Canada must ignore this request).

The following products are allowed: statins, ezetimibe, and herbal products & dietary supplements not containing omega-3 fatty acids.

Statins:

The same statin at the same dose should be continued until the end of the study, unless deemed medically necessary to change because of an adverse event or lack of efficacy (LOE). It is preferred that if LOE is the determining factor that ezetimibe be added to the present dose.

Switching between a brand name statin and the generic version of the same statin is allowed at any time during the study.

Statins may be administered with or without ezetimibe.

Based on the FDA recommendation, simvastatin 80 mg be used only in patients who have been taking this dose for 12 months or more and have not experienced any muscle toxicity. (See reference: FDA Drug Safety Communication: Ongoing safety review of high-dose Zocor (simvastatin) and increased risk of muscle injury.
(http://www.fda.gov/Drugs/DrugSafety/PostmarketDrug-SafetyInformationforPatientsandProviders/ucm204882.htm)

Changing of the type of statin or the statin dose during the treatment/follow-up period of the study should only be done for compelling medical reasons and must be documented in the CRF.

LDL-C Rescue:

If the level of LDL-C exceeds 130 mg/dL (3.37 mmol/L) during the study (initial measurement and confirmed by a second determination at least 1 week later), the investigator may either increase the dose of the present statin therapy or may add ezetimibe to lower LDL-C. The investigator should use the best clinical judgment for each patient.

No data are available with regard to potential interactions between ethyl-EPA and oral contraceptives. There are no reports suggesting that omega-3 fatty acids, including ethyl-EPA, would decrease the efficacy of oral contraceptives.

Patient Restrictions

Beginning at the screening visit, all patients should be instructed to refrain from excessive alcohol consumption, to follow a physician recommended diet and to maintain it through the duration of the study. Excessive alcohol consumption is on average 2 units of alcohol per day or drinking 5 units or more for men or 4 units or more for women in any one hour (episodic excessive drinking or binge drinking). A unit of alcohol is defined as a 12-ounce (350 mL) beer, 5-ounce (150 mL) wine, or 1.5-ounce (45 mL) of 80-proof alcohol for drinks.

Investigational Product

Clinical Trial Material

The following will be supplied by the Sponsor:

AMR101 1000 mg capsules

Placebo capsules

The Sponsor will supply sufficient quantities of AMR101 1000 mg capsules and placebo capsules to allow for completion of the study. The lot numbers of the drugs supplied will be recorded in the final study report.

Records will be maintained indicating the receipt and dispensation of all drug supplies. At the conclusion of the study, any unused study drug will be destroyed.

Pharmaceutical Formulations

AMR101 1000 mg and placebo capsules (paraffin) are provided in liquid-filled, oblong, gelatin capsules. Each capsule is filled with a clear liquid (colorless to pale yellow in color). The capsules are approximately 25.5 mm in length with a diameter of approximately 9.5 mm.

Labeling and Packaging

Study medication will be packaged in high-density polyethylene bottles. Labeling and packaging will be performed according to GMP guidelines and all applicable country-specific requirements. The bottles will be numbered for each patient based on the randomization schedule. The patient randomization number assigned by IWR or a designee of the Sponsor for the study (if no IWR system is used), will correspond to the number on the bottles. The bottle number for each patient will be recorded in the Electronic Data Capture (EDC) system for the study.

Dispensing Procedures and Storage Conditions

Dispensing Procedures

At Visit 2 (Day 0), patients will be assigned study drug according to their treatment group determined by the randomization schedule. Once assigned to a treatment group, patients will receive study drug supplies. At each visit, patients will bring unused drug supplies dispensed to them earlier. From the drug supplies assigned to each patient, site personnel will administer drug while the patients are at the Research Site.

The investigator or designee must contact the IWR system or a designee of the Sponsor for the study (if no IWR system is used) when any unscheduled replacements of study medication are needed.

During the last visit during the treatment period, patients will bring the unused drug supplies for site personnel to calculate the final study medication compliance by unused capsule count.

Storage Conditions

At the Research Sites, study drugs must be stored at room temperature, 68° F. to 77° F. (20° C. to 25° C.). Do not allow storage temperature to go below 59° F. (15° C.) or above 86° F. (30° C.). Store in the original package.

Study drugs must be stored in a pharmacy or locked and secure storage facility, accessible only to those individuals authorized by the investigator to dispense the drug. The investigator or designee will keep accurate dispensing records. At the conclusion of the study, study site personnel will account for all used and unused study drug. Any unused study drug will be destroyed. The investigator agrees not to distribute study drug to any patient, except those patients participating in the study.

Efficacy Assessments

Specification of Variables and Procedures

The primary endpoint and the majority of the secondary and tertiary endpoints are based on clinical events related to CVD and mortality. All events occurring between randomization and the study end date (inclusive) must be recorded. Only adjudicated events will be included in the final analyses. Further details on the assessment of clinical events and their definitions will be found in the CEC charter.

Efficacy Endpoints

Primary Efficacy Endpoint

Time from randomization to the first occurrence of the composite of the following clinical events:

CV death,

Nonfatal MI (including silent MI; ECGs will be performed annually for the detection of silent MIs), Nonfatal stroke, Coronary revascularization Hospitalization for unstable angina determined to be caused by myocardial ischemia by invasive/non-invasive testing.

The first occurrence of any of these major adverse vascular events during the follow-up period of the study will be included in the incidence.

Secondary Efficacy Endpoints

The key secondary efficacy endpoint is:

The composite of death from CV causes, nonfatal MI, coronary revascularization, unstable angina determined to be caused by myocardial ischemia by invasive/non-invasive testing and requiring emergent hospitalization, nonfatal stroke, or peripheral CVD requiring intervention, angioplasty, bypass surgery, or aneurysm repair.

Other secondary efficacy endpoints are as follows (to be tested in said order):

The composite of total mortality, nonfatal MI, or nonfatal stroke;

The composite of death from CV causes, nonfatal MI, coronary revascularization, unstable angina determined to be caused by myocardial ischemia by invasive/non-invasive testing and requiring emergent hospitalization, peripheral CVD requiring intervention, or cardiac arrhythmia requiring hospitalization;

The composite of death from CV causes, nonfatal MI, coronary revascularization, or unstable angina determined to be caused by myocardial ischemia by invasive/non-invasive testing and requiring emergent hospitalization;

The composite of death from CV causes or nonfatal MI;

Total mortality;

Fatal and nonfatal MI (including silent MI);

Coronary Revascularization;

Hospitalization for unstable angina determined to be caused by myocardial ischemia by invasive/non-invasive testing;

Fatal and nonfatal stroke.

For the secondary endpoints that count a single event, the first occurrence of this type of event will be counted in each patient. For secondary endpoints that are composites of two or more types of events, the first occurrence of any of the event types included in the composite will be counted in each patient.

Tertiary Efficacy Endpoints:

The second, third, fourth, and fifth major CV event of the primary composite endpoint. The type of (nonfatal) events may occur in any order.

Primary endpoint in subset of patients with diabetes mellitus;

Primary endpoint in subset of patients with metabolic syndrome;

New CHF, new CHF leading to hospitalization, transient ischemic attack, amputation for CVD and carotid revascularization;

Elective coronary revascularization and emergent coronary revascularization;

New onset diabetes;

Fasting TG, TC, LDL-C, HDL-C, non-HDL-C, VLDL-C, apo B, hs-CRP, and hsTnT: effect of baseline and on-treatment change of biomarkers on primary and key secondary endpoints;

CV mortality;

Cardiac Arrhythmias requiring hospitalization;

Cardiac Arrest;

To explore the effect of AMR101 on weight and waist circumference.

For the tertiary endpoints that count a single event, the first occurrence of this type of event will be counted in each patient. For tertiary endpoints that are composites of two or more types of events, the first occurrence of any of the event types included in the composite will be counted in each patient (except when stated otherwise, for the second, third, fourth, and fifth major CV event).

Safety Assessments

Specification of Variables and Procedures

Safety assessments will include adverse events, clinical laboratory measurements (chemistry, hematology), 12-lead ECGs, vital signs (systolic and diastolic blood pressure, heart rate, respiratory rate, and body temperature), and physical examinations as per Study Procedures/Table 1.

A complete medical, surgical and family history will be completed at Visit 1.

All laboratory test results must be evaluated by the investigator as to their clinical significance. Any observations at physical examinations or laboratory values considered by the investigator to be clinically significant should be considered an adverse event.

Adverse Events

An adverse event is defined as any untoward medical occurrence, which does not necessarily have a causal relationship with the medication under investigation. An adverse event can therefore be any unfavorable and/or unintended sign (including an abnormal laboratory finding), symptom, or disease temporally associated with the use of an investigational medication product, whether or not related to the investigational medication product. All adverse events, including observed or volunteered problems, complaints, or symptoms, are to be recorded on the appropriate CRF. Each adverse event is to be evaluated for duration, intensity, and causal relationship with the study medication or other factors.

Adverse events, which include clinical laboratory test variables, will be monitored from the time of informed consent until study participation is complete. Patients should be instructed to report any adverse event that they experience to the investigator. Beginning with Visit 2, investigators should assess for adverse events at each visit and record the event on the appropriate adverse event CRF.

Wherever possible, a specific disease or syndrome rather than individual associated signs and symptoms should be identified by the investigator and recorded on the CRF. However, if an observed or reported sign or symptom is not considered a component of a specific disease or syndrome by the investigator, it should be recorded as a separate adverse event on the CRF.

Any medical condition that is present when a patient is screened or present at baseline that does not deteriorate should not be reported as an adverse event. However, medical conditions or signs or symptoms present at baseline and that change in severity or seriousness at any time during the study should be reported as an adverse event.

Clinically significant abnormal laboratory findings or other abnormal assessments that are detected during the study or are present at baseline and significantly worsen will be reported as adverse events or SAEs. The investigator will exercise his or her medical and scientific judgment in deciding whether an abnormal laboratory finding or other abnormal assessment is clinically significant.

The investigator will rate the severity (intensity) of each adverse event as mild, moderate, or severe, and will also categorize each adverse event as to its potential relationship to study drug using the categories of Yes or No.

Severity:

Mild—An event that is usually transient in nature and generally not interfering with normal activities.

Moderate—An event that is sufficiently discomforting to interfere with normal activities.

Severe—An event that is incapacitating with inability to work or do usual activity or inability to work or perform normal daily activity.

Causality Assessment:

The relationship of an adverse event to the administration of the study drug is to be assessed according to the following definitions:

No (unrelated, not related, no relation)—The time course between the administration of study drug and the occurrence or worsening of the adverse event rules out a causal relationship and another cause (concomitant drugs, therapies, complications, etc.) is suspected.

Yes—The time course between the administration of study drug and the occurrence or worsening of the adverse event is consistent with a causal relationship and no other cause (concomitant drugs, therapies, complications, etc.) can be identified.

The following factors should also be considered:

The Temporal Sequence from Study Medication Administration

The event should occur after the study medication is given. The length of time from study medication exposure to event should be evaluated in the clinical context of the event.

Underlying, Concomitant, Intercurrent Diseases

Each report should be evaluated in the context of the natural history and course of the disease being treated and any other disease the patient may have.

Concomitant Medication

The other medications the patient is taking or the treatment the patient receives should be examined to determine whether any of them might be recognized to cause the event in question.

Known Response Pattern for this Class of Study Medication

Clinical and/or preclinical data may indicate whether a particular response is likely to be a class effect.

Exposure to Physical and/or Mental Stresses

The exposure to stress might induce adverse changes in the patient and provide a logical and better explanation for the event.

The Pharmacology and Pharmacokinetics of the Study Medication

The known pharmacologic properties (absorption, distribution, metabolism, and excretion) of the study medication should be considered.

Unexpected Adverse Events—An unexpected adverse event is an adverse event either not previously reported or where the nature, seriousness, severity, or outcome is not consistent with the current Investigator's Brochure.

Serious Adverse Events

A serious adverse event (SAE) is defined as an adverse event that meets any of the following criteria:

Results in Death

Is life-threatening-Note: The term "life-threatening" in the definition of "serious" refers to an event in which the patient was at risk of death at the time of the event. It does not refer to an event, which hypothetically might have caused death, if it were more severe.

Requires hospitalization or prolongation of existing hospitalization-Note: In general, hospitalization for treatment of a pre-existing condition(s) that did not worsen from baseline is not considered adverse events and should not be reported as SAEs.

Results in Disability/Incapacity

Is a congenital anomaly/birth defect;

Is an important medical event-Note: Important medical events that may not result in death, be life threatening, or require hospitalization may be considered an SAE when, based upon appropriate medical judgment, they may jeopardize the patient and may require medical or surgical intervention to prevent one of the outcomes listed above. Examples of such medical events include allergic bronchospasm requiring intensive treatment in an emergency room or at home, blood dyscrasias or convulsions that do not result in inpatient hospitalizations, or the development of drug dependency.

By design of this study SAEs that are endpoint events will only be recorded for the endpoint determination and not captured as SAEs. The intention is that the endpoint events are not reported to IRBs as SAEs, unless the IRB requires that these are reported. Investigators should specifically inform their institution/IRB of this plan and confirm whether or not they want the endpoint events reported. By agreement with the US FDA, these endpoints will also not be reported to the US FDA as SAEs; rather they will be reported as endpoint events. Following adjudication if the event is determined to not meet the criteria for an event, the event will be evaluated as an SAE beginning with that day as Day 0.

Serious Adverse Event Reporting—Procedure for Investigators

Initial Reports

All SAEs occurring from the time of informed consent until 28 days following the last administration of study medication must be reported to the Sponsor or designee within 24 hours of the knowledge of the occurrence (this refers to any adverse event that meets any of the aforementioned serious criteria). SAEs that the investigator considers related to study medication occurring after the 28-day follow-up period will also be reported to the Sponsor or designee.

The investigator is required to submit SAE reports to the Institutional Review Board (IRB) or Independent Ethics Committee (IEC) in accordance with local requirements. All investigators involved in studies using the same investigational medicinal product (IMP) will receive any Suspected Unexpected Serious Adverse Reaction (SUSAR) reports for onward submission to their local IRB as required. All reports sent to investigators will be blinded.

In addition, regulatory agencies will be notified of SAEs per the requirements of the specific regulatory jurisdiction regulations and laws.

Follow-Up Reports

The investigator must continue to follow the patient until the SAE has subsided, or until the condition becomes chronic in nature, stabilizes (in the case of persistent impairment), or the patient dies. Within 24 hours of receipt of follow-up information, the investigator must update the SAE form electronically in the EDC system for the study and submit any supporting documentation (e.g., laboratory test reports, patient discharge summary, or autopsy reports) to the Sponsor or designee via fax or email.

Reporting by the Sponsor

IRBs and IECs will be informed of SUSARs according to local requirements. Cases will be unblinded for reporting purposes as required.

Exposure in Utero During Clinical Trials

If a patient becomes pregnant during the study, the investigator should report the pregnancy to the Sponsor or designee within 24 hours of being notified. The Sponsor or designee will then forward the Exposure In Utero form to the investigator for completion.

The patient should be followed by the investigator until completion of the pregnancy. If the pregnancy ends for any reason before the anticipated date, the investigator should notify the Sponsor or designee. At the completion of the pregnancy, the investigator will document the outcome of the pregnancy. If the outcome of the pregnancy meets the criteria for immediate classification as an SAE (i.e., postpartum complication, spontaneous abortion, stillbirth, neonatal death, or congenital anomaly), the investigator should follow the procedures for reporting an SAE.

Treatment Discontinuation/Patient Withdrawal

Patients may withdraw from the study at any time and for any reason. Study drug administration may also be discontinued at any time, at the discretion of the investigator. In any case, follow-up for efficacy and safety should be continued.

Reasons for Early Study Drug Discontinuation

Study drug discontinuation should be avoided as much as possible, but may be done for any of the following reasons:

Patient withdraws consent or requests early discontinuation from the study for any reason. Patients should be encouraged to continue to participate in the study for the entire duration of the study even if they choose not to take study medication any longer.

Occurrence of a clinical or laboratory adverse event, either serious or non-serious, at the discretion of the investigator. The Sponsor or designee should be notified if a patient is discontinued because of an adverse event or laboratory abnormality. It is recommended that, unless clear contraindications arise, patients be strongly encouraged to adhere to their treatment regimen with the study drug for the duration of the trial. Any interruptions of therapy should, if possible, be brief (e.g., <4 weeks) and only for clinically indicated reasons, such as adverse events. The following should be considered reason for discontinuation:

ALT>3×ULN and bilirubin >1.5×ULN
ALT>5×ULN
ALT>3×ULN and appearance or worsening of hepatitis
ALT>3×ULN persisting for >4 weeks
ALT>3×ULN and cannot be monitored weekly for 4 weeks Any medical condition or personal circumstance that, in the opinion of the investigator, exposes the patient to risk by continuing in the study or precludes adherence to the protocol.

Sponsor discontinues the study.

A TG value that is flagged as critically high, i.e., >1000 mg/dL (11.29 mmol/L), and confirmed as critically high by a repeat measurement (new fasting blood sample) within 7 days. In this case, a patient may be discontinued from study drug (with the option to remain ODIS) and other lipid-altering medications may be (re)initiated. If the TG value is flagged as >2000 mg/dL (22.58 mmol/L) then appropriate medical action can be taken by the investigator as soon as possible.

Occurrence of an outcome event according to the judgment of the investigator is not considered a valid reason for study drug discontinuation.

Patients whose treatment with study medication is discontinued early, and have not withdrawn consent, will stay in study and will be monitored until the end of the study.

Patients that continue in the study after indefinite cessation of therapy will be characterized as Off Drug In Study (ODIS). ODIS patients should be asked to return to the study site for an interim visit once the patient has been off study drug for >30 days. Procedures at this visit are consistent with those at Visit 5. If not contraindicated, patients will also have the option to restart study medication at any point once characterized as ODIS.

The reason for study drug discontinuation or interruption will be recorded on the CRF.

Follow-Up after Early Study Drug Discontinuation/Lost to Follow-Up

Patients who prematurely discontinue study drug are not to be replaced.

All randomized patients must be followed up according to the study flowchart until the study end date or death, regardless of whether they discontinue study drug prematurely or not. Any event occurring after early study drug discontinuation will be recorded up through the study end date.

In order to follow the medical status of the patients, especially when they discontinued the study, investigators are encouraged to obtain information from the patient's primary care practitioner (physician or any other medical care provider). Investigators are also requested to try as much as possible to re-contact those patients at the end of the trial to obtain at least their vital status as well as their status with respect to the primary endpoint, and thus avoid lost to follow-up for the efficacy assessment.

If patients are lost to follow-up, the CRF must be completed up to the last visit or contact.

Statistics

Analysis Populations

Randomized Population

The randomized population will include all patients who sign the informed consent form and are assigned a randomization number at Visit 2 (Day 0).

Intent-to-Treat Population

The Intent-to-Treat (ITT) population will consist of all randomized patients who take at least one dose of study drug. The ITT population is the primary analysis population. All efficacy analyses will be performed on the ITT population.

Per-Protocol Population

The per-protocol (PP) population will include all ITT patients without any major protocol deviations, and who had ≥80% compliance with study drug while on treatment (up to discontinuation for patients whose treatment is terminated early). The per-protocol efficacy analysis for CV events will be restricted to each patient's time on study drug plus 30 days thereafter.

Safety Population

All safety analyses will be conducted based on the safety population, which is defined as all randomized patients who receive at least one dose of study drug. This is the same as the ITT population.

Statistical Methods

Safety and efficacy variables will be analyzed using appropriate statistical methods to be described in detail in a separate Statistical Analysis Plan (SAP). The SAP will be finalized before study unblinding.

Patient Disposition and Demographic/Baseline Characteristics

The numbers of patients screened, the number of patients randomized per treatment group (randomized population), and the number of patients in the ITT and PP populations by treatment group will be listed.

For randomized patients who discontinued treatment with study drug, the primary reason for discontinuation will be listed and summarized by treatment group.

Summary statistics (mean, standard deviation, median, minimum and maximum) will be provided by treatment group for demographic characteristics (e.g., age, sex, race, and ethnicity) and baseline characteristics (e.g., body weight, height, and body mass index) in the ITT and PP populations.

Demographic data and baseline characteristics will be compared among treatment groups for the ITT and PP population. Differences in demographic and baseline characteristics will be tested using a chi-square test (for categorical variables) or a 1-way analysis of variance model with treatment as a factor (for continuous variables). The p-values will be used as descriptive statistics, primarily as an assessment of the adequacy of randomization.

Study Medication Exposure and Compliance

The final compliance to study drug will be calculated as the percent of doses taken relative to doses scheduled to be taken. Overall percent compliance will be calculated per patient in the ITT and PP populations and summarized by treatment group using summary statistics (n, mean, standard deviation, median, minimum, and maximum).

Concomitant Therapies

Concomitant medication/therapy verbatim terms will be coded using the latest version of the World Health Organization Drug Dictionary. The numbers and percentages of patients in each treatment group taking concomitant medications will be summarized by anatomic and therapeutic chemical classification and preferred term.

Analysis of Efficacy

For efficacy endpoints including CV events, only adjudicated events will be included in the final statistical analyses.

Summary Statistics

Summary statistics (n, mean, standard deviation, median, minimum, and maximum) for the baseline and post-baseline measurements, the percent changes, or changes from baseline will be presented by treatment group and by visit for all efficacy variables to be analyzed. The summary statistics will include changes in body weight and body mass index from baseline by treatment group and by visit.

Primary Endpoint

The primary efficacy endpoint is the time from randomization to the first occurrence of any component of the composite of the following clinical events:

CV death,
Nonfatal MI (including silent MI),
Nonfatal stroke,
Coronary revascularization,
Hospitalization for unstable angina determined to be caused by myocardial ischemia by invasive/non-invasive testing.

The analysis of the primary efficacy endpoint will be performed using the log-rank test comparing the 2 treatment groups (AMR101 and placebo) and including the stratification factor "CV risk category", use of ezetimibe and geographical region (Westernized, Eastern European, and Asia Pacific countries) (each as recorded in the IWR at the time of enrollment) as covariates. Treatment difference will be tested at alpha level of 0.0476 accounting for one interim efficacy analysis. The hazard ratio for treatment group (AMR101 vs. placebo) from a Cox proportional hazard model that includes the stratification factor will also be reported, along with the associated 95% confidence interval. Kaplan-Meier estimates from randomization to the time to the primary efficacy endpoint will be plotted.

The size and direction of the treatment effects of the individual components of the composite endpoint and their relative contribution to the composite endpoint will be determined as well.

Secondary Endpoints

The statistical analyses of the secondary endpoints will be analyzed by the same log-rank test specified above for the primary efficacy endpoint. Treatment differences will be tested at alpha level of 0.05 using a sequential procedure for controlling type 1 error starting with the key secondary variable. The remaining secondary variables will be tested in the order specified in Section 9.2.2. Estimates of the hazard ratios from the Cox proportional hazard model and the associated 95% confidence intervals will also be provided. Kaplan-Meier estimates from randomization the time to the secondary efficacy endpoints will be plotted.

Tertiary Endpoints

For event rates, the statistical analyses of the tertiary endpoints will be similar to the analysis of the secondary efficacy endpoints. All tertiary analyses will be conducted for the ITT population. No adjustments for multiple testing will be made.

For measurements of lipids, lipoproteins and inflammatory markers the change from baseline will be analyzed in the units of each marker, and the percent change from baseline. Since these biomarkers are typically not normally distributed, the Wilcoxon rank-sum test will be used for treatment comparisons of the percent change from baseline, and medians and quartiles will be provided for each treatment group. The medians of the differences between the treatment groups and 95% confidence intervals will be estimated with the Hodges-Lehmann method.

New onset diabetes is defined as Type 2 diabetes newly diagnosed during the treatment/follow-up period (i.e. patients with no history of diabetes at randomization).

For purposes of this study, a diagnosis of diabetes is made based on the observation of:

1. $HbA_{1c} \geq 6.5\%$. The test should be performed in a laboratory using a method that is National Glycohemoglobin Standardization Program (NGSP) certified and standardized to the Diabetes Control and Complications Trial (DCCT) assay. In the absence of unequivocal hyperglycemia, $HbA_{1c} \geq 6.5\%$ should be confirmed by repeat testing.

OR

2. Fasting plasma glucose (FPG)≥126 mg/dL (7.0 mmol/L). Fasting is defined as no caloric intake for at least 8 hr. In the absence of unequivocal hyperglycemia, FPG≥126 mg/dL (7.0 mmol/L) should be confirmed by repeat testing.

OR 3. 2-hr plasma glucose ≥200 mg/dL (11.1 mmol/L) during an Oral Glucose Tolerance Test (OGTT). The test should be performed as described by the World Health Organization, using a glucose load containing the equivalent of 75 g anhydrous glucose dissolved in water. In the absence of unequivocal hyperglycemia, 2-hr plasma glucose ≥200 mg/dL (11.1 mmol/L) during an Oral Glucose Tolerance Test (OGTT) should be confirmed by repeat testing.

OR

4. In a patient with classic symptoms of hyperglycemia or hyperglycemic crisis, a random plasma glucose ≥200 mg/dL (11.1 mmol/L).

Exploratory Subgroup Analyses

Subgroup analyses of the primary and key secondary endpoints (as defined in the Statistical Analysis Plan) will be performed. All subgroup analyses will be conducted for the ITT population. No adjustments for multiple testing will be made.

Log-rank tests, treatment effects and the associated 95% confidence intervals for the primary and key secondary efficacy endpoints within each subgroup will be provided using the Cox proportional hazard model with treatment (AMR101 or placebo), and stratification as a factor (with the exception of the subgroup analyses of those subgroup variables related to the stratification factors, i.e., CV risk category that will not have stratification as a factor).

Subgroups including, but not limited to the following, will be explored. A complete list will be prospectively defined in the Statistical Analysis Plan.

Demographics:
Gender,
age (<65 yr and ≥65 yr),
race (white and nonwhite, or any other subset with at least 10% of the total number of patients),
geography (western vs. non-western)
Disease Parameters:
CV risk category,
the presence/absence of diabetes at baseline,
renal impairment
Treatment Parameters:
by statin intensity (statin type and regimen),
relevant concomitant medications,
Baseline Lipid and Lipoprotein Parameters:
LDL-C (by tertile),
HDL-C (by tertile),
TG (by tertile),
TG≥150 mg/dL,
TG≥200 mg/dL and TG<200 mg/dL, combined highest tertile for TG and lowest tertile for HDL-C,
hs-CRP (≤3 mg/L and >3 mg/L),
Apo B (by tertile),
non-HDL-C (by tertile)

The consistency of the treatment effects in subgroups will be assessed for the primary and key secondary efficacy endpoints. For each subgroup variable, a Cox proportional hazard model with terms for treatment, stratification factors (with the exception of those subgroup variables related to the stratification factors, i.e., CV risk category), subgroup, and treatment-by-subgroup interaction will be performed. The main treatment effect will not be tested with this model. P-values for testing the interaction terms will be provided.

Interim Efficacy Analysis

One interim analysis will be performed for the primary efficacy endpoint using best available data (adjudicated events and site reported endpoints) based on data when approximately 60% of the total number of primary endpoint events is reached. The interim analysis will be based on a group sequential design that includes early stopping rules for benefit while preserving the overall Type I error rate (O'Brien-Fleming). This allows for interim analysis and preserves the overall Type I error probability of α=0.05 for the primary endpoint.

Approximately 1612 primary efficacy endpoint events are planned to be observed during the trial, based on sample size calculation assumptions. Therefore, the interim analysis will occur after at least 967 primary efficacy endpoint events have been observed. According to this boundary, the critical p-value at the interim analysis has to be p≤0.0076, resulting in the final evaluation p-value of 0.0476.

The interim results of the study will be monitored by an independent DMC. The analyses will be performed by the independent statistical group unblinded to the treatment assignment. The results will be reported only to the DMC. The unblinded information will not be released to sponsor under any circumstance before the completion of the study. Specific statistical guidelines for data monitoring will be discussed and formalized in a separate Interim Statistical Analysis Plan and DMC Charter.

Analysis of Safety

All analyses of safety will be conducted on the safety population, which is defined as all randomized patients who receive at least one dose of study drug. The safety assessment will be based on the frequency of adverse events, physical exams, vital signs and safety laboratory tests.

Adverse events with new onset during the study between the initiation of study drug and 30 days after the last dose of study drug for each patient will be considered treatment-emergent (TEAEs). This will include any AE with onset prior to initiation of study drug and increased severity after the treatment initiation.

Treatment-emergent adverse events will be summarized by system organ class and preferred term, and by treatment. This will include overall incidence rates (regardless of severity and relationship to study drug), and incidence rates for moderate or severe adverse events. A summary of SAEs and adverse events leading to early discontinuation from the study will be presented through data listings.

Safety laboratory tests and vital signs will be summarized by post-treatment change from baseline for each of the parameters using descriptive statistics by treatment group. Those patients with significant laboratory abnormalities will be identified in data listings. Additional safety parameters will be summarized in data listings.

Sample Size Determination

Sample size estimation is based on the assumption that the primary composite endpoint (time from randomization to the first occurrence of CV death, non-fatal MI, non-fatal stroke, coronary revascularization, or unstable angina requiring hospitalization) would be relatively reduced by 15%, from an event rate by 4 years of 23.6% in the placebo group to 20.5% in the AMR101 group. It is expected that a minimum of 1612 primary efficacy endpoint events will be required during the study. A total of approximately 6990 patients are needed to be able to detect this difference at 4.76% significance level (because of the interim analysis described in Section 12.2.4.6) and with 90% power, assuming an 18-month enrollment period and a median follow-up of 4 years. The current sample size calculation is based on an estimated placebo yearly event rate of 5.9% (23.6% over 4 years). To protect against the possibility that the actual placebo event rate is lower than estimated, an extra 1000 patients will be enrolled (approximately 7990 patients in total). By adding the extra 1000 patients, the event rate in the placebo group could be 5.2% per year (20.8% over 4 years) without having to modify the other sample size assumptions.

Since this is an events-driven trial, the 'sample size' is the number of events rather than the number of patients. The number of events that occur depends primarily on three factors: how many patients are enrolled, the combined group event rate, and how long the patients are followed. Because of the difficulty in predicting the combined event rate, the sponsor will monitor that event rate as the trial progresses. If the combined event rate is less than anticipated, either increasing the number of patients, extending the length of follow-up, or a balance of adjusting both factors may be necessary to achieve the sample size of 1612 events.

Before completing the enrollment phase of the trial, i.e. approximately 3- to 6-months prior to the projected enrollment of the 7990th patient, the actual event rate based on pooled, blinded accumulation of primary efficacy endpoint events will be calculated and plotted. If those analyses suggest the number of patients with at least 1 adjudicated, primary event (and appropriately accounting for patients with potential primary events for which the adjudication process is then incomplete) is consistent with projections, then the study could continue toward the protocol-specified target enrollment of 7990 patients. However, if the number of such events appears less than, and inconsistent with projections, the Sponsor will consider (under blinded conditions) re-calculating the number of patients needed to achieve the target number of events within the desired timeline or extend the follow-up period. If the projected increase in number of patients is ≤25% of the original 7990 target population, the Sponsor may, with documented approval of both the REDUCE-IT Steering Committee (SC) and the Data Monitoring Committee (DMC), extend enrollment to the revised target number without need for an additional protocol amendment. Under those conditions, all principal investigators, ethics committees, and regulatory authorities associated with the protocol will be promptly notified of the action. Should the projected increase in number of patients be more than 25% above the original 7990 target (i.e. more than 1998 additional patients) a formal protocol amendment will be initiated.

If the number of patients to be studied is increased, the enrollment phase will be extended to allow enrollment of the additional patients.

At completion of study enrollment, the actual number of patients randomized may vary from the target number (either original or revised) as a result of the inherent lag between the date the last patient started screening and the date the last patient was randomized.

Monitoring, Data Management, and Record Keeping

Data Management

Data Handling

Data will be recorded at the site on CRFs. All entries on a CRF are ultimately the responsibility of the Investigator, who is expected to review each form for completeness and accuracy before signing. A CRF must be completed for each randomized patient. The CRFs and source documents must be made available to the Sponsor and/or its designee.

Record Keeping

The Investigator must maintain all documents and records, originals or certified copies of original records, relating to the conduct of this trial, and necessary for the evaluation and reconstruction of the clinical trial. This documentation includes, but is not limited to protocol, CRFs, AE reports, patient source data (including records of patients, patient visit logs, clinical observations and findings), correspondence with health authorities and IRB, consent forms, inventory of study product, Investigator's curriculum vitae, monitor visit logs, laboratory reference ranges and laboratory certification or quality control procedures, and laboratory director curriculum vitae.

The Investigator and affiliated institution should maintain the trial documents as required by the applicable regulations. The Investigator and affiliated institution should take measures to prevent accidental or premature destruction of documents. Clinical trial documents must be kept in the clinical site's archives indefinitely, unless written authorization is obtained from the Sponsor.

Direct Access to Source Data/Documents

The investigator and research institution agree that the Sponsor, their representatives and designees, the IRB or IEC, and representatives from worldwide regulatory agencies will have the right, both during and after the clinical trial, to review and inspect pertinent medical records related to the clinical trial.

Quality Control and Quality Assurance

The Sponsor and/or its designee(s) will perform quality control and quality assurance checks of all clinical trials that it sponsors. Before the enrollment of any patient in this study, the Sponsor or its designee will review with the investigator and site personnel the following documents: protocol, Investigator's Brochure, CRFs and procedures for their completion, the informed consent process, and the procedure for reporting SAEs. Site visits will be performed by the Sponsor and/or its designees. During these visits, information recorded on the CRFs will be verified against source documents and requests for clarification or correction may be made. After the CRF data is entered by the site, the Sponsor or designee will review for safety information, completeness, accuracy, and logical consistency. Computer programs that identify data inconsistencies may be used to help monitor the clinical trial. If necessary, requests for clarification or correction will be sent to investigators.

By signing the protocol, the Sponsor agrees directly or through its designee(s) to be responsible for implementing and maintaining quality control and quality assurance systems with written standard operating procedures to ensure that trials are conducted and data are generated, documented, and reported in compliance with the protocol, accepted standards of Good Clinical Practice (GCP), International Conference on Harmonization (ICH) and other applicable regulations.

Completion of Study

The end of the study will be at the time of the last patient-last visit of the follow-up period of the study. The IRB and IEC will be notified about the end of the study according to country-specific regulatory requirements.

TABLE 1

SCHEDULE OF PROCEDURES

| | Screening | | | Follow-Up (FU) [13] | | | | | |
|---|---|---|---|---|---|---|---|---|---|
| Study Day | Up to 42 days before Day 0 | If a Visit 1.1 takes place, Visit 1 may occur up to 60 days before Day 0[2] | 0 | 120 ± 10 | 360 ± 10 | 720 ± 10 | 1080 ± 10 | 1440 ± 10 | 1800 ± 30 |
| Months of FU | | | 0 | 4 | 12 | 24 | 36 | 48 | 60 |
| Years of FU | | | 0 | 0.33 | 1 | 2 | 3 | 4 | 5 |
| Visit # | 1 | 1.1 | 2 | 3 | 4 | 5 | 6 | 7 | LV [14] |
| Study Procedures: | | | | | | | | | |
| Informed | X | | | | | | | | |

TABLE 1-continued

SCHEDULE OF PROCEDURES

| | Screening | | | | | | | | |
|---|---|---|---|---|---|---|---|---|---|
| | Up to 42 days | If a Visit 1.1 takes place, Visit 1 may occur up to | | Follow-Up (FU) [13] | | | | | |
| Study Day | before Day 0 | 60 days before Day 0[2] | 0 | 120 ± 10 | 360 ± 10 | 720 ± 10 | 1080 ± 10 | 1440 ± 10 | 1800 ± 30 |
| Consent Medical, Surgical & Family History | X | | | | | | | | |
| Demographics | X | | | | | | | | |
| Evaluate inclusion/exclusion criteria | X [1] | X [3] | X | | | | | | |
| Physical Examination | | | X | X | X | X | X | X | X |
| Weight, Height [4] | X | | X | X | X | X | X | X | X |
| Vital Signs [5] | X | X | X | X | X | X | X | X | X |
| Waist Circumference | | | X | | | X | | | X |
| 12-Lead ECG | X | | X | | X | X | X | X | X |
| Urine pregnancy test [6] | X | | X | | | | | | |
| Concomitant Meds | X | X | X | X | X | X | X | X | X |
| Randomization | | | X | | | | | | |
| Dosing at the Research Site [7] | | | X | X | X | X | X | X | |
| Efficacy events | | | | X | X | X | X | X | X |
| AE Evaluations | | X | X | X | X | X | X | X | X |
| Compliance Check [8] | | | | X | X | X | X | X | X |
| Chemistry and hematology [9] | X | X [3] | X | X | X | X | X | X | X |
| Fasting lipid profile [10] | X | X [3] | X | X | X | X | X | X | X |
| Genetic testing [11] | | | X | | | | | | |
| Biomarkers: hs-CRP, apo B, hsTNT | | | X | | | X | | | X |
| Fasting blood sample for archiving [12] | | | X | | X | X | X | X | X |

What is claimed is:

1. A method of reducing risk of a cardiovascular event in a subject on statin therapy with residual atherogenic dyslipidemia and clinically evident cardiovascular disease, the method comprising administering to the subject a pharmaceutical composition comprising about 4 g of eicosapentaenoic acid in triglyceride form per day for a period of at least about 2 years, wherein said administration reduces risk of cardiovascular death, risk of unstable angina and/or need for coronary revascularization.

2. The method of claim 1, wherein the composition is administered to the subject in 1 to 4 dosage units per day.

3. The method of claim 1, wherein the eicosapentaenoic acid in triglyceride form comprises at least about 96 wt. % of all omega-3 fatty acids in the pharmaceutical composition.

4. The method of claim 1 further comprising a step of measuring the subject's baseline lipid profile prior to administering the pharmaceutical composition to the subject.

5. The method of claim 1, wherein the subject has one or more of: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 to about 30 mg/dL; and/or a baseline LDL-C value of about 40 to about 100 mg/dL.

6. The method of claim 1, wherein the subject has: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 to about 30 mg/dL; and/or a baseline LDL-C value of about 40 to about 100 mg/dL.

7. The method of claim 1, wherein the statin therapy comprises administering to the subject a statin and optionally ezetimibe.

8. The method of claim 1, wherein the subject: (a) has not been administered 200 mg or more per day of niacin and/or fibrates for at least 28 days before administration of the pharmaceutical composition; (b) has not been administered omega-3 fatty acid prescription for a period of time beginning 28 days prior to administration of the pharmaceutical composition; or (c) has not ingested dietary supplements comprising omega-3 fatty acids for a period of time beginning 28 days prior to administration of the pharmaceutical composition.

9. The method of claim 1, wherein the subject is administered about 4 g of the pharmaceutical composition per day for at least about 3 years.

10. The method of claim 1, wherein the pharmaceutical composition is formulated to delay onset of a first said cardiovascular event of said subject compared with control subjects, wherein each said control subject is on stable statin therapy, has a fasting baseline triglyceride level of about 135 mg/dL to about 500 mg/dL, and has established cardiovascular disease.

11. The method of claim 10, wherein the medicament is formulated to delay onset of a second said cardiovascular event of said subject compared with control subjects.

12. The method of claim 10, wherein the subject has diabetes mellitus and the control subjects each have diabetes mellitus.

13. The method of claim 10, wherein the subject has metabolic syndrome and the control subjects each have metabolic syndrome.

14. The method of claim 1, wherein the administration further reduces the risk of stroke and/or risk of myocardial infarction.

15. A method of reducing risk of a cardiovascular event in a subject on statin therapy with residual atherogenic dyslipidemia and clinically evident cardiovascular disease, the method comprising administering to the subject a pharmaceutical composition comprising about 4 g of eicosapentaenoic acid in triglyceride form per day for a period of at least about 2 years, wherein said administration reduces risk of cardiovascular death, need for coronary revascularization, risk of unstable angina, risk of stroke and/or risk of myocardial infarction.

16. The method of claim 15, wherein the composition is administered to the subject in 1 to 4 dosage units per day.

17. The method of claim 15, wherein the eicosapentaenoic acid in triglyceride form comprises at least about 96 wt. % of all omega-3 fatty acids in the pharmaceutical composition.

18. The method of claim 15 further comprising a step of measuring the subject's baseline lipid profile prior to administering the pharmaceutical composition to the subject.

19. The method of claim 15, wherein the subject has one or more of: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 to about 30 mg/dL; and/or a baseline LDL-C value of about 40 to about 100 mg/dL.

20. The method of claim 15, wherein the subject has: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 to about 30 mg/dL; and/or a baseline LDL-C value of about 40 to about 100 mg/dL.

21. The method of claim 15, wherein the statin therapy comprises administering to the subject a statin and optionally ezetimibe.

22. The method of claim 15, wherein the subject: (a) has not been administered 200 mg or more per day of niacin and/or fibrates for at least 28 days before administration of the pharmaceutical composition; (b) has not been administered omega-3 fatty acid prescription for a period of time beginning 28 days prior to administration of the pharmaceutical composition; or (c) has not ingested dietary supplements comprising omega-3 fatty acids for a period of time beginning 28 days prior to administration of the pharmaceutical composition.

23. The method of claim 15, wherein the subject is administered about 4 g of the pharmaceutical composition per day for at least about 3 years.

24. The method of claim 15, wherein the pharmaceutical composition is formulated to delay onset of a first said cardiovascular event of said subject compared with control subjects, wherein each said control subject is on stable statin therapy, has a fasting baseline triglyceride level of about 135 mg/dL to about 500 mg/dL, and has established cardiovascular disease.

25. The method of claim 24, wherein the first cardiovascular event of the subject is stroke and/or myocardial infarction.

26. The method of claim 24, wherein the first cardiovascular event of the subject and the first cardiovascular event of the control subjects is stroke.

27. The method of claim 24, wherein the first cardiovascular event of the subject and the first cardiovascular event of the control subjects is myocardial infarction.

28. The method of claim 24, wherein the medicament is formulated to delay onset of a second said cardiovascular event of said subject compared with control subjects.

29. The method of claim 24, wherein the subject has diabetes mellitus and the control subjects each have diabetes mellitus.

30. The method of claim 24, wherein the subject has metabolic syndrome and the control subjects each have metabolic syndrome.

* * * * *